United States Patent [19]

Bujard et al.

[11] Patent Number: 5,789,156
[45] Date of Patent: Aug. 4, 1998

[54] TETRACYCLINE-REGULATED TRANSCRIPTIONAL INHIBITORS

[75] Inventors: Hermann Bujard, Heidelberg, Germany; Manfred Gossen, El Cerrito, Calif.

[73] Assignees: BASF AG; Knoll AG, both of Ludwigshafen, Germany

[21] Appl. No.: 383,754

[22] Filed: Feb. 3, 1995

Related U.S. Application Data

[63] Continuation-in-part of Ser. No. 275,876, Jul. 15, 1994, Pat. No. 5,654,168, which is a continuation-in-part of Ser. No. 270,637, Jul. 1, 1994, abandoned, and a continuation-in-part of Ser. No. 260,452, Jun. 14, 1994, Pat. No. 5,650,298, which is a continuation-in-part of Ser. No. 76,327, Jun. 14, 1993, abandoned, and a continuation-in-part of Ser. No. 76,726, Jun. 14, 1993, Pat. No. 5,464,758.

[51] Int. Cl.$^6$ .......................... C12Q 1/68; C07H 21/04; C12N 1/21; C12N 15/63

[52] U.S. Cl. ...................... 435/6; 435/172.3; 435/252.3; 435/320.1; 435/69.1; 435/69.7; 435/810; 536/23.4; 536/23.7; 536/24.1; 935/6; 935/36; 935/47; 935/77

[58] Field of Search ................. 435/69.1, 70.1, 435/172.3, 240.2, 240.4, 320.1, 6, 810, 69.7, 252.3; 536/23.4, 24.1, 23.7; 935/6, 36, 47

[56] References Cited

U.S. PATENT DOCUMENTS

| | | | |
|---|---|---|---|
| 4,833,080 | 5/1989 | Brent et al. | 435/172.3 |
| 5,221,778 | 6/1993 | Byrne et al. | 800/2 |

FOREIGN PATENT DOCUMENTS

| | | |
|---|---|---|
| 0 332 416 | 9/1989 | European Pat. Off. . |
| 0 455 424 A2 | 11/1991 | European Pat. Off. . |
| 0 455 687 B1 | 11/1991 | European Pat. Off. . |
| 0 494 724 A2 | 7/1992 | European Pat. Off. . |
| WO 91/19784 | 12/1991 | WIPO . |
| WO 91/19796 | 12/1991 | WIPO . |

(List continued on next page.)

OTHER PUBLICATIONS

Hinrichs, W., et al., (1994) "Structure of the Tet Repressor–Tetracycline Complex and Regulation of Antibiotic Resistance", *Science*, vol. 264, pp. 418–420.

Hecht, B., et al., (1993) "Noninducible Tet Repressor Mutations Map from the Operator Motif to the C Terminus", *Journal of Bacteriology*, vol. 175, No. 4.

(List continued on next page.)

*Primary Examiner*—Carla J. Myers
*Attorney, Agent, or Firm*—Lahive & Cockfield, LLP; Giulio A. DeConti, Jr.; Catherine J. Kara

[57] ABSTRACT

Nucleic acid molecules and proteins useful for regulating the expression of genes in eukaryotic cells and organisms in a highly controlled manner are disclosed. In the regulatory system of the invention, transcription of a tet operator-linked nucleotide sequence is inhibited by a transcriptional inhibitor fusion protein composed of two polypeptides, a first polypeptide which binds to tet operator sequences either (i) in the absence but not the presence of tetracycline (or an analogue thereof) or (ii) in the presence but not the absence of tetracycline (or an analogue thereof), and a second polypeptide which directly or indirectly inhibits transcription in eukaryotic cells. In one embodiment, the fusion protein comprises a Tet repressor operatively linked to a transcriptional silencer polypeptide. In another embodiment, the fusion protein comprises a mutated Tet repressor operatively linked to a transcriptional silencer polypeptide. The fusion proteins of the invention are useful for reducing the level of transcription of a tet operator-linked target gene. Moreover, the fusion proteins of the invention can be used in combination with tetracycline-regulated transcriptional activator fusion proteins to allow for precise regulation of the expression of one or multiple target genes. Kits including the components of the regulatory system of the invention are also encompassed by the invention.

49 Claims, 12 Drawing Sheets

FOREIGN PATENT DOCUMENTS

| | | |
|---|---|---|
| WO 92/11874 | 7/1992 | WIPO. |
| WO 92/20808 | 11/1992 | WIPO. |
| WO 93/04169 | 3/1993 | WIPO. |
| WO 93/23431 | 11/1993 | WIPO. |
| WO 94/04672 | 3/1994 | WIPO. |
| WO 94/18317 | 8/1994 | WIPO. |
| WO 94/29442 | 12/1994 | WIPO. |

OTHER PUBLICATIONS

Gossen, M., et al., (1993) "Control of gene activity in higher eukaryotic cells by prokaryotic regulatory elements", *TIBS*, vol. 18, No. 12, pp. 471–475.

Fieck, A., et al., (1992) "Modification of the *E. Coli* Lac Repressor for Expression in Eukaryoitic Cells: Effect of Nuclear Signal Sequence on Protein Activity and Nuclear Documentation", *Nucleic Acid Research*, vol. 20, pp. 1785–1791.

Seipel, K., et al., (1992) "Different activation domains stimulate transcription from remote('enhancer') and proximal ('promoter') positions", *The EMBO Journal*, vol. 11, No. 13, pp. 4961–4968.

Epstein–Baak, R., et al.,(1992) "Inducible Transformation of Cells from Transgenic Mice Expressing SV40 under Lac Operon Control", *Cell Growth & Differentiation*, vol. 3, pp. 127–134.

Gossen, M., and Bujard, H., (1992) "Tight control of gene expression in mammalian cells by tetracycline–responsive promoters", *Proceedings of the National Academy of Science*, vol. 89, pp. 5547–5551.

Bradley, A., (1991) "Modifying the mammalian genome by gene targeting", *Current Opinion in Biotechnology*, vol. 2, pp. 832–829.

Wyborski, D.L., and Short, J.M., (1991) "Analysis of Inducers of the *E. Coli* Lac Repressor System in Mammalian Cells and Whole Animals", *Nucleic Acid Research*, vol. 19, pp. 4647–4653.

Degenkolb, J., et al., (1991) "Structural Requirements of Tetracycline–Tet Repressor Interaction: Determination of Equilibrium Binding Constants for Tetracycline Analogs with the Tet Repressor", *Antimicrobial Agents and Chemotherapy*, vol. 35, No. 8, pp. 1591–1595.

Baim, S.B., et al., (1991) "A chimeric mammalian transactivator based on the lac repressor that is regulated by temperature and isopropyl β–D–thiogalactopyranoside", *Proceedings of the National Academy of Science*, vol. 88, pp. 5072–5076.

Gatz, C., et al., (1991) "Regulation of a modified CaMV 35S promoter by the Tn 10–encoder Tet receptor in transgenic tobacco", *Mol. Gen. Genet.*, vol. 227, No. 2, pp. 229–237.

Wissmann, A., et al., (1991) "Selection for Tn10 Tet Repressor Binding to tet Operator in *Eschericia coli* : Isolation of Temperature–Sensitive Mutants and Combinatorial Mutagenesis in the DNA Binding Motif", *Genetics*, vol. 128, pp. 225–232.

Labow, M.A., et al., (1990) "Conversion of the lac Repressor into an Allosterically Regulated Transcriptional Activator for Mammalian Cells", *Molecular and Cellular Biology*, vol. 10, No. 7, pp. 3343–3356.

Deuschle, U., et al., (1989) "Regulated expression of foreign genes in mammalian cells under the control of coliphage T3 RNA polymerase and lac repressor", *Proceedings of the National Academy of Science*, vol. 86, pp. 5400–5404.

Capecchi, M.R., (1989) "Altering the Genome by Homologous Recombination", *Science*, vol. 244, pp. 1288–1292.

Mermod, N., et al., (1989) "The Proline–Rich Transcriptional Activator of CTF/NF–I Is Distinct from the Replication and DNA Binding Domain", *Cell*, vol. 58, 741–753.

Mansour, S.L., et al., (1988) "Disruption of the proto–oncogene int–2 in mouse embyo–derived stem cells: a general strategy for targeting mutations to non–selectable genes", *Nature*, vol. 336, pp. 348–352.

Gatz, C., and Quail, P.H., (1988) "Tn10–encoded tet repressor can regulate an operator–containing plant promoter", *Proceedings of the National Academy of Science*, vol. 85, pp. 1394–1397.

Figge, J., et al., (1988) "Stringent Regulation of Stably Integrated Chloramphenicol Acetyl Transferase Genes by *E. coli* lac Repressor in Monkey Cells", *Cell*, vol. 52, 713–722.

Triezenberg, S.J. et al., (1988) "Functional dissection of VP16, the trans–activator of herpes simplex virus immediate early gene expression", *Genes & Development*, vol. 2, pp. 718–729.

Courey, A.J., and Tijan, R., (1988) "Analysis of Sp1 In Vivo Reveals Multiple Transcriptional Domains, Including a Novel Glutamine–Rich Activation Motif", *Cell*, vol. 55, pp. 887–898.

Tovar, K., et al., (1988) "Identification and nucleotide sequence of the class E tet regulatory elements and operator and inducer binding of the encoded purified Tet repressor", *Mol. Gen. Genet.*, vol. 215, pp. 76–80.

Altschmeid, L. et al., (1988) "A threonine to alanine exchange at position 40 of Tet repressor alters the recognition of the sixth base pair of tet operator from GC to AT", *The EMBO Journal*, vol. 7, No. 12, pp. 4011–4017.

Brown, M., et al., (1987) "lac Repressor Can Regulate Expression from a Hybrid SV40 Early Promoter Containing a lac Operator in Animal Cells", *Cell*, vol. 49, pp. 603–612.

Hu.M.C–T and Davidson, N., (1987) "The Inducible lac Operator–Repressor System Is Functional in Mamalian Cells", *Cell*, vol. 46, pp. 555–566.

Smithies, O., et al., (1985) "Insertion of DNA sequences into the human chromosomal β–globin locus by homologous recombination", *Nature*, vol. 317, pp. 230–234.

Boshart, M., et al., (1985) "A Very Strong Enhancer Is Located Upstream of an Immediate Early Gene of Human Cytomegalovirus", *Cell*, vol. 41, No. 2, pp. 521–530.

Postle, K., et al., (1984) "Nucleotide sequence of the repressor gene of the TN10 tetracycline resistance determinant", *Nucleic Acid Research*, vol. 12, No. 12, pp. 4849–4863.

Unger, B., et al., (1984) "Nucleotide sequence of the gene, protein purification and characterization of the pSC101–encoded tetracycline resistance–gene–repressor", *Gene*, vol. 31, pp. 103–108.

Unger, B., et al., (1984) "Nucleotide sequence of the repressor gene of the RA1 tetracycline resistance determinant: structural and functional comparison with three related Tet repressor genes", *Nucleic Acid Research*, vol. 12, No. 20, pp. 7693–7703.

Waters, S.H, et al., (1983) "The tetracycline resistance determinants of RP1 and Tn1721: nucleotide sequence analysis", *Nucleic Acid Research*, vol. 11, No. 17, pp. 6089–6105.

Hillen, W., and Schollmeier, K., (1983) "Nucleotide sequence of the Tn10 encoded tetracycline resistance gene", *Nucleic Acid Research*, vol. 11, No. 2, pp. 525–539.

Brent, R. and M. Ptashne (1984) "A Bacterial Repressor Protein or a Yeast Transcriptional Terinator Can Block Upstream Activation of A Yeast Gene"*Nature* 312:612–615.

Brent R. and M. Ptashne (1985) "A Eukaryotic Transcriptional Activator Bearing the DNA Specificity of a Prokaryotic Repressor" *Cell* 43:729–736.

Baniahmad, A. et al. (1992) "A Transferable Silencing Domain Is Present In the Thyroid Hormone Receptor, in the v–erbA Oncogene Product and In the Retinoic Acid Receptor" *The EMBO Journal* 11(3):1015–1023.

Sauer, F. and H. Jäckle (1993) "Dimerization and the Control of Transcription by Krüppel" *Nature* 364:454–457.

Licht, J. et al. (1990) "Drosophila Krüppel Protein is a Transcriptional Repressor" *Nature* 346:76–79.

Herschbach B. and A. Johnson (1993) "Transcriptional Repression In Eukaryotes" *Annu. Rev. Cell Biol.* 9:479–509.

Renkawitz R. (1990) "Transcriptional Repression In Eukaryotes" *TIG* 6(6):192–193.

Resnitsky D. (1994) "Acceleration of the G1/S Phase Transition by Expression of Cyclins D1 and E with an Inducible System" *Molecular and Cellular Biology* 14(3):1669–1679.

Furth P. (1994) "Temporal Control of Gene Expression in Transgenic Mice By A Tetracycline–Responsive Promoter" *Proc. Natl. Acad. Sci. USA* 91:9302–9306.

Wimmel A. et al. (1994) "Inducible Acceleration of G1 Progression Through Tetracycline–Regulated Expression of Human Cyclin E" *Oncogene* 9:995–997.

Crameri A. and W. Stemmer (1995) "Efficacy of Tetracycline–Controlled Gene Expression Is Influenced by Cell Type" *BioTechniques* 18(2):196–200.

Gossen M. and B. Hermann (1993) "Anhydrotetracycline, A Novel Effector of Tetracycline Controlled Gene Expression Systems In Eurkaryotic Cells" *Nucleic Acids Research* 21(18):4411–4412.

Buckbinder L. et al. (1994) "Gene Regulation by Temperature–Sensitive p53 Mutants: Identification of p53 response genes" *Proc. Natl. Acad. Sci. USA* 91:10640–10644.

Yarranton G. (1992) "Inducible Vectors For Expression In Mamalian Cells" *Current Opinion in Biotechnology* 3:506–511.

Gossen et al., (1994) "Inducible Gene Expression Systems For Higher Eukaryotic Cells" *Current Opinion in Biotechnology* 5:516–520.

Weinmann P. et al. (1994) "A Chimeric Transactivator Allows Tetracycline–Responsive Gene Expression in Whole Plants" *The Plant Journal* 5(4): 559–569.

Pescini R. et al. (194) "Inducible Inhibition of Eukaryotic Gene Expression" *Biochemical and Biophysical Research Communications* (202):1664–1667.

Fishman G. et al. (1994) "Tetracycline–Regulated Cardiac Gene Expression in Vivo" *J. Clin. Invest.* 93:1864–1868.

Cowell, "Repression versus activation in the control of gene transcription," *Trends in Biochemical Sciences*, 19:1, 38–42 (1994).

Deuschle et al., "Tetracycline–reversible silencing of eukaryotic promoters," *Mol. Cell. Biol.*, 15:4, 1907–1914 (1995).

Gatz et al., "Stringent repression and homogenous de–repression by tetracycline of a modified CaMV 35S promoter in intact transgenic tobacco plants," *The Plant Journal*, 2:3, 397–404 (1992).

Gossen et al., "Exploiting prokaryotic elements for the control of gene activity in higher eukaryotics," Keystone Symposium on Gene Therapy and Molecular Medicine, Steamboat Springs, Colorado, *Journal of Cellular Biochemistry*, Supplement O (21A), Abstract No. C6–220, 355 (1995).

Gossen et al., "Transcriptional activation by tetracyclines in mammalian cells," *Science*, 268:5218, 1766–1769 (1995).

Liang et al., "Enhanced and switchable expression systems for gene–transfer," Keystone Symposium on Gene Therapy and Molecular Medicine, Steamboat Springs, Colorado, *Journal of Cellular Biochemistry*, Supplement O (21A), Abstract No. C6–220, 379 (1995).

Orkin et al, Report and Recommendations of the Panel to Assess the NIH Investment in Research on Gene Therapy (Dec. 7, 1995).

```
MSRLDKSKVINSALELLNEVGIEGLTTRKLAQKLGVEQPTLYWHVKNKRALLDALAIEMLDRH   63  B
MA--NRES--DA--G----T--DE----------I----------------------V-I-A--      D
MTK-QPNT--RA--D-----VD-------ER---Q-A----FR-----------EA--AEN        A
MNK-QREA--RT--G---D--H------R-ER---Q-A----F-----------EA--TIN        C
MTK---GT--AAG------MDS------ER-K-Q--A----FQ-----------PEA--RER       G
MA--SLDD--SM--T--DSE-L---------S-KI----------R--QT-MNM-SEAI-AK-      E
```

```
                ┌────┐         ┌──┐          ┌────┐
                │ 5  │         │6 │          │ 7  │
                └────┘         └──┘          └────┘
●● ●  ●    ●   ●●  ●   ● ●●●●●●●●● ● ●● ●● ●●
```

```
HTHFCPLEGESWQDFLRNNAKSFRCALLSHRDGAKVHLGTRPTEKQYETLENQLAFLCQQGFS   126 B
-DYSL-AA-----S------M---R---RY----------D----D-V-T--R-MTEN---        D
---SV-RADDD-RS--IG--R---Q---AY----RI-A----GAP-M--ADA--R---EA---      A
---ST-RDDDD-RS--KG--C---R---AY----RI-A----AAP-M-KADA--R---DA---      C
--RSL-E-N-D-RV--KE--L---T----Y----RI-A------PNFG-A-T-IR---AE--C     G
--RSA--PT----Q--QE--L---K---V-----RL-I--S--PP-F-QA-A--RC--DA---      E
```

```
      ┌──────────┐                    ┌──────┐
      │    8     │                    │  9   │
      └──────────┘                    └──────┘
        ● ●●  ●●●●●● ●●    ●●          ●  ●● ●●●
```

```
LENALYALSAVGHFTLGCVLEDQEHQVAKEERE    TPTTDSHPPLLRQAIELFDHQGA      182 B
-RDG---I---S-----A---Q---TA-LTD-P    AAPDENL-----E-LQIM-SDDG      182 D
AGD-VN---MTISY--V-A---E-AGDSESG--GG  -VEQAPLS----A--DA--EA-P      183 A
AGD-T---H-ISY--V-A---Q-ASEADA---GEDQL-TSAST--AR-QS-HKIVYEA-P      186 C
PKR-VW--R--S-YVV-S---Q-ASDAD   -VPDRPDVSEQAPSSF-HVLFHELETD-M     184 G
V-E--FI-QSIS-----A---E-ATNQIENNHV    I-AA----QE-FNIQARTS-         179 E
```

```
   ┌──────────┐
   │    10    │
   └──────────┘
      ●
```

```
EPAFLFGLELIICGLEKQLKCESGS              207 B
-Q---H---SL-R-F-V--TALLQIVGGDKLIIPFC    218 D
DA--EQ--AV-VD--A-RRLVVRNVEGPRKGDD       216 A
DA--ER-A---G----MRLTTNDIEVLKNVDE        219 C
DA--N---DSL-A-F-RLRAAVLATD              210 G
-M--H---KSL-F-FSA--DEKKHTPIEDGNK        211 E
```

FIG. 5

A1: ACTTTATCACTGATAAACA / TGAAATAGTGACTATTTGT
A2: AACTTATCAGTGATAAGAA / TTGAATAGTCACTATTTCT

B1: ACTCTATCATTGATAGAGT / TGAGATAGTAACTATCTCA
B2: TCCCTATCAGTGATAGAGA / AGGGATAGTCACTATCTCT

C1: AGCTTATCATCGATAAGCT / TCGAATAGTAGCTATTCGA
C2: AGTTTATCACAGTTAAATT / TCAAATAGTGTCAATTTAA

D1: ACTCTATCATTGATAGGGA / TGAGATAGTAACTATCCCT
D2: ACTCTATCAATGATAGGA / TGAGATAGTTACTATCCT

E1: AATCTATCACTGATAGAGT / TTAGATAGTGACTATCTCA
E2: ACCCTATCATCGATAGAGA / TGGGATAGTAGCTATCTCT

FIG. 7A

```
                                              5' GAATTCGGGG
                                                 ─────
                                                 EcoRI    +75

CCGCGGAGGCTGGATCGGTCCCGGTGTCCGGTGTCTTCTATGGAGGTCAAAACAGCGTGGA

+1
              ┌──
            ←─┘
              C                                         P hCMV*-3
TGGCGTCTCCAGGCGATCTGACGGTTCACTAAACGAGCTCTGCTTATATAGG
                                                     -31 tet O
   TC ( GAGTTTACCACTCCCTATCAGTGATAGAGAAAAGTGAAAGTC )₇GAGC
        ─────────────────────▶◀──────────────

P hCMV*-1
TCGGTACCCGGGTCGAGTAGGCGTGTACGGTGGGAGGCCTATATAAGCAGAG
        -53

CTCGTTTAGTGAACCGTCAGATCGCCTGGAGACGCCATCCACGCTGTTTTGA
                  └────▶
                  +1

CCTCCATAGAAGACACCGGGACCGATCCAGCCTCCGCGGCCCCGAATTC 3'
                                            ─────
                                            +75  EcoRI
```

TETRACYCLINE-REGULATED TRANSCRIPTIONAL INHIBITORS

RELATED APPLICATIONS

This application is a continuation-in-part of U.S. Ser. No. 08/275,876, filed Jul. 15, 1994, now U.S. Pat. No. 5,654, 168, which is a continuation-in-part of U.S. Ser. No. 08/270, 637, filed Jul. 1, 1994, now abandoned, and a continuation-in-part of U.S. Ser. No. 08/260,452, filed Jun. 14, 1994, now U.S. Pat. No. 5,650,298 which is a continuation-in-part of U.S. Ser. No. 08/076,327, filed Jun. 14, 1993, now abandoned, and a continuation-in-part of U.S. Ser. No. 08/076,726, filed Jun. 14, 1993, now U.S. Pat. No. 5,464, 758. The contents of each of these applications are incorporated herein by reference.

BACKGROUND OF THE INVENTION

Functional analysis of cellular proteins is greatly facilitated through changes in the expression level of the corresponding gene for subsequent analysis of the accompanying phenotype. For this approach, an inducible expression system controlled by an external stimulus is desirable. Ideally such a system would not only mediate an "on/off" status for gene expression but would also permit limited expression of a gene at a defined level.

Attempts to control gene activity have been made using various inducible eukaryotic promoters, such as those responsive to heavy metal ions (Mayo et al. (1982) *Cell* 29:99–108; Brinster et al. (1982) *Nature* 296:39–42; Searle et al. (1985) *Mol. Cell. Biol.* 5:1480–1489), heat shock (Nouer et al. (1991) in *Heat Shock Response*, e.d. Nouer, L. , CRC, Boca Raton, Fla., pp 167–220) or hormones (Lee et al. (1981) *Nature* 294:228–232; Hynes et al. (1981) *Proc. Natl. Acad. Sci. USA* 78:2038–2042; Klock et al. (1987) *Nature* 329:734–736; Israel & Kaufman (1989) *Nucl. Acids Res.* 17:2589–2604). However, these systems have generally suffered from one or both of the following problems: (1) the inducer (e.g. heavy metal ions, heat shock or steroid hormones) evokes pleiotropic effects, which can complicate analyses, and (2) many promoter systems exhibit high levels of basal activity in the non-induced state, which prevents shut-off the regulated gene and results in modest induction factors.

An approach to circumventing these limitations is to introduce regulatory elements from evolutionarily distant species such as *E. coli* into higher eukaryotic cells with the anticipation that effectors which modulate such regulatory circuits will be inert to eukaryotic cellular physiology and, consequently, will not elicit pleiotropic effects in eukaryotic cells. For example, the Lac repressor (lacR)/operator/ inducer system of *E. coli* functions in eukaryotic cells and has been used to regulate gene expression by three different approaches: (1) prevention of transcription initiation by properly placed lac operators at promoter sites (Hu & Davidson (1987) *Cell* 48:555–566; Brown et al. (1987) *Cell* 49:603–612; Figge et al. (1988) *Cell* 52:713–722; Fuerst et al. (1989) *Proc. Natl. Acad. Sci. USA* 8:2549–2553: Deuschle et al. (1989) *Proc. Natl. Acad. Sci. USA* 86:5400–5405); (2) blockage of transcribing RNA polymerase II during elongation by a LacR/operator complex (Deuschle et al. (1990) *Science* 2:480–483); and (3) activation of a promoter responsive to a fusion between LacR and the activation domain of herpes simples virus (HSV) virion protein 16 (VP16) (Labow et al. (1990) *Mol. Cell. Biol.* 10:3343–3356; Baim et al. (1991) *Proc. Natl. Acad. Sci. USA* 88:5072–5076).

In one version of the Lac system, expression of lac operator-linked sequences is constitutively activated by a LacR-VP16 fusion protein and is turned off in the presence of isopropyl-β-D-thiogalactopyranoside (IPTG) (Labow et al. (1990), cited supra). In another version of the system, a lacR-VP16 variant is used which binds to lac operators in the presence of IPTG, which can be enhanced by increasing the temperature of the cells (Baim et al.(1991), cited supra). The utility of these lac systems in eukaryotic cells is limited, in part, because IPTG acts slowly and inefficiently in eukaryotic cells and must be used at concentrations which approach cytotoxic levels. Alternatively, use of a temperature shift to induce gene expression is likely to elicit pleiotropic effects in the cells. Thus, there is a need for a more efficient inducible regulatory system which exhibits rapid and high level induction of gene expression and in which the inducer is tolerated by eukaryotic cells without cytotoxicity or pleiotropic effects.

Components of the tetracycline (Tc) resistance system of *E. coli* have also been found to function in eukaryotic cells and have been used to regulate gene expression. For example, the Tet repressor (TetR), which binds to tet operator sequences in the absence of tetracycline and represses gene transcription, has been expressed in plant cells at sufficiently high concentrations to repress transcription from a promoter containing tet operator sequences (Gatz, C. et al. (1992) *Plants* 2:397–404). However, very high intracellular concentrations of TetR are necessary to keep gene expression down-regulated in cells, which may not be achievable in many situations, thus leading to "leakiness" in the system.

In other studies, TetR has been fused to the activation domain of VP16 to create a tetracycline-controlled transcriptional activator (tTA) (Gossen, M. and Bujard, H. (1992) *Proc. Natl. Acad. Sci. USA* 89:5547–5551). The tTA fusion protein is regulated by tetracycline in the same manner as TetR, i.e., tTA binds to tet operator sequences in the absence of tetracycline but not in the presence of tetracycline. Thus, in this system, in the continuous presence of Tc, gene expression is kept off, and to induce transcription, Tc is removed.

SUMMARY OF THE INVENTION

This invention pertains to a regulatory system which utilizes components of the Tet repressor/operator/inducer system of prokaryotes to regulate gene expression in eukaryotic cells. In particular, this invention provides tetracycline-regulated transcriptional inhibitors which are useful for inhibiting expression, in a highly controlled manner, of a gene linked to one or more tet operator sequences. The transcriptional inhibitors of the invention comprise a fusion protein composed of at least two polypeptides, a first polypeptide that binds to tet operator sequences and a heterologous second polypeptide that directly or indirectly inhibits transcription in eukaryotic cells. The heterologous the second polypeptide is derived from a different protein than the first polypeptide. Because the fusion proteins of the invention include a eukaryotic transcriptional silencer domain, they are anticipated to be more efficient at repressing transcription in eukaryotic cells than is a Tet Repressor alone.

In one embodiment of the invention, the first polypeptide of the inhibitor fusion protein binds to tet operator sequences in the absence but not the presence of tetracycline (Tc) or an analogue thereof (e.g., the first polypeptide is preferably a Tet repressor, such as a Tn10-derived Tet repressor having an amino acid sequence shown in SEQ ID NO: 17). In the absence of tetracycline (or Tc analogue), this fusion protein binds to tet operator sequences operatively linked to a gene of interest, thereby inhibiting transcription of the gene of interest. In another embodiment, the first polypeptide binds to tet operator sequences in the presence but not the absence of tetracycline (e.g., the first polypeptide is preferably a mutated Tet repressor, such as a Tn10-derived Tet repressor having an amino acid substitution at position 71, 95, 101 and/or 102). Preferably, the first polypeptide has an amino acid sequence shown in SEQ ID NO: 19. In the presence of tetracycline (or Tc analogue), this fusion protein binds to tet operator sequences operatively linked to a gene of interest, thereby inhibiting transcription of the gene of interest.

The second polypeptide can be a transcriptional "silencer" domain from a protein such as the v-erbA oncogene product, the Drosophila Krueppel protein, the retinoic acid receptor alpha, the thyroid hormone receptor alpha, the yeast Ssn6/Tup1 protein complex, the Drosophila protein even-skipped, SIR1, NeP1, the Drosophila dorsal protein, TSF3, SFL, the Drosophila hunchback protein, the Drosophila knirps protein, WT1, Oct-2.1, the Drosophila engrailed protein, E4BP4 or ZF5. Preferred silencer domains include amino acid residues 403–466 of Krueppel (shown in SEQ ID NO: 21) and amino acid residues 364–635 of v-erbA (shown in SEQ ID NO: 23).

The fusion proteins of the invention may further comprise additional polypeptides, such as a third polypeptide which promotes transport of the fusion protein into a cell nucleus (i.e., a nuclear transport amino acid sequence).

This invention further provides isolated nucleic acid molecules encoding the transcriptional inhibitor fusion proteins of the invention and recombinant expression vectors containing these nucleic acid molecules in a form suitable for expression of the encoded transcriptional inhibitor fusion protein in a host cell. The invention still further provides host cells into which a recombinant expression vectors of the invention has been introduced. Thus, a transcriptional inhibitor fusion protein is expressed in these host cells. The host cell can be, for example, a mammalian cell (e.g., a human cell), a yeast cell, a fungal cell or an insect cell. Moreover, the host cell can be a fertilized non-human oocyte, in which case the host cell can be used to create a transgenic organism having cells that express the transcriptional inhibitor fusion protein. Still further, the recombinant expression vector can be designed to allow homologous recombination between the nucleic acid encoding the fusion protein and a target gene in a host cell. Such homologous recombination vectors can be used to create homologous recombinant animals that express a fusion protein of the invention.

In a preferred embodiment, the host cells (or cells of a host organism) also contain a nucleotide sequence to be transcribed operatively linked to at least one tet operator sequence (e.g., a gene of interest whose expression can be regulated by Tc or an analogue thereof). To regulate transcription of the tet operator-linked gene of interest in these host cells, the concentration of Tc (or analogue thereof) in contact with the host cell is altered. For example, when the transcriptional inhibitor fusion protein binds to tet operator sequences in the absence of Tc, the concentration of Tc in contact with the cells is decreased to thereby inhibit transcription of the tet operator-linked gene of interest (e.g., if cells are first cultured in the presence of Tc, then Tc can be removed from the culture medium to inhibit transcription of the gene of interest). Alternatively, when the transcriptional inhibitor fusion protein binds to tet operator sequences in the presence of Tc, the concentration of Tc in contact with the cells is increased to thereby inhibit transcription of the tet operator-linked gene of interest (e.g., if cells are first cultured in the absence of Tc, then Tc can be added to the culture medium to inhibit transcription of the gene of interest).

The transcriptional inhibitor fusion proteins of the invention are useful for inhibiting gene expression in a variety of situations, as described further herein. In a particularly preferred embodiment, transcription of a tet operator(tetO)-linked gene of interest is regulated by a combination of tetracycline-regulated transcriptional inhibitor and activator fusion proteins in the same host cell to allow for precise control of the expression level of the gene of interest. For example, an activator fusion protein that binds to tetO only in the presence of Tc and an inhibitor fusion protein that binds to tetO only in the absence of Tc are expressed in a host cell that contains a tetO-linked gene of interest. In the absence of Tc, basal levels of transcription of the gene of interest are inhibited by the inhibitor fusion protein. Upon contact of the cell with Tc (or analogue), transcription of the gene of interest is stimulated by the activator fusion protein. The activator and inhibitor fusion proteins of the invention can also be used in combination to regulate the expression of multiple tetO-linked genes of interest.

Novel kits for regulating the expression of a gene of interest are also within the scope of the invention. The kits of the invention can include a first nucleic acid molecule encoding a transcriptional inhibitor fusion protein of the invention and second nucleic acid molecule into which a gene of interest can be cloned such that the gene is operatively linked to a tet operator sequence(s). The kits may further contain a third nucleic acid molecule encoding a transcriptional activator fusion protein. Alternatively, the first and third nucleic acids (encoding the fusion proteins) may be stably incorporated into a eukaryotic host cell that is included in the kit. Moreover, at least one tetracycline or tetracycline analogue may be included in the kits.

BRIEF DESCRIPTION OF THE DRAWINGS

FIG. 4 shows the amino acid sequences of various classes of Tet repressors, illustrating the homology between the amino acid sequences of different classes of Tet repressors, as compared to class B Tet repressors (e.g., Tn10-derived). Amino acid positions in other classes of Tet repressors that are identical to class B are indicated by a dash.

FIG. 5 shows the nucleotide sequences of tet operators of different classes: class A (SEQ ID NO: 11), class B (SEQ ID NO: 12), class C (SEQ ID NO: 13), class D (SEQ ID NO: 14) and class E (SEQ ID NO: 15).

FIG. 7A (SEQ ID NO: 6) shows the nucleotide sequence of a bidirectional promoter region for coordinate regulation of two genes of interest by a tetracycline-regulated transcriptional activator.

FIG. 9A illustrates self-regulation of expression of a wild-type Tet repressor-containing transactivator fusion protein that binds to tet operators in the absence of Tc. FIG. 9B illustrates self-regulation of expression of a mutated Tet repressor-containing transactivator fusion protein that binds to tet operators in the presence of Tc.

DETAILED DESCRIPTION OF THE INVENTION

Figure 1:
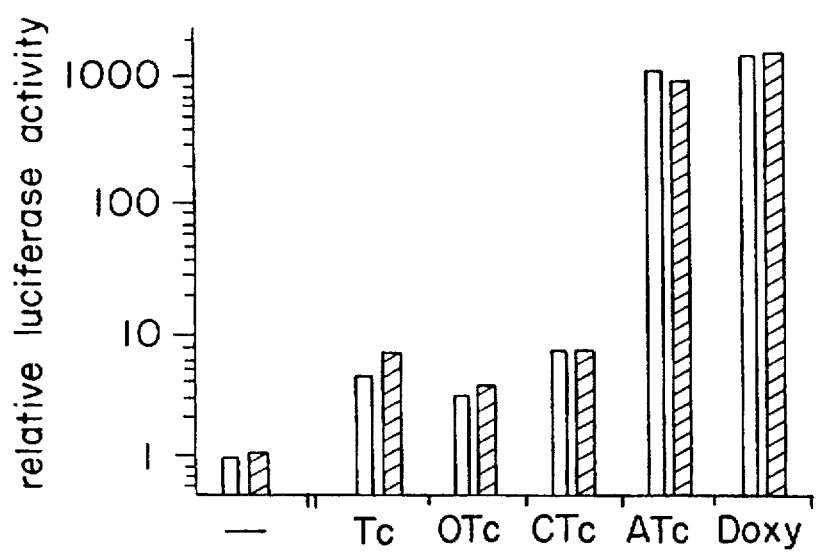
FIG. 1 is a bar graph depicting the stimulation of luciferase activity in HR5-C11 cells by tetracycline and different tetracycline analogues (1 µg/ml f.c.). Cells were grown in the absence (−) or presence of the indicated tetracyclines for 3 days before luciferase activity was determined. Each solid and hatched bar represents the luciferase activity of a single culture dish.

This invention pertains to nucleic acid molecules and proteins which can be used to regulate the expression of genes in eukaryotic cells or animals in a highly controlled manner. Regulation of gene expression by the system of the invention involves at least two components: A gene which is operatively linked to a regulatory sequence and a protein which, in either the presence or absence of an inducible agent, binds to the regulatory sequence and either activates or inhibits transcription of the gene. The system of the invention utilizes components of the Tet repressor/operator/inducer system of prokaryotes to stimulate gene expression in eukaryotic cells.

Various aspects of the invention pertain to fusion proteins which are capable of either activating or inhibiting gene transcription when bound to tet operator (tetO) sequences, but which bind to tet operator sequences only in the presence or, alternatively, in the absence of tetracycline, or an analogue thereof. Thus, in a host cell, transcription of a gene operatively linked to a tet operator sequence(s) is stimulated or inhibited by a fusion protein of the invention by altering the concentration of tetracycline (or analogue) in contact with the host cell (e.g., adding or removing tetracycline from a culture medium, or administering or ceasing to administer tetracycline to a host organism, etc.).

The invention further pertains to target transcription units for regulation by the fusion protein of the invention. In addition to allowing for regulation of a single tet-operator linked gene of interest, the invention also provides novel transcription units containing two or more genes to be transcribed that can be regulated in either a coordinate or independent manner by a transactivator fusion protein of the invention. Methods for stimulating or inhibiting transcription of a gene using tetracycline (or analogues thereof), and kits which contain the components of the regulatory system described herein, are also encompassed by the invention.

In the following subsections, the nucleic acids and proteins comprising the components of the inducible regulatory system of the invention, and their interrelationship, are discussed in greater detail. The subsections are as follows:

I. Tetracycline-Inducible Transcriptional Activators
  A. The first polypeptide of the transactivator fusion protein
  B. The second polypeptide of the transactivator fusion protein
  C. A third polypeptide of the transactivator fusion protein
II. Expression of a Transactivator Fusion Protein
  A. Expression vectors
  B. Host cells
  C. Introduction of nucleic acid into host cells
  D. Transgenic Organisms
  E. Homologous Recombinant Organisms
III. Target Transcription Units Regulated by a Tetracycline-Inducible Transactivator
  A. Regulation of expression of tet operator-linked nucleotide sequences
  B. Coordinate regulation of two nucleotide sequences
  C. Independent regulation of multiple nucleotide sequences
  D. Combined coordinate and independent regulation of multiple nucleotide sequences
IV. Tetracycline-Regulated Transcriptional Inhibitors
  A. The first polypeptide of the transcritional inhibitor fusion protein
  B. The second polypeptide of the transcritional inhibitor fusion protein
  C. A third polypeptide of the transcritional inhibitor fusion protein
  D. Expression of the transcriptional inhibitor fusion protein
V. Kits of the Invention
VI. Regulation of Gene Expression by Tetracycline or Analogues Thereof
  A. Stimulation of gene expression by transactivator fusion proteins
  B. Inhibition of gene expression by transcriptional inhibitor fusion proteins
  C. Combined positive and negative regulation of gene expression
VII. Applications of the Invention
  A. Gene Therapy
  B. Production of Proteins in Vitro
  C. Production of Proteins in Vivo
  D. Animal Models of Human Disease
  E. Production of Stable Cell Lines for Cloning I. Tetracycline-Inducible Transcriptional Activators In the inducible regulatory system of the invention, transcription of a gene is activated by a transcriptional activator protein, also referred to herein simply as a transactivator.

The transactivator of the invention is a fusion protein. One aspect of the invention thus pertains to fusion proteins and nucleic acids (e.g., DNA) encoding fusion proteins. The term "fusion protein" is intended to describe at least two polypeptides, typically from different sources, which are operatively linked. With regard to the polypeptides, the term "operatively linked" is intended to mean that the two polypeptides are connected in manner such that each polypeptide can serve its intended function. Typically, the two polypeptides are covalently attached through peptide bonds. The fusion protein is preferably produced by standard recombinant DNA techniques. For example, a DNA molecule encoding the first polypeptide is ligated to another DNA molecule encoding the second polypeptide, and the resultant hybrid DNA molecule is expressed in a host cell to produce the fusion protein. The DNA molecules are ligated to each other in a 5' to 3' orientation such that, after ligation, the translational frame of the encoded polypeptides is not altered (i.e., the DNA molecules are ligated to each other in-frame).

A. The first polypeptide of the transactivator fusion protein

The transactivator fusion protein of the invention is composed, in part, of a first polypeptide which binds to a tet operator sequence in the presence of tetracycline (Tc), or an analogue thereof. The first polypeptide of the fusion protein is preferably a mutated Tet repressor. The term "mutated Tet repressor" is intended to include polypeptides having an amino acid sequence which is similar to a wild-type Tet repressor but which has at least one amino acid difference from the wild-type Tet repressor. The term "wild-type Tet repressor" is intended to describe a protein occurring in nature which represses transcription from tet operator sequences in prokaryotic cells in the absence of Tc. The amino acid difference(s) between a mutated Tet repressor and a wild-type Tet repressor may be substitution of one or more amino acids, deletion of one or more amino acids or addition of one or more amino acids. The mutated Tet repressor of the invention has the following functional properties: 1) the polypeptide can bind to a tet operator sequence, i.e., it retains the DNA binding specificity of a wild-type Tet repressor; and 2) it is regulated in a reverse manner by tetracycline than a wild-type Tet repressor, i.e., the mutated Tet repressor binds to a tet operator sequence only the presence of Tc (or Tc analogue) rather than in the absence of Tc.

In a preferred embodiment, a mutated Tet repressor having the functional properties described above is created by substitution of amino acid residues in the sequence of a wild-type Tet repressor. For example, as described in Example 1, a Tn10-derived Tet repressor having amino acid substitutions at amino acid positions 71, 95, 101 and 102 has the desired functional properties and thus can be used as the first polypeptide in the transactivator fusion protein of the invention. The amino acid sequence of this mutated Tet repressor is shown in SEQ ID NO: 2 (positions 1–207). In one embodiment of the mutated Tet repressor, position 71 is mutated from glutamic acid to lysine, position 95 is mutated from aspartic acid to asparagine, position 101 is mutated from leucine to serine and position 102 is mutated from glycine to aspartic acid, although the invention is not limited to these particular mutations. Mutation of fewer than all four of these amino acid positions may be sufficient to achieve a Tet repressor with the desired functional properties. Accordingly, a Tet repressor is preferably mutated at at least one of these positions. Other amino acid substitutions, deletions or additions at these or other amino acid positions which retain the desired functional properties of the mutated Tet repressor are within the scope of the invention. The crystal structure of a Tet repressor-tetracycline complex, as described in Hinrichs, W. et al. (1994) Science 264:418–420, can be used for rational design of mutated Tet repressors. Based upon this structure, amino acid position 71 is located outside the tetracycline binding pocket, suggesting mutation at this site may not be necessary to achieve the desired functional properties of a mutated Tet repressor of the invention. In contrast, amino acid positions 95, 101 and 102 are located within the conserved tetracycline bidding pocket. Thus, the tetracycline binding pocket of a Tet repressor may be targeted for mutation to create a mutated Tet repressor of the invention.

Additional mutated Tet repressors for incorporation into a fusion protein of the invention can be created according to the teachings of the invention. A number of different classes of Tet repressors have been described, e.g., A, B, C, D and E (of which the Tn10-encoded repressor is a class B repressor). The amino acid sequences of the different classes of Tet repressors share a high degree of homology (i.e., 40–60% across the length of the proteins), including in the region encompassing the above-described mutations. The amino acid sequences of various classes of Tet repressors are shown and compared in FIG. 4, and are also described in Tovar, K. et al. (1988) Mol. Gen. Genet. 215:76–80. Accordingly, equivalent mutations to those described above for the Tn10-derived Tet repressor can be made in other classes of Tet repressors for inclusion in a fusion protein of the invention. For example, amino acid position 95, which is an aspartic acid in all five repressor classes, can be mutated to asparagine in any class of repressor. Similarly, position 102, which is glycine in all five repressor classes, can be mutated to aspartic acid in any class of repressor. Additional suitable equivalent mutations will be apparent to those skilled in the art and can be created and tested for functionality by procedures described herein. Nucleotide and amino acid sequences of Tet repressors of the A, C, D and E classes are disclosed in Waters, S. H. et al. (1983) Nucl. Acids Res 11:6089–6105, Unger, B. et al. (1984) Gene 3: 103–108, Unger, B. et al. (1984) Nucl Acids Res. 12:7693–7703 and Tovar, K. et al. (1988) Mol. Gen. Genet. 215:76–80, respectively. These wild-type sequences can be mutated according to the teachings of the invention for use in the inducible regulatory system described herein.

Alternative to the above-described mutations, additional suitable mutated Tet repressors (i.e., having the desired functional properties described above) can be created by mutagenesis of a wild type Tet repressor and selection as described in Example 1. The nucleotide and amino acid sequences of wild-type class B Tet repressors are disclosed in Hillen, W. and Schollmeier, K. (1983) Nucl. Acids Res. 11:525–539 and Postle, K. et al. (1984) Nucl. Acids Res. 12:4849–4863. The nucleotide and amino acid sequences of wild-type class A, C, D and E type repressors are cited above. A mutated Tet repressor can be created and selected, for example as follows: a nucleic acid (e.g., DNA) encoding a wild-type Tet repressor is subjected to random mutagenesis and the resultant mutated nucleic acids are incorporated into an expression vector and introduced into a host cell for screening. A screening assay is used which allows for selection of a Tet repressor which binds to a tet operator sequence only in the presence of tetracycline. For example, a library of mutated nucleic acids in an expression vector can be introduced into an E. coli strain in which tet operator sequences control the expression of a gene encoding a Lac repressor and the Lac repressor controls the expression of a gene encoding an selectable marker (e.g., drug resistance).

Binding of a Tet repressor to tet operator sequences in the bacteria will inhibit expression of the Lac repressor, thereby inducing expression of the selectable marker gene. Cells expressing the marker gene are selected based upon the selectable phenotype (e.g., drug resistance). For wild-type Tet repressors, expression of the selectable marker gene will occur in the absence of Tc. A nucleic acid encoding a mutated Tet repressor is selected using this system based upon the ability of the nucleic acid to induce expression of the selectable marker gene in the bacteria only in the presence of Tc.

A first polypeptide of the transactivator fusion protein (e.g., the mutated Tet repressor) has the property of binding specifically to a tet operator sequence. Each class of Tet repressor has a corresponding target tet operator sequence. Accordingly, the term "tet operator sequence" is intended to encompass all classes of tet operator sequences, e.g. class A, B, C, D, and E. Nucleotide sequences of these five classes of tet operators are shown in FIG. 5 and SEQ ID NOs: 11–15, and are described in Waters, S. H. et al. (1983) cited supra, Hillen, W. and Schollenmeier, K. (1983) cited supra, Stüber, D. and Bujard, H. (1981) *Proc. Natl. Acad. Sci. USA* 78:167–171, Unger, B. et al. (1984) cited supra and Tovar, K. et al. (1988) cited supra. In a preferred embodiment, the mutated Tet repressor is a Tn10-encoded repressor (i.e., class B) and the tet operator sequence is a class B tet operator sequence. Alternatively, a mutated class A Tet repressor can be used with a class A tet operator sequence, and so on for the other classes of Tet repressor/operators.

Another approach for creating a mutated Tet repressor which binds to a class A tet operator is to further mutate the already mutated Tn10-derived Tet repressor described herein (a class B repressor) such that it no longer binds efficiently to a class B type operator but instead binds efficiently to a class A type operator. It has been found that nucleotide position 6 of class A or B type operators is the critical nucleotide for recognition of the operator by its complimentary repressor (position 6 is a G/C pair in class B operators and an A/T pair in class A operators) (see Wissman et al. (1988) *J. Mol. Biol.* 202:397–406). It has also been found that amino acid position 40 of a class A or class B Tet repressor is the critical amino acid residue for recognition of position 6 of the operator (amino acid position 40 is a threonine in class B repressors but is an alanine in class A repressors). It still further has been found that substitution of Thr40 of a class B repressor with Ala alters its binding specificity such that the repressor can now bind a class A operator (similarly, substitution of Ala40 of a class A repressor with Thr alters its binding specificity such that the repressor can now bind a class B operator) (see Altschmied et al. (1988) *EMBO J.* 7:4011–4017). Accordingly, one can alter the binding specificity of the mutated Tn10-derived Tet repressor disclosed herein by additionally changing amino acid residue 40 from Thr to Ala by standard molecular biology techniques (e.g., site directed mutagenesis).

A mutated Tet repressor having specific mutations (e.g., at positions 71, 95, 101 and/or 102, as described above) can be created by introducing nucleotide changes into a nucleic acid encoding a wild-type repressor by standard molecular biology techniques, e.g. site directed mutagenesis or PCR-mediated mutagenesis using oligonucleotide primers incorporating the nucleotide mutations. Alternatively, when a mutated Tet repressor is identified by selection from a library, the mutated nucleic acid can be recovered from the library vector. To create a transactivator fusion protein of the invention, a nucleic acid encoding a mutated Tet repressor is then ligated in-frame to another nucleic acid encoding a transcriptional activation domain and the fusion construct is incorporated into a recombinant expression vector. The transactivator fusion protein can be expressed by introducing the recombinant expression vector into a host cell or animal.

B. The second polypeptide of the transactivator fusion protein

The first polypeptide of the transactivator fusion protein is operatively linked to a second polypeptide which directly or indirectly activates transcription in eukaryotic cells. To operatively link the first and second polypeptides, typically nucleotide sequences encoding the first and second polypeptides are ligated to each other in-frame to create a chimeric gene encoding a fusion protein, although the first and second polypeptides can be operatively linked by other means that preserve the function of each polypeptide (e.g., chemically crosslinked). In a preferred embodiment, the second polypeptide of the transactivator itself possesses transcriptional activation activity (i.e., the second polypeptide directly activates transcription). In another embodiment, the second polypeptide activates transcription by an indirect mechanism, through recruitment of a transcriptional activation protein to interact with the fusion protein. Accordingly, the term "a polypeptide which activates transcription in eukaryotic cells" as used herein is intended to include polypeptides which either directly or indirectly activates transcription.

Polypeptides which can function to activate transcription in eukaryotic cells are well known in the art. In particular, transcriptional activation domains of many DNA binding proteins have been described and have been shown to retain their activation function when the domain is transferred to a heterologous protein. A preferred polypeptide for use in the fusion protein of the invention is the herpes simplex virus virion protein 16 (referred to herein as VP16, the amino acid sequence of which is disclosed in Triezenberg, S. J. et al. (1988) *Genes Dev.* 2:718–729). In one embodiment, about 127 of the C-terminal amino acids of VP16 are used. For example, a polypeptide having an amino acid sequence shown in SEQ ID NO: 2 (positions 208–335) can be used as the second polypeptide in the fusion protein. In another embodiment, at least one copy of about 11 amino acids from the C-terminal region of VP16 which retain transcriptional activation ability is used as the second polypeptide. Preferably, a dimer of this region (i.e., about 22 amino acids) is used. Suitable C-terminal peptide portions of VP16 are described in Seipel, K. et al. (*EMBO J.* (1992) 13:4961–4968). For example, a dimer of a peptide having an amino acid sequence shown in SEQ ID NO: 4 (encoded by a nucleotide sequence shown in SEQ ID NO: 3) can be used as the second polypeptide in the fusion protein.

Other polypeptides with transcriptional activation ability in eukaryotic cells can be used in the fusion protein of the invention. Transcriptional activation domains found within various proteins have been grouped into categories based upon similar structural features. Types of transcriptional activation domains include acidic transcription activation domains, proline-rich transcription activation domains, serine/threonine-rich transcription activation domains and glutamine-rich transcription activation domains. Examples of acidic transcriptional activation domains include the VP16 regions already described and amino acid residues 753–881 of GAL4. Examples of proline-rich activation domains include amino acid residues 399–499 of CTF/NF1 and amino acid residues 31–76 of AP2. Examples of serine/threonine-rich transcription activation domains include amino acid residues 1–427 of ITF1 and amino acid residues 2–451 of ITF2. Examples of glutamine-rich activation domains include amino acid residues 175–269 of Oct1 and amino acid residues 132–243 of Sp1. The amino acid sequences of each of the above described regions, and of other useful transcriptional activation domains, are disclosed in Seipel, K. et al. (*EMBO J.* (1992) 12:4961–4968).

In addition to previously described transcriptional activation domains, novel transcriptional activation domains, which can be identified by standard techniques, are within the scope of the invention. The transcriptional activation ability of a polypeptide can be assayed by linking the polypeptide to another polypeptide having DNA binding activity and determining the amount of transcription of a target sequence that is stimulated by the fusion protein. For example, a standard assay used in the art utilizes a fusion protein of a putative transcriptional activation domain and a GAL4 DNA binding domain (e.g., amino acid residues 1–93). This fusion protein is then used to stimulate expression of a reporter gene linked to GAL4 binding sites (see e.g., Seipel, K et al. (1992) *EMBO J.* 11:4961–4968 and references cited therein).

In another embodiment, the second polypeptide of the fusion protein indirectly activates transcription by recruiting a transcriptional activator to interact with the fusion protein. For example, a mutated tetR of the invention can be fused to a polypeptide domain (e.g., a dimerization domain) capable of mediating a protein-protein interaction with a transcriptional activator protein, such as an endogenous activator present in a host cell. It has been demonstrated that functional associations between DNA binding domains and transactivation domains need not be covalent (see e.g., Fields and Song (1989) *Nature* 340:245–247; Chien et al. (1991) *Proc. Natl. Acad. Sci. USA* 88:9578–9582; Gyuris et al. (1993) *Cell* 75:791–803; and Zervos, A. S. (1993) *Cell* 72:223–232). Accordingly, the second polypeptide of the fusion protein may not directly activate transcription but rather may form a stable interaction with an endogenous polypeptide bearing a compatible protein-protein interaction domain and transactivation domain. Examples of suitable interaction (or dimerization) domains include leucine zippers (Landschulz et al. (1989) *Science* 243:1681–1688), helix-loop-helix domains (Murre, C. et al. (1989) *Cell* 58:537–544) and zinc finger domains (Frankel, A. D. et al. (1988) *Science* 240:70–73). Interaction of a dimerization domain present in the fusion protein with an endogeneous nuclear factor results in recruitment of the transactivation domain of the nuclear factor to the fusion protein, and thereby to a tet operator sequence to which the fusion protein is bound.

C. A third polypeptide of the transactivator fusion protein

In addition to a mutated Tet repressor and a transcriptional activation domain, a fusion protein of the invention can contain an operatively linked third polypeptide which promotes transport of the fusion protein to a cell nucleus. Amino acid sequences which, when included in a protein, function to promote transport of the protein to the nucleus are known in the art and are termed nuclear localization signals (NLS). Nuclear localization signals typically are composed of a stretch of basic amino acids. When attached to a heterologous protein (e.g., a fusion protein of the invention), the nuclear localization signal promotes transport of the protein to a cell nucleus. The nuclear localization signal is attached to a heterologous protein such that it is exposed on the protein surface and does not interfere with the function of the protein. Preferably, the NLS is attached to one end of the protein, e.g. the N-terminus. The amino acid sequence of a non-limiting example of an NLS that can be included in a fusion protein of the invention is shown in SEQ ID NO: 5. Preferably, a nucleic acid encoding the nuclear localization signal is spliced by standard recombinant DNA techniques in-frame to the nucleic acid encoding the fusion protein (e.g., at the 5' end).

The plasmid pUHD17-1 (described in further detail in Example 1), which comprises a transactivator of the invention having the nucleotide sequence shown in SEQ ID NO: 1, has been deposited on July 8, 1994 under the provisions of the Budapest Treaty at the Deutsche Sammlung Von Mikroorganismen und ZellKulturen GmbH (DSM) in Braunschweig, Germany and assigned deposit number DSM 9279.

II. Expression of a Transactivator Fusion Protein

A. Expression Vectors

A nucleic acid of the invention encoding a transactivator fusion protein, as described above, can be incorporated into a recombinant expression vector in a form suitable for expression of the fusion protein in a host cell. The term "in a form suitable for expression of the fusion protein in a host cell" is intended to mean that the recombinant expression vector includes one or more regulatory sequences operatively linked to the nucleic acid encoding the fusion protein in a manner which allows for transcription of the nucleic acid into mRNA and translation of the mRNA into the fusion protein. The term "regulatory sequence" is art-recognized and intended to include promoters, enhancers and other expression control elements (e.g., polyadenylation signals). Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the amount of fusion protein to be expressed.

When used in mammalian cells, a recombinant expression vector's control functions are often provided by viral genetic material. For example, commonly used promoters are derived from polyoma, Adenovirus 2, cytomegalovirus and Simian Virus 40. Use of viral regulatory elements to direct expression of the fusion protein can allow for high level constitutive expression of the fusion protein in a variety of host cells. In a preferred recombinant expression vector, the sequences encoding the fusion protein are flanked upstream (i.e., 5') by the human cytomegalovirus IE promoter and downstream (i.e., 3') by an SV40 poly(A) signal. For example, an expression vector similar to that described in Example 1 can be used. The human cytomegalovirus IE promoter is described in Boshart et al. (1985) *Cell* 41:521–530. Other ubiquitously expressing promoters which can be used include the HSV-Tk promoter (disclosed in McKnight et al. (1984) *Cell* 37:253–262) and β-actin promoters (e.g., the human β-actin promoter as described by Ng et al. (1985) *Mol. Cell. Biol* 5:2720–2732).

Alternatively, the regulatory sequences of the recombinant expression vector can direct expression of the fusion protein preferentially in a particular cell type, i.e., tissue-specific regulatory elements can be used. Non-limiting examples of tissue-specific promoters which can be used include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreasspecific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

Figure 9A:
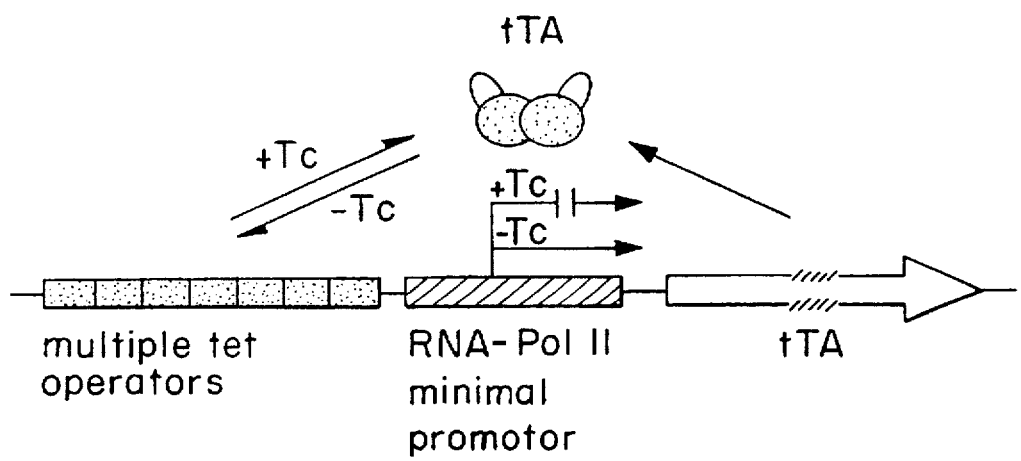
FIG. 9A–9B are schematic diagrams of self-regulating promoters for expression of tetracycline-regulated transcriptional activators (tTA).
Figure 9B:
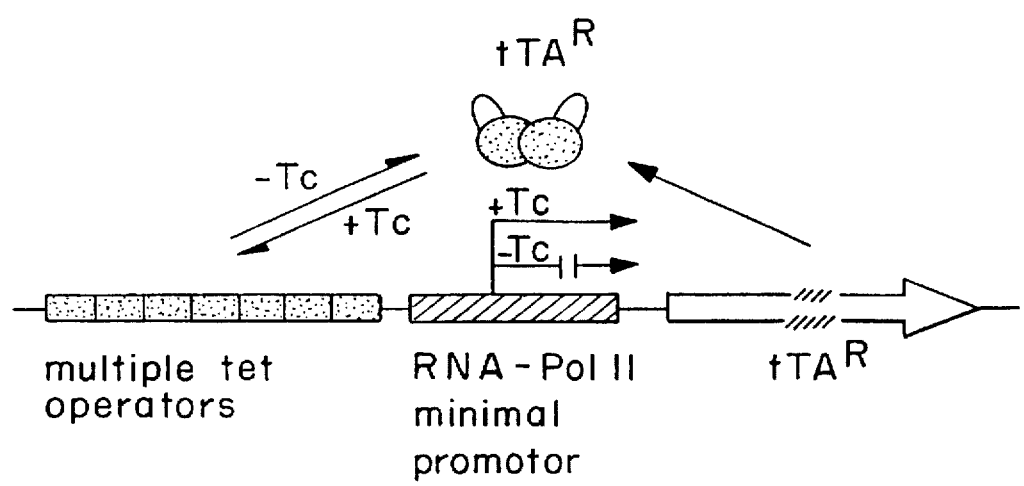

Alternatively, a self-regulating construct encoding a transactivator fusion protein can be created. To accomplish this, nucleic acid encoding the fusion protein is operatively linked to a minimal promoter sequence and at least one tet operator sequence. For example, the nucleic acid of SEQ ID NO: 1 can be linked to a promoter having a nucleotide sequence shown in SEQ ID NO: 8, 9 or 10 (the nucleic acids of SEQ ID NOs: 8 and 9 comprise a minimal CMV promoter and ten tet operators; the nucleic acids of SEQ ID NO: 10 comprises a TK promoter and ten tet operators). A schematic diagram of such a self-regulating construct is shown in FIG. 9B. When this nucleic acid is introduced into a cell (e.g., in a recombinant expression vector), a small amount of basal transcription of the transactivator gene is likely to occur due to "leakiness". In the presence of Tc (or analogue thereof) this small amount of the transactivator fusion protein will bind to the tet operator sequence(s) upstream of the nucleotide sequence encoding the transactivator and stimulate additional transcription of the nucleotide sequence encoding the transactivator, thereby leading to further production of the transactivator fusion protein in the cell. It will be appreciated by those skilled in the art that such a self-regulating promoter can also be used in conjunction with other tetracycline-regulated transactivators, such as the wild-type Tet repressor fusion protein (tTA) described in Gossen, M. and Bujard, H. (1992) *Proc. Natl. Acad. Sci. USA* 89:5547–5551, which binds to tet operators in the absence of Tc (as illustrated in FIG. 9A). When used in conjunction with this transactivator, self-regulated transcription of the nucleotide sequence encoding this transactivator is stimulated in the absence of Tc. The plasmid pUHD15-3, which comprises nucleotide sequences encoding the tTA described in Gossen and Bujard (1992), cited supra, operatively linked to a self-regulating promoter, has been deposited on July 8, 1994 under the provisions of the Budapest Treaty at the Deutsche Sammlung Von Mikroorganismen und ZellKulturen GmbH (DSM) in Braunschweig, Germany and assigned deposit number DSM 9280.

In one embodiment, the recombinant expression vector of the invention is a plasmid, such as that described in Example 1. Alternatively, a recombinant expression vector of the invention can be a virus, or portion thereof, which allows for expression of a nucleic acid introduced into the viral nucleic acid. For example, replication defective retroviruses, adenoviruses and adeno-associated viruses can be used. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. The genome of adenovirus can be manipulated such that it encodes and expresses a transactivator fusion protein but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 d1324 or other strains of adenovirus (e.g., Ad2, Ad3, Ad7 etc.) are well known to those skilled in the art. Alternatively, an adeno-associated virus vector such as that described in Tratschin et al. (1985) *Mol. Cell. Biol.* 5:3251–3260 can be used to express a transactivator fusion protein.

B. Host Cells

A fusion protein of the invention is expressed in a eukaryotic cell by introducing nucleic acid encoding the fusion protein into a host cell, wherein the nucleic acid is in a form suitable for expression of the fusion protein in the host cell. For example, a recombinant expression vector of the invention, encoding the fusion protein, is introduced into a host cell. Alternatively, nucleic acid encoding the fusion protein which is operatively linked to regulatory sequences (e.g., promoter sequences) but without additional vector sequences can be introduced into a host cell. As used herein, the term "host cell" is intended to include any eukaryotic cell or cell line so long as the cell or cell line is not incompatible with the protein to be expressed, the selection system chosen or the fermentation system employed. Non-limiting examples of mammalian cell lines which can be used include CHO dhfr⁻ cells (Urlaub and Chasin (1980) *Proc. Natl. Acad Sci. USA* 77:4216–4220), 293 cells (Graham et al. (1977) *J. Gen. Virol.* 36: pp 59) or myeloma cells like SP2 or NS0 (Galfre and Milstein (1981) *Meth. Enzymol.* 73(B):3–46).

In addition to cell lines, the invention is applicable to normal cells, such as cells to be modified for gene therapy purposes or embryonic cells modified to create a transgenic or homologous recombinant animal. Examples of cell types of particular interest for gene therapy purposes include hematopoietic stem cells, myoblasts, hepatocytes, lymphocytes, neuronal cells and skin epithelium and airway epithelium. Additionally, for transgenic or homologous recombinant animals, embryonic stem cells and fertilized oocytes can be modified to contain nucleic acid encoding a transactivator fusion protein. Moreover, plant cells can be modified to create transgenic plants.

The invention is broadly applicable and encompasses non-mammalian eukaryotic cells as well, including insect (e.g., *Sp. frugiperda*), yeast (e.g., *S. cerevisiae, S. pombe, P. pastoris, K. lactis, H. polymorpha*; as generally reviewed by Fleer, R. (1992) *Current Opinion in Biotechnology* 3(5):486–496)), fungal and plant cells. Examples of vectors for expression in yeast *S. cerivisae* include pYepSec1 (Baldari, et al., (1987) *Embo J.* 6:229–234), pMFa (Kujan and Herskowitz, (1982) *Cell* 30:933–943), pJRY88 (Schultz et al., (1987) *Gene* 54:113–123), and pYES2 (Invitrogen Corporation, San Diego, Calif.). The fusion protein can be expressed in insect cells using baculovirus expression vectors (e.g., as described in O'Reilly et al. (1992) *Baculovirus Expression Vectors: A Laboratory Manual*, Stockton Press). Baculovirus vectors available for expression of proteins in cultured insect cells (e.g., SF 9 cells) include the pAc series (Smith et al., (1983) *Mol. Cell Biol.* 3:2156–2165) and the pVL series (Lucklow, V. A., and Summers, M. D., (1989) *Virology* 170:31–39).

C. Introduction of Nucleic Acid into a Host Cell

Nucleic acid encoding the fusion protein can be introduced into a host cell by standard techniques for transfecting eukaryotic cells. The term "transfecting" or "transfection" is intended to encompass all conventional techniques for introducing nucleic acid into host cells, including calcium phosphate co-precipitation, DEAE-dextran-mediated transfection, lipofection, electroporation and microinjection. Suitable methods for transfecting host cells can be found in Sambrook et al. (*Molecular Cloning: A Laboratory Manual*, 2nd Edition, Cold Spring Harbor Laboratory press (1989)), and other laboratory textbooks.

The number of host cells transformed with a nucleic acid of the invention will depend, at least in part, upon the type of recombinant expression vector used and the type of transfection technique used. Nucleic acid can be introduced into a host cell transiently, or more typically, for long term regulation of gene expression, the nucleic acid is stably integrated into the genome of the host cell or remains as a stable episome in the host cell. Plasmid vectors introduced into mammalian cells are typically integrated into host cell DNA at only a low frequency. In order to identify these integrants, a gene that contains a selectable marker (e.g., drug resistance) is generally introduced into the host cells along with the nucleic acid of interest. Preferred selectable markers include those which confer resistance to certain drugs, such as G418 and hygromycin. Selectable markers can be introduced on a separate plasmid from the nucleic acid of interest or, are introduced on the same plasmid. Host cells transfected with a nucleic acid of the invention (e.g., a recombinant expression vector) and a gene for a selectable marker can be identified by selecting for cells using the selectable marker. For example, if the selectable marker encodes a gene conferring neomycin resistance, host cells which have taken up nucleic acid can be selected with G418. Cells that have incorporated the selectable marker gene will survive, while the other cells die.

A host cell transfected with a nucleic acid encoding a fusion protein of the invention can be further transfected with one or more nucleic acids which serve as the target for the fusion protein. The target nucleic acid comprises a nucleotide sequence to be transcribed operatively linked to at least one tet operator sequence (described in more detail in Section III below).

Nucleic acid encoding the fusion protein of the invention can be introduced into eukaryotic cells growing in culture in vitro by conventional transfection techniques (e.g., calcium phosphate precipitation, DEAE-dextran transfection, electroporation etc.). Nucleic acid can also be transferred into cells in vivo, for example by application of a delivery mechanism suitable for introduction of nucleic acid into cells in vivo, such as retroviral vectors (see e.g., Ferry, N et al. (1991) *Proc. Natl. Acad. Sci. USA* 88:8377–8381; and Kay, M. A. et al. (1992) *Human Gene Therapy* 3:641–647), adenoviral vectors (see e.g., Rosenfeld, M. A. (1992) *Cell* 68:143–155; and Herz, J. and Gerard, R. D. (1993) *Proc. Natl. Acad. Sci. USA* 90:2812–2816), receptor-mediated DNA uptake (see e.g., Wu, G. and Wu, C. H. (1988) *J. Biol. Chem.* 263:14621; Wilson et al. (1992) *J. Biol. Chem.* 267:963–967; and U.S. Pat. No. 5,166,320), direct injection of DNA (see e.g., Acsadi et al. (1991) *Nature* 332: 815–818; and Wolff et al. (1990) *Science* 247:1465–1468) or particle bombardment (see e.g., Cheng. L. et al. (1993) *Proc. Natl. Acad. Sci. USA* 90:4455–4459; and Zelenin, A. V. et al. (1993) *FEBS Letters* 315:29–32). Thus, for gene therapy purposes, cells can be modified in vitro and administered to a subject or, alternatively, cells can be directly modified in vivo.

D. Transgenic Organisms

Nucleic acid a transactivator fusion protein can transferred into a fertilized oocyte of a non-human animal to create a transgenic animal which expresses the fusion protein of the invention in one or more cell types. A transgenic animal is an animal having cells that contain a transgene, wherein the transgene was introduced into the animal or an ancestor of the animal at a prenatal, e.g., an embryonic, stage. A transgene is a DNA which is integrated into the genome of a cell from which a transgenic animal develops and which remains in the genome of the mature animal, thereby directing the expression of an encoded gene product in one or more cell types or tissues of the transgenic animal. In one embodiment, the non-human animal is a mouse, although the invention is not limited thereto. In other embodiments, the transgenic animal is a goat, sheep, pig, cow or other domestic farm animal. Such transgenic animals are useful for large scale production of proteins (so called "gene pharming").

A transgenic animal can be created, for example, by introducing a nucleic acid encoding the fusion protein (typically linked to appropriate regulatory elements, such as a constitutive or tissue-specific enhancer) into the male pronuclei of a fertilized oocyte, e.g., by microinjection, and allowing the oocyte to develop in a pseudopregnant female foster animal. Intronic sequences and polyadenylation signals can also be included in the transgene to increase the efficiency of expression of the transgene. Methods for generating transgenic animals, particularly animals such as mice, have become conventional in the art and are described, for example, in U.S. Pat. Nos. 4,736,866 and 4,870,009 and Hogan, B. et al., (1986) *A Laboratory Manual*, Cold Spring Harbor, New York, Cold Spring Harbor Laboratory. A transgenic founder animal can be used to breed additional animals carrying the transgene. Transgenic animals carrying a transgene encoding the fusion protein of the invention can further be bred to other transgenic animals carrying other transgenes, e.g., to a transgenic animal which contains a gene operatively linked to a tet operator sequence (discussed in more detail in Section III below).

It will be appreciated that, in addition to transgenic animals, the regulatory system described herein can be applied to other transgenic organisms, such as transgenic plants. Transgenic plants can be made by conventional techniques known in the art. Accordingly, the invention encompasses non-human transgenic organisms, including animals and plants, that contains cells which express the transactivator fusion protein of the invention (i.e., a nucleic acid encoding the transactivator is incorporated into one or more chromosomes in cells of the transgenic organism).

E. Homologous Recombinant Organisms

The invention also provides a homologous recombinant non-human organism expressing the fusion protein of the invention. The term "homologous recombinant organism" as used herein is intended to describe an organism, e.g. animal or plant, containing a gene which has been modified by homologous recombination between the gene and a DNA molecule introduced into a cell of the animal, e.g., an embryonic cell of the animal. In one embodiment, the non-human animal is a mouse, although the invention is not limited thereto. An animal can be created in which nucleic acid encoding the fusion protein has been introduced into a specific site of the genome, i.e., the nucleic acid has homologously recombined with an endogenous gene.

To create such a homologous recombinant animal, a vector is prepared which contains DNA encoding the fusion protein flanked at its 5' and 3' ends by additional nucleic acid of a eukaryotic gene at which homologous recombination is to occur. The additional nucleic acid flanking that encoding the fusion protein is of sufficient length for successful homologous recombination with the eukaryotic gene. Typically, several kilobases of flanking DNA (both at the 5' and 3' ends) are included in the vector (see e.g., Thomas, K.

R. and Capecchi, M. R. (1987) *Cell* 51:503 for a description of homologous recombination vectors). The vector is introduced into an embryonic stem cell line (e.g., by electroporation) and cells in which the introduced DNA has homologously recombined with the endogenous DNA are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harbouring the homologously recombined DNA in their germ cells can be used to breed animals in which all cells of the animal contain the homologously recombined DNA. These "germ-line transmission" animals can further be mated to animals carrying a gene operatively linked to at least one tet operator sequence (discussed in more detail in Section III below).

In addition to the homologous recombination approaches described above, enzyme-assisted site-specific integration systems are known in the art and can be applied to the components of the regulatory system of the invention to integrate a DNA molecule at a predetermined location in a second target DNA molecule. Examples of such enzyme-assisted integration systems include the Cre recombinase-lox target system (e.g., as described in Baubonis, W. and Sauer, B. (1993) *Nucl. Acids Res.* 21:2025–2029; and Fukushige, S. and Sauer, B. (1992) *Proc. Natl. Acad. Sci. USA* 89:7905–7909) and the FLP recombinase-FRT target system (e.g., as described in Dang, D. T. and Perrimon, N. (1992) *Dev. Genet.* 13:367–375; and Fiering, S. et al. (1993) *Proc. Natl. Acad. Sci. USA* 90:8469–8473).

III. Target Transcription Units Regulated by a Tetracycline-Inducible Transactivator A fusion protein of the invention is used to regulate the transcription of a target nucleotide sequence. This target nucleotide sequence is operatively linked to a regulatory sequence to which the fusion protein binds. More specifically, the fusion protein regulates expression of a nucleotide sequence operatively linked to at least one tet operator sequence. Accordingly, another aspect of the invention relates to target nucleic acids (e.g., DNA molecules) comprising a nucleotide sequence to be transcribed operatively linked to at least one tet operator sequence. Such nucleic acids are also referred to herein as tet-regulated transcription units (or simply transcription units).

Within a transcription unit, the "nucleotide sequence to be transcribed" typically includes a minimal promoter sequence which is not itself transcribed but which serves (at least in part) to position the transcriptional machinery for transcription. The minimal promoter sequence is linked to the transcribed sequence in a 5' to 3' direction by phosphodiester bonds (i.e., the promoter is located upstream of the transcribed sequence) to form a contiguous nucleotide sequence. Accordingly, as used herein, the terms "nucleotide sequence to be transcribed" or "target nucleotide sequence" are intended to include both the nucleotide sequence which is transcribed into mRNA and an operatively linked upstream minimal promoter sequence. The term "minimal promoter" is intended to describe a partial promoter sequence which defines the start site of transcription for the linked sequence to be transcribed but which by itself is not capable of initiating transcription efficiently, if at all. Thus, the activity of such a minimal promoter is dependent upon the binding of a transcriptional activator (such as the tetracycline-inducible fusion protein of the invention) to an operatively linked regulatory sequence (such as one or more tet operator sequences). In one embodiment, the minimal promoter is from the human cytomegalovirus (as described in Boshart et al. (1985) *Cell* 41:521–530). Preferably, nucleotide positions between about +75 to −53 and +75 to −31 are used. Other suitable minimal promoters are known in the art or can be identified by standard techniques. For example, a functional promoter which activates transcription of a contiguously linked reporter gene (e.g., chloramphenicol acetyl transferase, β-galactosidase or luciferase) can be progressively deleted until it no longer activates expression of the reporter gene alone but rather requires the presence of an additional regulatory sequence(s).

Within a transcription unit, the target nucleotide sequence (including the transcribed nucleotide sequence and its upstream minimal promoter sequence) is operatively linked to at least one tet operator sequence. In a typical configuration, the tet operator sequence(s) is operatively linked upstream (i.e., 5') of the minimal promoter sequence through a phosphodiester bond at a suitable distance to allow for transcription of the target nucleotide sequence upon binding of a regulatory protein (e.g., the transactivator fusion protein) to the tet operator sequence. That is, the transcription unit is comprised of, in a 5' to 3' direction: tet operator sequence(s)—a minimal promoter—a transcribed nucleotide sequence. It will be appreciated by those skilled in the art that there is some flexibility in the permissible distance between the tet operator sequence(s) and the minimal promoter, although typically the tet operator sequences will be located within about 200–400 base pairs upstream of the minimal promoter.

The nucleotide sequences of examples of tet-regulated promoters, containing tet operator sequences linked to a minimal promoter, that can be used in the invention are shown in SEQ ID NO: 8–10. The nucleotide sequences of SEQ ID NOs: 8 and 9 comprise a cytomegalovirus minimal promoter linked to ten tet operator sequences; the two nucleotide sequences differ in the distance between the operators and the first transcribed nucleotide. The nucleotide sequence of SEQ ID NO: 10 comprises a herpes simplex virus minimal tk promoter linked to ten tet operator sequences. The promoter of SEQ ID NO: 8 corresponds to $P_{hCMV}*-1$, described in Gossen, M. and Bujard, H. (1992) *Proc. Natl. Acad. Sci. USA* 89:5547–5551. The promoter of SEQ ID NO: 9 corresponds to $P_{hCMV}*-2$, also described in Gossen, M. and Bujard, H. cited supra.

Alternatively, since regulatory elements have been observed in the art to function downstream of sequences to be transcribed, it is likely that the tet operator sequence(s) can be operatively linked downstream (i.e., 3') of the transcribed nucleotide sequence. Thus, in this configuration, the transcription unit is comprised of, in a 5' to 3' direction: a minimal promoter—a transcribed nucleotide sequence—tet operator sequence(s). Again, it will be appreciated that there is likely to be some flexibility in the permissible distance downstream at which the tet operator sequence(s) can be linked.

The term "tet operator sequence" is intended to encompass all classes of tet operators (e.g., A, B, C, D and E). A nucleotide sequence to be transcribed can be operatively linked to a single tet operator sequence, or for an enhanced range of regulation, it can be operatively linked to multiple tet operator sequences (e.g., two, three, four, five, six, seven, eight, nine, ten or more operator sequences). In a preferred embodiment, the sequence to be transcribed is operatively linked to seven tet operator sequences.

A tet-regulated transcription unit can further be incorporated into a recombinant vector (e.g., a plasmid or viral vector) by standard recombinant DNA techniques. The transcription unit, or recombinant vector in which it is contained, can be introduced into a host cell by standard transfection techniques, such as those described above. It should be appreciated that, after introduction of the transcription unit into a population of host cells, it may be necessary to select a host cell clone which exhibit low basal expression of the tet operator-linked nucleotide sequence (i.e., selection for a host cell in which the transcription unit has integrated at a site that results in low basal expression of the tet operator-linked nucleotide sequence). Furthermore, a tet-regulated transcription unit can be introduced, by procedures described above, into the genome of a non-human animal at an embryonic stage or into plant cells to create a transgenic or homologous recombinant organism carrying the transcription unit in some or all of its cells. Again, it should be appreciated that it may be necessary to select a transgenic or homologous organism in which there is low basal expression of the tet operator-linked nucleotide sequence in cells of interest.

In one embodiment, the target nucleotide sequence of the tet-regulated transcription unit encodes a protein of interest. Thus, upon induction of transcription of the nucleotide sequence by the transactivator of the invention and translation of the resultant mRNA, the protein of interest is produced in a host cell or animal. Alternatively, the nucleotide sequence to be transcribed can encode for an active RNA molecule, e.g., an antisense RNA molecule or ribozyme. Expression of active RNA molecules in a host cell or animal can be used to regulate functions within the host (e.g., prevent the production of a protein of interest by inhibiting translation of the mRNA encoding the protein).

A transactivator of the invention can be used to regulate transcription of an exogenous nucleotide sequence introduced into the host cell or animal. An "exogenous" nucleotide sequence is a nucleotide sequence which is introduced into the host cell and typically is inserted into the genome of the host. The exogenous nucleotide sequence may not be present elsewhere in the genome of the host (e.g., a foreign nucleotide sequence) or may be an additional copy of a sequence which is present within the genome of the host but which is integrated at a different site in the genome. An exogenous nucleotide sequence to be transcribed and an operatively linked tet operator sequence(s) can be contained within a single nucleic acid molecule which is introduced into the host cell or animal.

Alternatively, a transactivator of the invention can be used to regulate transcription of an endogenous nucleotide sequence to which a tet operator sequence(s) has been linked. An "endogenous" nucleotide sequence is a nucleotide sequence which is present within the genome of the host. An endogenous gene can be operatively linked to a tet operator sequence(s) by homologous recombination between a tetO-containing recombination vector and sequences of the endogeneous gene. For example, a homologous recombination vector can be prepared which includes at least one tet operator sequence and a miminal promoter sequence flanked at its 3' end by sequences representing the coding region of the endogenous gene and flanked at its 5' end by sequences from the upstream region of the endogenous gene by excluding the actual promoter region of the endogenous gene. The flanking sequences are of sufficient length for successful homologous recombination of the vector DNA with the endogenous gene. Preferably, several kilobases of flanking DNA are included in the homologous recombination vector. Upon homologous recombination between the vector DNA and the endogenous gene in a host cell, a region of the endogenous promoter is replaced by the vector DNA containing one or more tet operator sequences operably linked to a minimal promoter. Thus, expression of the endogenous gene is no longer under the control of its endogenous promoter but rather is placed under the control of the tet operator sequence(s) and the minimal promoter.

In another embodiment, tet operator sequences can be inserted elsewhere within an endogenous gene, preferably within a 5' or 3' regulatory region, via homologous recombination to create an endogenous gene whose expression can be regulated by a tetracycline-regulated fusion protein described herein. For example, one or more tetO sequences can be inserted into a promoter or enhancer region of an endogenous gene such that promoter or enhancer function is maintained (i.e., the tetO sequences are introduced into a site of the promoter/enhancer region that is not critical for promoter/enhancer function). Regions within promoters or enhancers which can be altered without loss of promoter/enhancer function are known in the art for many genes or can be determined by standard techniques for analyzing critical regulatory regions. An endogenous gene having tetO sequences inserted into a non-critical regulatory region will retain the ability to be expressed in its normal constitutive and/or tissue-specific manner but, additionally, can be downregulated by a tetracycline-controlled transcriptional inhibitor protein in a controlled manner. For example, constitutive expression of such a modified endogenous gene can be inhibited by in the presence of tetracycline (or analogue) using an inhibitor fusion protein that binds to tetO sequences in the presence of tetracycline (or analogue) (as described in further detail in Section IV and Section VI. Part B. below).

A. Regulation of Expression of tet Operator-Linked Nucleotide Sequences

Expression of a tet operator-linked nucleotide sequences is regulated by a transactivator fusion protein of the invention. Thus, the fusion protein and the target nucleic acid are both present in a host cell or organism. The presence of both the transactivator fusion protein and the target transcription unit in the same host cell or organism can be achieved in a number of different ways. For example, a host cell can be transfected with one nucleic acid of the expression system (e.g., encoding the transactivator fusion protein), stably transfected cells can be selected and then the transfected cells can be re-transfected (also referred to as "supertransfected") with nucleic acid corresponding to the other nucleic acid of the expression system (e.g., the target nucleic acid to be transcribed). Two distinct selectable markers can be used for selection, e.g., uptake of the first nucleic acid can be selected with G418 and uptake of the second nucleic acid can be selected with hygromycin. Alternatively, a single population of cells can be transfected with nucleic acid corresponding to both components of the system. Accordingly, the invention provides a nucleic acid composition comprising:

- a first nucleic acid encoding a fusion protein which activates transcription, the fusion protein comprising a first polypeptide which binds to a tet operator sequence in the presence of tetracycline or a tetracycline analogue operatively linked to a second polypeptide which activates transcription in eukaryotic cells; and
- a second nucleic acid comprising a nucleotide sequence to be transcribed operatively linked to at least one tet operator sequence.

In one embodiment, the two nucleic acids are two separate molecules (e.g., two different vectors). In this case, a host cell is cotransfected with the two nucleic acid molecules or successively transfected first with one nucleic acid molecule and then the other nucleic acid molecule. In another embodiment, the two nucleic acids are linked (i.e., colinear) in the same molecule (e.g., a single vector). In this case, a host cell is transfected with the single nucleic acid molecule.

The host cell may be a cell cultured in vitro or a cell present in vivo (e.g., a cell targeted for gene therapy). The host cell can further be a fertilized oocyte, embryonic stem cell or any other embryonic cell used in the creation of non-human transgenic or homologous recombinant animals. Transgenic or homologous recombinant animals which comprise both nucleic acid components of the expression system can be created by introducing both nucleic acids into the same cells at an embryonic stage, or more preferably, an animal which carries one nucleic acid component of the system in its genome is mated to an animal which carries the other nucleic acid component of the system in its genome. Offspring which have inherited both nucleic acid components can then be identified by standard techniques.

B. Coordinate Regulation of Expression of Two Nucleotide Sequences

In addition to providing a system for the regulated expression of a single transcribed nucleotide sequence, the invention further permits coordinated regulation of the expression of two nucleotide sequences operatively linked to the same tet operator sequence(s). Accordingly, another aspect of the invention pertains to a novel tet-regulated transcription unit for coordinate regulation of two genes. In this transcription unit, the same tet operator sequence(s) regulates the expression of two operatively linked nucleotide sequences that are transcribed in opposite directions from the common tet operator sequence(s). Accordingly, one nucleotide sequence is operatively linked to one side of the tet operator sequence (e.g., the 5' end on the top strand of DNA) and the other nucleotide sequence is operatively linked to the opposite side of the tet operator sequence (e.g., the 3' end on the top strand of DNA). Additionally, it should be understood that each nucleotide sequence to be transcribed includes an operatively linked minimal promoter sequence which is located between the nucleotide sequence to be transcribed and the tet operator sequence(s).

Figure 6:
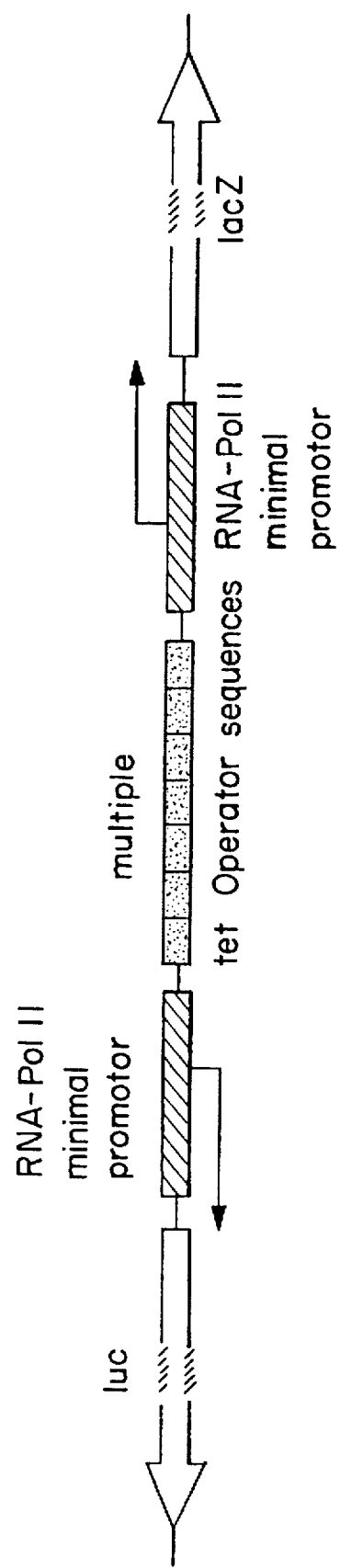
FIG. 6 is a schematic diagram of a bidirectional promoter construct for coordinate regulation of two genes of interest operatively linked to the same tet operators for regulation by a tetracycline-regulated transcriptional activator.

A representative example of such a transcription unit is diagrammed schematically in FIG. 6. In this vectors, the two nucleotide sequences, operatively linked to the same tet operator sequence(s), are transcribed in opposite directions relative to the tet operator sequence(s) (i.e., the sequences are transcribed in a divergent manner upon activation by a transactivator fusion protein of the invention). By "transcribed in opposite directions relative to the tet operator sequence(s)", it is meant that the first nucleotide sequence is transcribed 5' to 3' from one strand of the DNA (e.g., the bottom strand) and the second nucleotide sequence is transcribed 5' to 3' from the other stand of the DNA (e.g., the top strand), resulting in bidirectional transcription away from the tet operator sequence(s).

Accordingly, the invention provides a recombinant vector for coordinately-regulated, bidirectional transcription of two nucleotide sequence. In one embodiment, the vector comprises a nucleotide sequence linked by phosphodiester bonds comprising, in a 5' to 3' direction:

a first nucleotide sequence to be transcribed, operatively linked to at least one tet operator sequence, operatively linked to a second nucleotide sequence to be transcribed, wherein transcription of the first and second nucleotide sequences proceeds in opposite directions from the at least one tet operator sequence(s) (i.e., the first and second nucleotide sequences are transcribed in a divergent manner).

In another embodiment, the vector does not include the first and second nucleotide sequence to be transcribed but instead contains cloning sites which allow for the introduction into the vector of nucleotide sequences of interest. Accordingly, in this embodiment, the vector comprises a nucleotide sequence comprising in a 5' to 3' direction:

a first cloning site for introduction of a first nucleotide sequence to be transcribed, operatively linked to at least one tet operator sequence, operatively linked to a second cloning site for introduction of a second nucleotide sequence to be transcribed, wherein transcription of a first and second nucleotide sequence introduced into the vector proceeds in opposite directions from the at least one tet operator sequence(s). It will be appreciated by those skilled in the art that this type of "cloning vector" may be in a form which also includes minimal promoter sequences such that a first nucleotide sequence introduced into the first cloning site is operatively linked to a first minimal promoter and a second nucleotide sequence introduced into the second cloning site is operatively linked to a second minimal promoter. Alternatively, the "cloning vector" may be in a form which does not include minimal promoter sequences and instead, nucleotide sequences including linked minimal promoter sequences are introduced into the cloning sites of the vector.

The term "cloning site" is intended to encompass at least one restriction endonuclease site. Typically, multiple different restriction endonuclease sites (e.g., a polylinker) are contained within the nucleic acid.

In yet another embodiment, the vector for coordinate, bidirectional transcription of two nucleotide sequences may contain a first nucleotide to be transcribed, such as that encoding a detectable marker (e.g., luciferase or β-galactosidase), and a cloning site for introduction of a second nucleotide sequence of interest.

Figure 7B:
FIG. 7B (SEQ ID NO: 7) shows the nucleotide sequence of a bidirectional promoter region for coordinate regulation of two genes of interest by a tetracycline-regulated transcriptional activator.

The nucleotide sequences of two different suitable bidirectional promoter regions for use in a vector for coordinate regulation of two nucleotide sequences to be transcribed, as described herein, are shown in FIGS. 7A and 7B (SEQ ID NOS: 6 and 7, respectively). In the construct of FIG. 7A, both minimal promoters present in the construct are derived from a CMV promoter. In the construct of FIG. 7B, one minimal promoter present in the construct is derived from a CMV promoter, whereas the second minimal promoter is derived from a TK promoter. A plasmid pUHDG1316-8, comprising a bidirectional promoter of the invention, has been deposited on July 8, 1994 under the provisions of the Budapest Treaty at the Deutsche Sammlung Von Mikroorganismen und ZellKulturen GmbH (DSM) in Braunschweig, Germany and assigned deposit number DSM 9281.

The transcription unit of the invention for bidirectional transcription of two nucleotide sequences operatively linked to the same tet operator sequence(s) is useful for coordinating the expression of the two nucleotide sequences of interest. Preferably, at least one of the nucleotide sequences to be transcribed is a eukaryotic nucleotide sequence. In one application, the vector is used to produce stoichiometric amounts of two subunits of a heterodimeric molecule in the same cell. For example, the vector can be used produce antibody heavy and light chains in the same cell or to produce growth factor receptor subunits in the same cells. In another application, the vector is used to express two gene products that cooperate in establishing a particular cellular phenotype. In yet another application, the vector is used to coexpress an indicator function and a gene of interest, wherein the indicator is utilized to monitor expression of the gene of interest. Thus, one of the two coordinately expressed sequences can encode a gene of interest and the other can encode a detectable marker, such as a surface marker or enzyme (e.g., β-galactosidase or luciferase) which is used for selection of cells expressing the gene of interest.

Transcription of the two coordinately-regulated nucleotide sequences can be induced by tetracycline (or an analogue thereof) by use of the Tc-inducible transcriptional activator of the invention to regulate expression of the two nucleotide sequences. Thus, in this system, expression of both nucleotide sequences is "off" in the absence of Tc (or analogue), whereas expression is turned "on" by the presence of Tc (or analogue). Alternatively, the vector for coordinate regulation of two nucleotide sequences can be used in conjunction with other tetracycline-regulated transcription factors known in the art. For example, a transactivator fusion protein of a wild-type Tet repressor fused to a transcriptional activation domain, which activates gene expression in the absence of Tc (or analogue), such as the tTA described in Gossen, M. and Bujard, H. (1992) *Proc. Natl. Acad. Sci. USA* 89:5547–5551, can also be used in conjunction with this target transcription unit for coordinate regulation.

C. Independent Regulation of Expression of Multiple Nucleotide Sequences

The invention still further permits independent and opposite regulation of two or more nucleotide sequences to be transcribed. Accordingly, another aspect of the invention pertains to a novel tet-regulated transcription unit for independent regulation of two or more genes. To independently regulate the expression of two nucleotide sequences to be transcribed, one nucleotide sequence is operatively linked to a tet operator sequence(s) of one class type and the other nucleotide sequence is operatively linked to a tet operator sequence(s) of another class type. Accordingly, the invention provides at least one recombinant vector for independent regulation of transcription of two nucleotide sequences. In one embodiment, the vector(s) comprises:

a first nucleotide sequence to be a transcribed operatively linked to at least one tet operator sequence of a first class type; and a second nucleotide sequence to be a transcribed operatively linked to at least one tet operator sequence of a second class type.

(It should be understood that each nucleotide sequence to be transcribed also includes an operatively linked, upstream minimal promoter sequence.) The two independently regulated transcription units can be included on a single vector, or alternatively, on two separate vectors. The recombinant vector(s) containing the nucleotide sequences to be transcribed can be introduced into a host cell or animal as described previously.

In another embodiment, the vector(s) does not include the first and second nucleotide sequence to be transcribed but instead contains cloning sites which allow for the introduction into the vector of nucleotide sequences of interest. Accordingly, in this embodiment, the vector(s) comprises:

a first cloning site for introduction of a first nucleotide sequence to be transcribed operatively linked to at least one tet operator sequence of a first class type; and a second cloning site for introduction of a second nucleotide sequence to be transcribed operatively linked to at least one tet operator sequence of a second class type.

This cloning vector(s) may be in a form that already includes first and second minimal promoters operatively linked, respectively, to the first and second cloning sites. Alternatively, nucleotide sequences to be transcribed which include an operatively linked minimal promoter can be introduced into the cloning vector.

In yet another embodiment, the vector for independent regulation of two nucleotide sequences may contain a first nucleotide to be transcribed, such as that encoding a detectable marker or a suicide gene, operatively linked to at least one tet operator sequence of a first class type and a cloning site for introduction of a second nucleotide sequence of interest such that it is operatively linked to at least one tet operator sequence of a second class type.

It will be appreciated by those skilled in the art that various combinations of classes of tet operator sequences can be used for independent regulation of two nucleotide sequences. For example, the first tet operator sequence(s) can be of the class A type and the second can be of the class B type, or the first tet operator sequence can be of the class B type and the second can be of the class C type, etc. Preferably, one to the two tet operators used is a class B type operator.

Independent transcription of the first and second nucleotide sequences is regulated in a host cell by further introducing into the host cell one or more nucleic acids encoding two different transactivator fusion proteins which bind independently to tet operator sequences of different class types. The first fusion protein comprises a polypeptide which binds to a tet operator sequence in the presence of tetracycline or a tetracycline analogue, operatively linked to a polypeptide which activates transcription in eukaryotic cells (e.g., a transactivator fusion protein of the invention, such as a mutated Tn10-derived Tet repressor linked to a VP16 activation region). The second fusion protein comprises a polypeptide which binds to a tet operator sequence in the absence of tetracycline or a tetracycline analogue, operatively linked to a polypeptide which activates transcription in eukaryotic cells (e.g., a wild-type Tn10-derived Tet repressor linked to a VP16 activation region, such as the tTA described in Gossen, M. and Bujard, H. (1992) *Proc. Natl. Acad. Sci. USA* 89:5547–5551). In one embodiment, the first fusion protein binds to the tet operator sequence of the first class type used in the transcription unit and the second fusion protein binds to the tet operator sequence of the second class type used in the transcription unit. Alternatively, in another embodiment, the first fusion protein binds to the second class type of tet operator and the second fusion protein binds to the first class type of tet operator.

For example, the first nucleotide sequence to be transcribed may be linked to a class A tet operator and the first fusion protein may bind to class A operators, whereas the second nucleotide sequence to be transcribed may be linked to a class B tet operator and the second fusion protein may bind to class B operators. Thus, in this embodiment, transcription of the first nucleotide sequence is activated in the presence of Tc (or analogue thereof) while transcription of the second nucleotide sequence is activated in the absence of Tc (or analogue thereof). Alternatively, in another embodiment, the first fusion protein binds to class B operators and the second fusion protein binds to class A operators. In this case, transcription of the second nucleotide sequence is activated in the presence of Tc (or analogue thereof) while transcription of the first nucleotide sequence is activated in the absence of Tc (or analogue thereof). Appropriate transactivator proteins for use in this system can be designed as described above in Section I and in Gossen and Bujard (1992) cited supra. In order to inhibit heterodimerization between the two different types of Tet repressor fusion proteins present in the same cell, it may be necessary to mutate the dimerization region of one or both of the transactivator fusion proteins. Mutations can be targeted to the C-terminal region of TetR known to be involved in dimerization. The dimerization region has been described in detail based upon the crystal structure of TetR (see Hinrichs, W. et al. (1994) *Science* 264:418–420).

This system allows for independent and opposite regulation of the expression of two genes by Tc and analogues thereof. Use of different Tc analogues as inducing agents may further allow for high, low or intermediate levels of expression of the different sequences (discussed in greater detail in Section V below). The novel transcription unit of the invention for independently regulating the expression of two genes, described above, can be used in situations where two gene products are to be expressed in the same cell but where it is desirable to express one gene product while expression of the other gene product is turned "off", and vice versa. For example, this system is particularly useful for expressing in the same host cell either a therapeutic gene or a suicide gene (i.e., a gene which encodes a product that can be used to destroy the cell, such as ricin or herpes simplex virus thymidine kinase). In many gene therapy situations, it is desirable to be able to express a gene for therapeutic purposes in a host cell but also to have the capacity to destroy the host cell once the therapy is completed. This can be accomplished using the above-described system by linking the therapeutic gene to one class of tet operator and the suicide gene to another class of tet operator. Thus, expression of the therapeutic gene in a host cell can be stimulated by Tc (in which case expression of the suicide gene is absent). Then, once the therapy is complete, Tc is removed, which turns off expression of the therapeutic gene and turns on expression of the suicide gene in the cell.

D. Combined Coordinate and Independent Regulation of Multiple Nucleotide Sequences It is further possible to regulate the expression of four nucleotide sequences by combining the system described in Section IIIB with the system described in Section IIIC such that two pairs of sequences are coordinately regulated while one pair is independently regulated from the other pair. Accordingly, two target transcription units can be designed comprising:

- a first nucleic acid comprising in a 5' to 3' direction: a first nucleotide sequence to be transcribed, a tet operator sequence(s) of a first class type, and a second nucleotide sequence to be transcribed
- a second nucleic acid comprising in a 5' to 3' direction: a third nucleotide sequence to be transcribed, a tet operator sequence(s) of a second class type, and a fourth nucleotide sequence to be transcribed.

Transcription of the first and second nucleotide sequences in the first nucleic acid proceeds in a divergent manner from the first class of tet operator sequence(s). Likewise, transcription of the third and fourth nucleotide sequences in the second nucleic acid proceeds in a divergent manner from the second class of tet operator sequence(s). Thus, expression of the first and second nucleotide sequences is coordinately regulated and expression of the third and fourth nucleotide sequences is coordinately regulated. However, expression of the first and second sequences is independently (and oppositely) regulated compared to the third and fourth sequences through the use of two different transactivator fusion proteins, as described above, one which activates transcription in the presence of Tc (or analogue thereof) and the other which activates transcription in the absence of Tc (or analogue thereof). One transactivator is designed to bind to a tet operators of the first class type and the other is designed to bind to a tet operators of the second class type. In other embodiments, rather than already containing first, second, third and/or fourth nucleotide sequences to be transcribed, these transcription units can contain cloning sites which allow for the introduction of first, second, third and/or fourth nucleotide sequences to be transcribed.

IV. Tetracycline-Regulated Transcriptional Inhibitors

Another aspect of the invention pertains to transcriptional inhibitor fusion proteins. The inhibitor fusion proteins of the invention are constructed similarly to the transactivator fusion proteins of the invention (see Section I above) but instead of containing a polypeptide domain that stimulates transcription in eukaryotic cells, the inhibitor fusion proteins contain a polypeptide domain that inhibits transcription in eukaryotic cells. The inhibitor fusion proteins are used to downregulate the expression of genes operably linked to tetO sequences. For example, when a tetO-linked gene is introduced into a host cell or animal, the level of basal, constitutive expression of the gene may vary depending upon the type of cell or tissue in which the gene is introduced and on the site of integration of the gene. Alternatively, constitutive expression of endogenous genes into which tetO sequences have been introduced may vary depending upon the strength of additional endogenous regulatory sequences in the vicinity. The inhibitor fusion proteins described herein provide compositions that can be used to inhibit the expression of such tetO-linked genes in a controlled manner.

In one embodiment, the inhibitor fusion protein of the invention comprises a first polypeptide that binds to tet operator sequences in the absence, but not the presence, of tetracycline (Tc) or an analogue thereof operatively linked to a heterologous second polypeptide that inhibits transcription in eukaryotic cells. In another embodiment, the inhibitor fusion protein comprises a first polypeptide that binds to tet operator sequences in the presence, but not the absence, of tetracycline operatively linked to a heterologous second polypeptide that inhibits transcription in eukaryotic cells. The term "heterologous" is intended to mean that the second polypeptide is derived from a different protein than the first polypeptide. Like the transactivator fusion proteins, the transcriptional inhibitor fusion proteins can be prepared using standard recombinant DNA techniques as described herein.

A. The first polypeptide of the transcriptional inhibitor fusion protein

The transcriptional inhibitor fusion protein of the invention is composed, in part, of a first polypeptide which binds to a tet operator sequence either (i) in the absence, but not the presence of tetracycline (Tc), or an analogue thereof, or alternatively, (ii) in the presence, but not the absence of Tc or an analogue thereof.

Preferably, in the former embodiment, the first polypeptide is a wild-type Tet repressor (which binds to tet operator sequences in the absence but not the presence of Tc). A wild-type Tet repressor of any class (e.g., A, B, C, D or E) may be used as the first polypeptide. Preferably, the wild-type Tet repressor is a Tn10-derived Tet repressor. The nucleotide and amino acid sequences of a wild-type Tn10-derived Tet repressor are shown in SEQ ID NO: 16 and SEQ ID NO: 17, respectively.

Alternatively, in the latter embodiment, the first polypeptide is a mutated Tet repressor as described in Section I, part A above (which binds to tet operator sequences in the presence but not the absence of Tc). A mutated Tet repressor of any class (e.g., A, B, C, D or E) may be used as the first polypeptide. Preferably, the mutated Tet repressor is a Tn10-derived Tet repressor having one or more amino acid substitutions at positions 71, 95, 101 and/or 102. The nucleotide and amino acid sequences of such a mutated Tn10-derived Tet repressor are shown in SEQ ID NO: 18 and SEQ ID NO: 19, respectively.

B. The second polypeptide of the transcriptional inhibitor fusion protein

The first polypeptide of the transcriptional inhibitor fusion protein is operatively linked to a second polypeptide which directly or indirectly inhibits transcription in eukaryotic cells. As described in Section I, above, to operatively link the first and second polypeptides of a fusion protein, typically nucleotide sequences encoding the first and second polypeptides are ligated to each other in-frame to create a chimeric gene encoding the fusion protein. However, the first and second polypeptides can be operatively linked by other means that preserve the function of each polypeptide (e.g., chemically crosslinked). Although the fusion proteins are typically described herein as having the first polypeptide at the amino-terminal end of the fusion protein and the second polypeptide at the carboxy-terminal end of the fusion protein, it will be appreciated by those skilled in the art that the opposite orientation (i.e., the second polypeptide at the amino-terminal end and the first polypeptide at the carboxy-terminal end) is also contemplated by the invention.

Proteins and polypeptide domains within proteins which can function to inhibit transcription in eukaryotic cells have been described in the art (for reviews see, e.g., Renkawitz, R. (1990) *Trends in Genetics* 6:192–197; and Herschbach, B. M. and Johnson, A. D. (1993) *Annu. Rev. Cell. Biol.* 9:479–509). Such transcriptional inhibitor domains have been referred to in the art as "silencing domains" or "repressor domains." Although the precise mechanism by which many of these polypeptide domains inhibit transcription is not known (and the invention is not intended to be limited by mechanism), there are several possible means by which repressor domains may inhibit transcription, including: 1) competitive inhibition of binding of either activator proteins or the general transcriptional machinery, 2) prevention of the activity of a DNA bound activator and 3) negative interference with the assembly of a functional preinitiation complex of the general transcription machinery. Thus, a repressor domain may have a direct inhibitory effect on the transcriptional machinery or may inhibit transcription indirectly by inhibiting the activity of activator proteins. Accordingly, the term "a polypeptide that inhibits transcription in eukaryotic cells" as used herein is intended to include polypeptides which act either directly or indirectly to inhibit transcription. As used herein, "inhibition" of transcription is intended to mean a diminution in the level or amount of transcription of a target gene compared to the level or amount of transcription prior to regulation by the transcriptional inhibitor protein. Transcriptional inhibition may be partial or complete. The terms "silencer", "repressor" and "inhibitor" are used interchangeably herein to describe a regulatory protein, or domains thereof, that can inhibit transcription.

A transcriptional "repressor" or "silencer" domain as described herein is a polypeptide domain that retains its transcriptional repressor function when the domain is transferred to a heterologous protein. Proteins which have been demonstrated to have repressor domains that can function when transferred to a heterologous protein include the v-erbA oncogene product (Baniahmad, A. et al. (1992) *EMBO J.* 11:1015–1023), the thyroid hormone receptor (Baniahmad, supra), the retinoic acid receptor (Baniahmad, supra), and the Drosophila Krueppel (Kr) protein (Licht, J. D. et al. (1990) *Nature* 346:76–79; Sauer, F. and Jackle, H. (1991) *Nature* 3:563–566; Licht, J. D. et al. (1994) *Mol. Cell. Biol.* 14:4057–4066). Non-limiting examples of other proteins which have transcriptional repressor activity in eukaryotic cells include the Drosophila homeodomain protein even-skipped (eve), the *S. cerevisiae* Ssn6/Tup1 protein complex (see Herschbach and Johnson, supra), the yeast SIR1 protein (see Chien, et al. (1993) *Cell* 75:531–541), NeP1 (see Kohne, et al. (1993) *J. Mol. Biol.* 232:747–755), the Drosophila dorsal protein (see Kirov, et al. (1994) *Mol. Cell. Biol.* 14:713–722; Jiang, et al. (1993) *EMBO J.* 12:3201–3209), TSF3 (see Chen, et al. (1993) *Mol. Cell. Biol.* 13:831–840), SF1 (see Targa, et al. (1992) *Biochem. Biophys. Res. Comm.* 188:416–423), the Drosophila hunchback protein (see Zhang, et al. (1992) *Proc. Natl. Acad. Sci. USA* 89:7511–7515), the Drosophila knirps protein (see Gerwin, et al. (1994) *Mol. Cell. Biol.* 14:7899–7908), the WT1 protein (Wilm's tumor gene product) (see Anant, et al. (1994) *Oncogene* 9:3113–3126; Madden et al., (1993) *Oncogene* 8:1713–1720), Oct-2.1 (see Lillycrop, et al. (1994) *Mol. Cell. Biol.* 14:7633–7642), the Drosophila engrailed protein (see Badiani, et al. (1994) *Genes Dev.* 8:770–782; Han and Manley, (1993) *EMBO J.* 12:2723–2733), E4BP4 (see Cowell and Hurst, (1994) *Nucleic Acids Res.* 22:59–65) and ZF5 (see Numoto, et al. (1993) *Nucleic Acids Res.* 21:3767–3775).

In a preferred embodiment, the second polypeptide of the transcriptional inhibitor fusion protein of the invention is a transcriptional silencer domain of the Drosophila Krueppel protein. A C-terminal region having repressor activity can be used, such as amino acids 403–466 of the native protein (see Sauer, F. and Jackle, H., supra). This region is referred to as C64KR. The nucleotide and amino acid sequences of C64KR are shown in SEQ ID NO: 20 and SEQ ID NO: 21, respectively. Construction of an expression vector encoding a TetR-C64KR fusion protein is described in Example 4. Alternatively, an alanine-rich amino terminal region of Kr that also has repressor activity can be used as the second polypeptide of the fusion protein. For example, amino acids 26–110 of Kr (see Licht, J. D. et al., (1990) supra) can be used as the second polypeptide. Alternatively, shorter or longer polypeptide fragments encompassing either of the Kr silencer domains that still retain full or partial inhibitor activity are also contemplated (e.g., amino acids 62 to 92 of the N-terminal silencer domain; see Licht, et al. (1994) supra).

In another preferred embodiment, the second polypeptide of the transcriptional inhibitor fusion protein of the invention is a transcriptional silencer domain of the v-erbA oncogene product. The silencer domain of v-erbA has been mapped to approximately amino acid residues 362–632 of the native v-erbA oncogene product (see Baniahmad, et al. supra). Accordingly, a fragment encompassing this region is used as the second polypeptide of the silencer domain. In one embodiment, amino acid residues 364–635 of the native v-erbA protein are used. The nucleotide and amino acid sequences of this region of v-erbA are shown in SEQ ID NO: 22 and SEQ ID NO: 23, respectively. Construction of an expression vector encoding a TetR-v-erbA fusion protein is described in Example 5. Alternatively, shorter or longer polypeptide fragments encompassing the v-erbA silencer region that still retain full or partial inhibitor activity are also contemplated. For example, a.a. residues 346– 639, 362–639, 346–632, 346–616 and 362–616 of v-erbA may be used. Additionally, polypeptide fragments encompassing these regions that have internal deletions yet still retain fall or partial inhibitor activity are encompassed by the invention, such as a.a. residues 362–468/508–639 of v-erbA. Furthermore, two or more copies of the silencer domain may be included in the fusion protein, such as two copies of a.a. residues 362–616 of v-erbA. Suitable silencer polypeptide domains of v-erbA are described further in Baniahmad, A. et al. (supra).

In other embodiments, other silencer domains are used. Non-limiting examples of polypeptide domains that can be used include: amino acid residues 120–410 of the thyroid hormone receptor alpha (THRα), amino acid residues 143–403 of the retinoic acid receptor alpha (RARα), amino acid residues 186–232 of knirps, the N-terminal region of WT 1 (see Anant, supra), the N-terminal region of Oct-2.1 (see Lillycrop, supra), a 65 amino acid domain of E4BP4 (see Cowell and Hurst, supra) and the N-terminal zinc finger domain of ZF5 (see Numoto, supra). Moreover, shorter or longer polypeptide fragments encompassing these regions that still retain full or partial inhibitor activity are also contemplated.

In addition to previously described transcriptional inhibitor domains, novel transcriptional inhibitor domains, which can be identified by standard techniques, are within the scope of the invention. The transcriptional inhibitor ability of a polypeptide can be assayed by: 1) constructing an expression vector that encodes the test silencer polypeptide linked to another polypeptide having DNA binding activity (i.e., constructing a DNA binding domain-silencer domain fusion protein), 2) cotransfecting this expression vector into host cells together with a reporter gene construct that is normally constitutively expressed in the host cell and also contains binding sites for the DNA binding domain and 3) determining the amount of transcription of the reporter gene construct that is inhibited by expression of the fusion protein in the host cell. For example, a standard assay used in the art utilizes a fusion protein of a GAL4 DNA binding domain (e.g., amino acid residues 1–147) and a test silencer domain. This fusion protein is then used to inhibit expression of a reporter gene construct that contains positive regulatory sequences (that normally stimulate constitutive transcription) and GAL4 binding sites (see e.g., Baniahmad, supra).

C. A third polypeptide of the transcriptional inhibitor fusion protein

In addition to a Tet repressor and a transcriptional silencer domain, a transcriptional inhibitor fusion protein of the invention can contain an operatively linked third polypeptide which promotes transport of the fusion protein to a cell nucleus. As described for the transactivator fusion proteins (see Section I, Part C, above), a nuclear localization signal can be incorporated into the transcriptional inhibitor fusion protein.

D. Expression of the transcriptional inhibitor fusion protein

A nucleic acid molecule encoding a transcriptional inhibitor fusion protein of the invention can be incorporated into a recombinant expression vector and introduced into a host cell to express the fusion protein in the host cell as described in Section II, Parts A, B and C, above. Preferably, a host cell expressing a transcriptional inhibitor fusion protein of the invention also carries a tet operator-linked gene of interest (i.e., target nucleotide sequence to be transcribed).

Transgenic organisms expressing a transcriptional inhibitor fusion protein in cells thereof can be prepared as described in Section II, Part D, above. Moreover, homologous recombinant organisms expressing a transcriptional inhibitor fusion protein in cells thereof are also encompassed by the invention and can be prepared as described in Section II, Part E, above. The invention provides recombinant expression vectors suitable for homologous recombination. In one embodiment, such an expression vector comprises a nucleic acid molecule encoding a transcriptional inhibitor fusion protein of the invention which is flanked at its 5' and 3' ends by additional nucleic acid of a eukaryotic gene, the additional nucleic acid being of sufficient length for successful homologous recombination with the eukaryotic gene. Vectors and methods for creating homologous recombinant organisms that express the components of the regulatory system of the invention, and uses therefor, are described in further detail in U.S. patent application Ser. No. 08/260,452. Preferably, a transgenic or homologous recombinant organism of the invention expressing a transcriptional inhibitor fusion protein in cells thereof also carries a tet operator-linked gene of interest (i.e., target nucleotide sequence to be transcribed) in cells thereof.

V. Kits of the Invention

Another aspect of the invention pertains to kits which include the components of the inducible regulatory system of the invention. Such a kit can be used to regulate the expression of a gene of interest (i.e., a nucleotide sequence of interest to be transcribed) which can be cloned into a target transcription unit. The kit may include nucleic acid encoding a transcriptional activator fusion protein or a transcriptional inhibitor fusion protein or both. Alternatively, eukaryotic cells which have nucleic acid encoding a transactivator and/or inhibitor fusion protein stably incorporated therein, such that the transactivator and/or inhibitor fusion protein are expressed in the eukaryotic cell, may be provided in the kit.

In one embodiment, the kit includes a carrier means having in close confinement therein at least two container means: a first container means which contains a first nucleic acid (e.g., DNA) encoding a transactivator fusion protein of the invention (e.g., a recombinant expression vector encoding a first polypeptide which binds to a tet operator sequence in the presence of tetracycline operatively linked to a second polypeptide which activates transcription in eukaryotic cells), and a second container means which contains a second target nucleic acid (e.g., DNA) for the transactivator into which a nucleotide sequence of interest can be cloned. The second nucleic acid typically comprises a cloning site for introduction of a nucleotide sequence to be transcribed (optionally including an operatively linked minimal promoter sequence) and at least one operatively linked tet operator sequence.

The term "cloning site" is intended to encompass at least one restriction endonuclease site. Typically, multiple different restriction endonuclease sites (e.g., a polylinker) are contained within the nucleic acid.

To regulate expression of a nucleotide sequence of interest using the components of the kit, the nucleotide sequence is cloned into the cloning site of the target vector of the kit by conventional recombinant DNA techniques and then the first and second nucleic acids are introduced into a host cell or animal. The transactivator fusion protein expressed in the host cell or animal then regulates transcription of the nucleotide sequence of interest in the presence of the inducing agent (Tc or analogue thereof).

Alternatively, in another embodiment, the kit includes a eukaryotic cell which is stably transfected with a nucleic acid encoding a transactivator fusion protein of the invention such that the transactivator is expressed in the cell. Thus, rather than containing nucleic acid alone, the first container means described above can contain a eukaryotic cell line into which the first nucleic acid encoding the transactivator has been stably introduced (e.g., by stable transfection by a conventional method such as calcium phosphate precipitation or electroporation, etc.). In this embodiment, a nucleotide sequence of interest is cloned into the cloning site of the target vector of the kit and then the target vector is introduced into the eukaryotic cell expressing the transactivator fusion protein.

Alternatively or additionally, a recombinant vector of the invention for coordinate regulation of expression of two nucleotide sequences can also be incorporated into a kit of the invention. The vector can be included in the kit in a form that allows for introduction into the vector of two nucleotide sequences of interest. Thus, in another embodiment, a kit of the invention includes 1) a first nucleic acid encoding a transactivator fusion protein of the invention (or a eukaryotic cell into which the nucleic acid has been stably introduced) and 2) a second nucleic acid comprising a nucleotide sequence comprising in a 5' to 3' direction: a first cloning site for introduction of a first nucleotide sequence of interest operatively linked to at least one tet operator sequence operatively linked to a second cloning site for introduction of a second nucleotide sequence of interest, wherein transcription of the first and second nucleotide sequences proceeds in opposite directions from the at least one tet operator sequence. Optionally, the vector can include operatively linked minimal promoter sequences.

In another embodiment, the vector can be in a form that already contains one nucleotide sequence to be transcribed (e.g., encoding a detectable marker such as luciferase, β-galactosidase or CAT) and a cloning site for introduction of a second nucleotide sequence of interest to be transcribed.

The transcription units and transactivators of the invention for independent regulation of expression of two nucleotide sequences to be transcribed can also be incorporated into a kit of the invention. The target transcription units can be in a form which allows for introduction into the transcription units of nucleotide sequences of interest to be transcribed. Thus, in another embodiment, a kit of the invention includes 1) a first nucleic acid encoding a transactivator which binds to a tet operator of a first class type in the presence of Tc or an analogue thereof, 2) a second nucleic acid comprising a first cloning site for introduction of a first nucleotide sequence to be transcribed operatively linked to at least one tet operator of a first class type, 3) a third nucleic acid encoding a transactivator which binds to a tet operator of a second class type in the absence of Tc or an analogue thereof, , and 4) a fourth nucleic acid comprising a second cloning site for introduction of a second nucleotide sequence to be transcribed operatively linked to at least one tet operator of a second class type. (Optionally, minimal promoter sequences are included in the second and fourth nucleic acids). In another embodiment, one nucleotide sequence to be transcribed (e.g., encoding a suicide gene) is already contained in either the second or the fourth nucleic acid. In yet another embodiment, the nucleic acids encoding the transactivators (e.g., the first and third nucleic acids described above) can be stably introduced into a eukaryotic cell line which is provided in the kit.

In yet another embodiment, a kit of the invention includes a first container means containing a first nucleic acid encoding a transcriptional inhibitor fusion protein of the invention (e.g., the fusion protein inhibits transcription in eukaryotic cells either only in the presence of Tc or only the absence of Tc) and a second container means containing a second nucleic acid comprising a cloning site for introduction of a nucleotide sequence to be transcribed operatively linked to at least one tet operator sequence. The kit may further include a third nucleic acid encoding a transactivator fusion protein that binds to tetO sequences either only in the presence of Tc or only in the absence of Tc. Alternatively, the first and/or third nucleic acids (i.e., encoding the inhibitor or transactivator fusion proteins) may be stably incorporated into a eukaryotic host cell which is provided in the kit.

In still another embodiment, a kit of the invention may include at least one tetracycline or tetracycline analogue. For example, the kit may include a container means which contains tetracycline, anhydrotetracycline, doxycycline, epioxytetracycline or other tetracycline analogue described herein.

VI. Regulation of Gene Expression by Tetracycline or Analogues Thereof

A. Stimulation of Gene Expression by Transactivator Fusion Proteins

In a host cell which carries nucleic acid encoding a transactivator fusion protein of the invention and a nucleotide sequence operatively linked to the tet operator sequence(i.e., gene of interest to be transcribed), high level transcription of the nucleotide sequence operatively linked to the tet operator sequence(s) does not occur in the absence of the inducing agent, tetracycline or analogues thereof. The level of basal transcription of the nucleotide sequence may vary depending upon the host cell and site of integration of the sequence, but is generally quite low or even undetectable in the absence of Tc. In order to induce transcription in a host cell, the host cell is contacted with tetracycline or a tetracycline analogue. Accordingly, another aspect of the invention pertains to methods for stimulating transcription of a nucleotide sequence operatively linked to a tet operator sequence in a host cell or animal which expresses a transactivator fusion protein of the invention. The methods involve contacting the cell with tetracycline or a tetracycline analogue or administering tetracycline or a tetracycline analogue to a subject containing the cell.

The term "tetracycline analogue" is intended to include compounds which are structurally related to tetracycline and which bind to the Tet repressor with a $K_a$ of at least about $10^6 M^{-1}$. Preferably, the tetracycline analogue binds with an affinity of about $10^9 M^{-1}$ or greater. Examples of such tetracycline analogues include, but are not limited to, anhydrotetracycline, doxycycline, chlorotetracycline, oxytetracycline and others disclosed by Hlavka and Boothe, "The Tetracyclines," in *Handbook of Experimental Pharmacology* 78, R. K. Blackwood et al. (eds.), Springer-Verlag, Berlin-New York, 1985; L. A. Mitscher, "The Chemistry of the Tetracycline Antibiotics", *Medicinal Research* 9, Dekker, New York, 1978; Noyee Development Corporation, "Tetracycline Manufacturing Processes" *Chemical Process Reviews*, Park Ridge, N.J., 2 volumes, 1969; R. C. Evans, "The Technology of the Tetracyclines", *Biochemical Reference Series* 1, Quadrangle Press, New York, 1968; and H. F. Dowling, "Tetracycline", *Antibiotic Monographs*, no. 3, Medical Encyclopedia, New York, 1955. Preferred Tc analogues for high level stimulation of transcription are anhydrotetracycline and doxycycline. A Tc analogue can be chosen which has reduced antibiotic activity compared to Tc. Examples of such Tc analogues are anhydrotetracycline and epioxytetracycline.

To induce gene expression in a cell in vitro, the cell is contacted with Tc or a Tc analogue by culturing the cell in a medium containing the compound. When culturing cells in vitro in the presence of Tc or Tc analogue, a preferred concentration range for the inducing agent is between about 10 and about 1000 ng/ml. Tc or a Tc analogue can be directly added to media in which cells are already being cultured, or more preferably for high levels of gene induction, cells are harvested from Tc-free media and cultured in fresh media containing Tc, or an analogue thereof.

To induce gene expression in vivo, cells within in a subject are contacted with Tc or a Tc analogue by administering the compound to the subject. The term "subject" is intended to include humans and other non-human mammals including monkeys, cows, goats, sheep, dogs, cats, rabbits, rats, mice, and transgenic and homologous recombinant species thereof. Furthermore, the term "subject" is intended to include plants, such as transgenic plants. When the inducing agent is administered to a human or animal subject, the dosage is adjusted to preferably achieve a serum concentration between about 0.05 and 1.0 µg/ml. Tc or a Tc analogue can be administered to a subject by any means effective for achieving an in vivo concentration sufficient for gene induction. Examples of suitable modes of administration include oral administration (e.g., dissolving the inducing agent in the drinking water), slow release pellets and implantation of a diffusion pump. To administer Tc or a Tc analogue to a transgenic plant, the inducing agent can be dissolved in water administered to the plant.

The ability to use different Tc analogues as inducing agents in this system allows for modulate the level of expression of a tet operator-linked nucleotide sequence. As demonstrated in Example 2, anhydrotetracycline and doxycycline have been found to be strong inducing agents. The increase in transcription of the target sequence is typically as high as 1000- to 2000-fold, and induction factors as high as 20,000 fold can be achieved. Tetracycline, chlorotetracycline and oxytetracycline have been found to be weaker inducing agents, i.e., the increase in transcription of a target sequence is in the range of about 10-fold. Thus, an appropriate tetracycline analogue is chosen as an inducing agent based upon the desired level of induction of gene expression. It is also possible to change the level of gene expression in a host cell or animal over time by changing the Tc analogue used as the inducing agent. For example, there may be situations where it is desirable to have a strong burst of gene expression initially and then have a sustained lower level of gene expression. Accordingly, an analogue which stimulates a high levels of transcription can be used initially as the inducing agent and then the inducing agent can be switched to an analogue which stimulates a lower level of transcription. Moreover, when regulating the expression of multiple nucleotide sequences (e.g., when one sequence is regulated by a one of class tet operator sequence(s) and the other is regulated by another class of tet operator sequence(s), as described above in Section III, Part C, above), it may be possible to independently vary the level of expression of each sequence depending upon which transactivator fusion protein is used to regulate transcription and which Tc analogue(s) is used as the inducing agent. Different transactivator fusion proteins are likely to exhibit different levels of responsiveness to Tc analogues. The level of induction of gene expression by a particular combination of transactivator fusion protein and inducing agent (Tc or Tc analogue) can be determined by techniques described herein, (e.g., see Example 2). Additionally, the level of gene expression can be modulated by varying the concentration of the inducing agent. Thus, the expression system of the invention provides a mechanism not only for turning gene expression on or off, but also for "fine tuning" the level of gene expression at intermediate levels depending upon the type and concentration of inducing agent used.

B. Inhibition of Gene Expression by Transcriptional Inhibitor Fusion Proteins

The invention also provides methods for inhibiting gene expression using the transcriptional inhibitor fusion proteins of the invention. These methods can be used to down-regulate basal, constitutive or tissue-specific transcription of a tetO-linked gene of interest. For example, a gene of interest that is operatively linked to tetO sequences and additional positive regulatory elements (e.g., consitutive or tissue-specific enhancer sequences) will be transcribed in host cells at a level that is primarily determined by the strength of the positive regulatory elements in the host cell. Moreover, a gene of interest that is operatively linked to tetOsequences and only a minimal promoter sequence may exhibit varying degrees of basal level transcription depending on the host cell or tissue and/or the site of integration of the sequence. In a host cell containing such a target sequence and expressing an inhibitor fusion protein of the invention, transcription of the target sequence can be down regulated in a controlled manner by altering the concentration of Tc (or analogue) in contact with the host cell. For example, when the inhibitor fusion protein binds to tetO in the absence of Tc, the concentration of Tc in contact with the host cell is reduced to inhibit expression of the target gene. Preferably, a host cell is cultured in the absence of Tc to keep target gene expression repressed. Likewise, Tc is not administered to a host organism to keep target gene expression repressed. Alternatively, when the inhibitor fusion protein binds to tetO in the presence of Tc, the concentration of Tc in contact with the host cell is increased to inhibit expression of the target gene. For example, Tc is added to the culture medium of a host cell or Tc is administered to a host organism to repress target gene expression.

The inhibitor fusion proteins described herein can inhibit a tetO-linked gene of interest in which the tetO sequences are positioned 5' of a minimal promoter sequence (e.g., tetracycline-regulated transcription units as described in Section III, above). Furthermore, the inhibitor fusion protein may be used to inhibit expression of a gene of interest in which tetO-linked sequences are located 3' of the promoter sequence but 5' of the transcription start site. Still further, the inhibitor fusion protein may be used to inhibit expression of a gene of interest in which tetO-linked sequences are located 3' of the transcription start site.

Various Tc analogues as described in Section VI, part A, above, with respect to the transactivator fusion proteins can similarly be used to regulate the activity of the inhibitor fusion proteins. Moreover, the methods of in vitro culture with Tc (or analogue) and in vivo administration of Tc (or analogue) described in Section VI, part A, are equally applicable to the transcriptional inhibitor fusion proteins.

C Combined Positive and Negative Regulation of Gene Expression

In addition to regulating gene expression using either a transcriptional activator or inhibitor fusion protein alone, the two types of fusion proteins can be used in combination to allow for both positive and negative regulation of expression of one or more target genes in a host cell. Thus, a transcriptional inhibitor protein that binds to tetO either (i) in the absence, but not the presence, of Tc, or (ii) in the presence, but not the absence, of Tc, can be used in combination with a transactivator protein that binds to tetO either (i) in the absence, but not the presence, of Tc, or (ii) in the presence, but not the absence, of Tc. Transactivator proteins that bind to tetO in the absence, but not the presenc, of Tc (e.g., wild-type TetR-activator fusion proteins) are described in further detail in U.S. Ser. No. 08/076,726, U.S. Ser. No. 08/076,327 and U.S. Ser. No. 08/260,452. Transactivator fusion proteins that bind to tetO in the presence, but not the absence, of Tc (e.g., mutated TetR-activator fusion proteins) are described herein (see Section I above) and in U.S. Ser. No. 08/270,637 and U.S. Ser. No. 08/275,876. Transcriptional inhibitor fusion proteins are described herein in Section IV.

As described above in Section III, Part C, when more than one TetR fusion protein is expressed in a host cell or organism, additional steps may be taken to inhibit heterodimerization between the different TetR fusion proteins.

For example, a transactivator composed of a TetR of one class may be used in combination with a transcriptional inhibitor composed of a TetR of a second, different class that does not heterodimerize with the first class of TetR. Alternatively, amino acid residues of the TetR involved in dimerization may be mutated to inhibit heterodimerization. However, even if some heterodimerization between transactivator and inhibitor fusion proteins occurs in a host cell, sufficient amounts of homodimers should be produced to allow for efficient positive and negative regulation as described herein.

It will be appreciated by those skilled in the art that various combinations of activator and inhibitor proteins can be used to regulate a single tetO-linked gene of interest in both a positive and negative manner or to regulate multiple tetO-linked genes of interest in a coordinated manner or in an independent manner using the teachings described herein. The precise regulatory components utilized will depend upon the genes to be regulated and the type of regulation desired. Several non-limiting examples of how the transactivator and inhibitor fusion proteins may be used in combination are described further below. However, many other possible combinations will be evident to the skilled artisan in view of the teachings herein and are intended to be encompassed by the invention.

Figure 10:
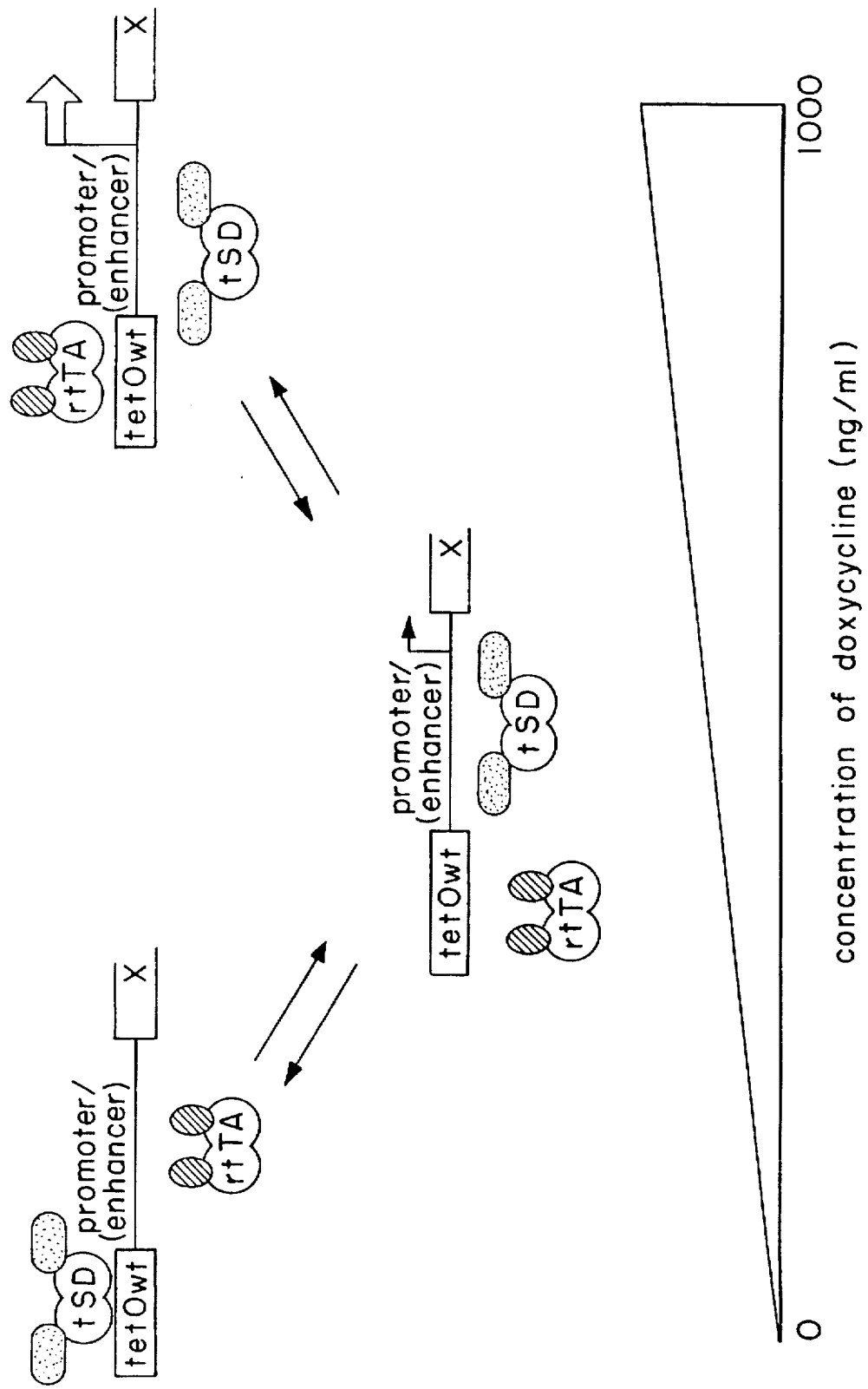
FIG. 10 is a schematic diagram of the negative and positive regulation of a tet operator (tetOwt)-linked gene of interest by a tetracycline-regulated transcriptional inhibitor protein (tSD) and a tetracycline-inducible transcriptional activator fusion protein (rtTA), respectively, in the presence of increasing concentrations of the tetracycline analogue doxycycline.

In a preferred embodiment, illustrated schematically in FIG. 10, expression of a tetO-linked target gene of interest in a host cell is regulated in both a negative and positive manner by the combination of an inhibitor fusion protein that binds to tetO in the absence, but not the presence, of tetracycline or analogue thereof (referred to as a tetracycline controlled silencing domain, or tSD) and an activator fusion protein that binds to tetO in the presence, but not the absence, of tetracycline or analogue thereof (referred to as a reverse tetracycline controlled transactivator, or rtTA). In addition to tetO sequences, the target gene is linked to a promoter, and may contain other positive regulatory elements (e.g., enhancer sequences) that contribute to basal level, constitutive transcription of the gene in the host cell. Binding of tSD to the tetO sequences in the absence of tetracycline or analogue (e.g., doxycycline) inhibits the basal constitutive transcription of the gene of interest, thus keeping the gene of interest in a repressed state until gene expression is desired. When gene expression is desired, the concentration of tetracycline or analogue (e.g., doxycycline) in contact with the host cell increased. Upon addition of the drug, tSD loses the ability to bind to tetO sequences whereas the previously unbound rtTA acquires the ability to bind to tetO sequences. The resultant binding of rtTA to the tetO sequences linked to the gene of interest thus stimulates transcription of the gene of interest. The level of expression may be controlled by the concentration of tetracycline or analogue, the type of Tc analogue used, the duration of induction, etc., as described previously herein. It will be appreciated that the reverse combination of fusion proteins (i.e., the inhibitor binds in the presence but not the absence of the drug and the activator binds in the absence but not the presence of the drug) can also be used. In this case, expression of the gene of interest is kept repressed by contacting the host cell with the drug (e.g., culture with Tc or analogue) and gene expression is activated by removal of the drug.

In another embodiment, the activator and inhibitor fusion proteins, as described in the previous paragraph, are used in combination to coordinately regulate, in both a positive and negative manner, two genes of interest using the bidirectional tetO-linked transcription unit described in Section III, Part B above. In this case, Gene 1 and Gene 2 are linked to the same tetO sequence(s), but in opposite orientations. The inhibitor fusion protein is used to repress basal levels of transcription of both Gene 1 and Gene2 in a coordinate manner, whereas the transactivator fusion protein is used to stimulate expression of Gene 1 and Gene 2 in a coordinate manner.

In yet another embodiment, the activator and inhbitor fusion proteins are used to independently regulate two or more genes of interest using the tetO-linked transcription units as described in Section III, Part C above. For example, in one embodiment, a transactivator fusion protein that binds to one class of tetO sequences (e.g., class A) in the presence, but not the absence of Tc or analogue is used in combination with an inhibitor fusion protein that binds to a second, different class of tetO sequences (e.g., class B) also in the presence, but not the absence, of Tc or analogue. In a host cell containing Gene 1 linked to class A tetO sequences and Gene 2 linked to class B tetO sequences, both genes will be expressed at basal levels in the absence of the drug, whereas expression of Gene 1 will be stimulated upon addition of the drug and expression of Gene 2 will be repressed upon addition of the drug.

Alternatively, in another embodiment, the transactivator binds to one class of tetO sequences (e.g., class A) in the presence, but not the absence, of Tc or analogue and the inhibitor fusion protein binds to a second, different class of tetO sequences (e.g., class B) in the absence but not the presence of Tc or analogue. In the host cell as described in the previous paragraph, Gene 1 will be expressed at basal levels in the absence of the drug and will be stimulated upon addition of the drug, whereas Gene 2 will be repressed in the absence of the drug but will have basal levels expression upon addition of the drug. Various other possible combinations will be apparent to the skilled artisan. Transactivator and inhibitor fusion proteins that bind to different classes of tetO sequences can be prepared as described in Section I, Part A. Target transcription units comprising tetO sequences of different classes can be prepared as described in Section III, Part C.

VII. Applications of the Invention

The invention is widely applicable to a variety of situations where it is desirable to be able to turn gene expression on and off, or regulate the level of gene expression, in a rapid, efficient and controlled manner without causing pleiotropic effects or cytotoxicity. Thus, the system of the invention has widespread applicability to the study of cellular development and differentiation in eukaryotic cells, plants and animals. For example, expression of oncogenes can be regulated in a controlled manner in cells to study their function. Additionally, the system can be used to regulate the expression of site-specific recombinases, such as CRE or FLP, to thereby allow for irreversible modification of the genotype of a transgenic organism under controlled conditions at a particular stage of development. For example, drug resistance markers inserted into the genome of transgenic plants that allow for selection of a particular transgenic plant could be irreversibly removed via a Tc-regulated site specific recombinase. Other applications of the regulatory system of the invention include:

A. Gene Therapy

The invention may be particularly useful for gene therapy purposes, in treatments for either genetic or acquired diseases. The general approach of gene therapy involves the introduction of nucleic acid into cells such that one or more gene products encoded by the introduced genetic material are produced in the cells to restore or enhance a functional activity. For reviews on gene therapy approaches see Anderson, W. F. (1992) *Science* 256:808–813; Miller, A. D. (1992) *Nature* 357:455–460; Friedmann, T. (1989) *Science* 244:1275–1281; and Cournoyer, D., et al. (1990) *Curr. Opin. Biotech.* 1:196–208. However, current gene therapy vectors typically utilize constitutive regulatory elements which are responsive to endogenous transcriptions factors. These vector systems do not allow for the ability to modulate the level of gene expression in a subject. In contrast, the inducible regulatory system of the invention provides this ability.

To use the system of the invention for gene therapy purposes, in one embodiment, cells of a subject in need of gene therapy are modified to contain 1) nucleic acid encoding a transactivator fusion protein of the invention in a form suitable for expression of the transactivator in the host cells and 2) a gene of interest (e.g., for therapeutic purposes) operatively linked to a tet operator sequence(s). The cells of the subject can be modified ex vivo and then introduced into the subject or the cells can be directly modified in vivo (methods for modification of the cells are described above in Section II). Expression of the gene of interest in the cells of the subject is then stimulated by administering Tc or a Tc analogue to the patient. The level of gene expression can be varied depending upon which particular Tc analogue is used as the inducing agent. The level of gene expression can also be modulated by adjusting the dose of the tetracycline, or analogue thereof, administered to the patient to thereby adjust the concentration achieved in the circulation and the tissues of interest.

Moreover, in another embodiment, a transcriptional inhibitor fusion protein is used to further control the level of expression of the gene of interest. For example, the cells of the subject can be modified to also contain a nucleic acid encoding a transcriptional inhibitor fusion protein that binds to tetO in the absence of Tc. The nucleic acid is in a form suitable for expression of the inhibitor fusion protein in the host cells. Thus, prior to administration of Tc (or analogue) to the subject, the basal level of transcription of the gene of interest will be kept silent by the inhibitor fusion protein. Upon administration of Tc, binding of the inhibitor fusion protein to tetO will be inhibited whereas binding of the transactivator fusion will be induced, thereby stimulating transcription of the gene of interest. Such combined positive and negative regulation of gene expression using both a transactivator fusion protein and transcriptional inhibitor fusion protein of the invention is illustrated schematically in FIG. 10.

Conventional detection methods known in the art, such as an enzyme linked immunosorbent assay, can be used to monitor the expression of the regulated protein of interest in the host cells and the concentration of Tc or Tc analogue can be varied until the desired level of expression of the protein of interest is achieved. Accordingly, expression of a protein of interest can be adjusted according to the medical needs of an individual, which may vary throughout the lifetime of the individual. To stop expression of the gene of interest in cells of the subject, administration of the inducing agent is stopped. Thus, the regulatory system of the invention offers the advantage over constitutive regulatory systems of allowing for modulation of the level of gene expression depending upon the requirements of the therapeutic situation.

Genes of particular interest to be expressed in cells of a subject for treatment of genetic or acquired diseases include those encoding adenosine deaminase, Factor VIII, Factor IX, dystrophin, β-globin, LDL receptor, CFTR, insulin, erythropoietin, anti-angiogenesis factors, growth hormone, glucocerebrosidase, β-glucouronidase, α1-antitrypsin, phenylalanine hydroxylase, tyrosine hydroxylase, ornithine transcarbamylase, arginosuccinate synthetase, UDP-glucuronysyl transferase, apoA1, TNF, soluble TNF receptor, interleukins (e.g., IL-2), interferons (e.g., α- or γ-IFN) and other cytokines and growth factors. Cells types which can be modified for gene therapy purposes include hematopoietic stem cells, myoblasts, hepatocytes, lymphocytes, skin epithelium and airway epithelium. For further descriptions of cell types, genes and methods for gene therapy see e.g., Wilson, J. M et al. (1988) *Proc. Natl. Acad. Sci. USA* 85:3014–3018; Armentano, D. et al. (1990) *Proc. Natl. Acad. Sci. USA* 87:6141–6145; Wolff, J. A. et al. (1990) *Science* 247:1465–1468; Chowdhury, J. R. et al. (1991) *Science* 254:1802–1805; Ferry, N. et al. (1991) *Proc. Natl. Acad. Sci. USA* 88:8377–8381; Wilson, J. M. et al. (1992) *J. Biol. Chem.* 267:963–967; Quantin, B. et al. (1992) *Proc. Natl. Acad. Sci. USA* 89:2581–2584; Dai, Y. et al. (1992) *Proc. Natl. Acad. Sci. USA* 89:10892–10895; van Beusechem, V. W. et al. (1992) *Proc. Natl. Acad. Sci. USA* 89:7640–7644; Rosenfeld, M. A. et al. (1992) *Cell* 68:143–155; Kay, M. A. et al. (1992) *Human Gene Therapy* 3:641–647; Cristiano, R. J. et al. (1993) *Proc. Natl. Acad. Sci USA* 90:2122–2126; Hwu, P. et al. (1993) *J. Immunol.* 150:4104–4115; and Herz, J. and Gerard, R. D. (1993) *Proc. Natl. Acad. Sci. USA* 90:2812–2816.

Gene therapy applications of particular interest in cancer treatment include overexpression of a cytokine gene (e.g., TNF-a) in tumor infiltrating lymphocytes or ectopic expression of cytokines in tumor cells to induce an anti-tumor immune response at the tumor site), expression of an enzyme in tumor cells which can convert a non-toxic agent into a toxic agent, expression of tumor specific antigens to induce an anti-tumor immune response, expression of tumor suppressor genes (e.g., p53 or Rb) in tumor cells, expression of a multidrug resistance gene (e.g., MDR1 and/or MRP) in bone marrow cells to protect them from the toxicity of chemotherapy.

Gene therapy applications of particular interest in treatment of viral diseases include expression of trans-dominant negative viral transactivation proteins, such as trans-dominant negative tat and rev mutants for HIV or trans-dominant ICp4 mutants for HSV (see e.g., Balboni, P. G. et al. (1993) *J. Med. Virol.* 41:289–295; Liem, S. E. et al. (1993) *Hum. Gene Ther.* 4:625–634; Malim, M. H. et al. (1992) *J. Exp. Med.* 176:1197–1201; Daly, T. J. et al. (1993) *Biochemistry* 32:8945–8954; and Smith, C. A. et al. (1992) *Virology* 191:581–588), expression of trans-dominant negative envelope proteins, such as env mutants for HIV (see e.g., Steffy, K. R. et al. (1993) *J. Virol.* 67:1854–1859), intracellular expression of antibodies, or fragments thereof, directed to viral products ("internal immunization", see e.g., Marasco, W. A. et al. (1993) *Proc. Natl. Acad. Sci. USA* 90:7889–7893) and expression of soluble viral receptors, such as soluble CD4. Additionally, the system of the invention can be used to conditionally express a suicide gene in cells, thereby allowing for elimination of the cells after they have served an intended function. For example, cells used for vaccination can be eliminated in a subject after an immune response has been generated the subject by inducing expression of a suicide gene in the cells by administering Tc or a Tc analogue to the subject.

B. Production of proteins in Vitro

Large scale production of a protein of interest can be accomplished using cultured cells in vitro which have been modified to contain 1) a nucleic acid encoding a transactivator fusion protein of the invention in a form suitable for expression of the transactivator in the cells and 2) a gene encoding the protein of interest operatively linked to a tet operator sequence(s). For example, mammalian, yeast or fungal cells can be modified to contain these nucleic acid components as described herein. The modified mammalian, yeast or fungal cells can then be cultured by standard fermentation techniques in the presence of Tc or an analogue thereof to induce expression of the gene and produce the protein of interest. Accordingly, the invention provides a production process for isolating a protein of interest. In the process, a host cell (e.g., a yeast or fungus), into which has been introduced both a nucleic acid encoding a transactivator fusion protein of the invention and a nucleic acid encoding the protein of the interest operatively linked to at least one tet operator sequence, is grown at production scale in a culture medium in the presence of tetracycline or a tetracycline analogue to stimulate transcription of the nucleotides sequence encoding the protein of interest (i.e., the nucleotide sequence operatively linked to the tet operator sequence(s)) and the protein of interest is isolated from harvested host cells or from the culture medium. Standard protein purification techniques can be used to isolate the protein of interest from the medium or from the harvested cells.

C. Production of Proteins in Vivo

The invention also provides for large scale production of a protein of interest in animals, such as in transgenic farm animals. Advances in transgenic technology have made it possible to produce transgenic livestock, such as cattle, goats, pigs and sheep (reviewed in Wall, R. J. et al. (1992) *J. Cell. Biochem.* 49:113–120; and Clark, A. J. et al. (1987) *Trends in Biotechnology* 5:20–24). Accordingly, transgenic livestock carrying in their genome the components of the inducible regulatory system of the invention can be constructed, wherein a gene encoding a protein of interest is operatively linked to at least one tet operator sequence. Gene expression, and thus protein production, is induced by administering Tc (or analogue thereof) to the transgenic animal. Protein production can be targeted to a particular tissue by linking the nucleic acid encoding the transactivator fusion protein to an appropriate tissue-specific regulatory element(s) which limits expression of the transactivator to certain cells. For example, a mammary gland-specific regulatory element, such as the milk whey promoter (U.S. Pat. No. 4,873,316 and European Application Publication No. 264,166), can be linked to the transactivator transgene to limit expression of the transactivator to mammary tissue. Thus, in the presence of Tc (or analogue), the protein of interest will be produced in the mammary tissue of the transgenic animal. The protein can be designed to be secreted into the milk of the transgenic animal, and if desired, the protein can then be isolated from the milk.

D. Animal Models of Human Disease

The transcriptional activator and inhibitor proteins of the invention can be used alone or in combination to stimulate or inhibit expression of specific genes in animals to mimic the pathophysiology of human disease to thereby create animal models of human disease. For example, in a host animal, a gene of interest thought to be involved in a disease can be placed under the transcriptional control of one or more tet operator sequences (e.g., by homologous recombination, as described herein). Such an animal can be mated to a second animal carrying one or more transgenes for a transactivator fusion protein and/or an inhibitor fusion protein to create progeny that carry both a tetracycline-regulated fusion protein(s) gene and a tet-regulated target sequence. Expression of the gene of interest in these progeny can be modulated using tetracycline (or analogue). For example, expression of the gene of interest can be down-modulated using a transcriptional inhibitor fusion protein to examine the relationship between gene expression and the disease. Such an approach may be advantageous over gene "knock out" by homologous recombination to create animal models of disease, since the tet-regulated system described herein allows for control over both the levels of expression of the gene of interest and the timing of when gene expression is down- or up-regulated.

E. Production of Stable Cell Lines for Gene Cloning and Other Uses

The transcriptional inhibitor system described herein can be used keep gene expression "off" (i.e., expressed) to thereby allow production of stable cell lines that otherwise may not be produced. For example, stable cell lines carrying genes that are cytotoxic to the cells can be difficult or impossible to create due to "leakiness" in the expression of the toxic genes. By repressing gene expression of such toxic genes using the transcriptional inhibitor fusion proteins of the invention, stable cell lines carrying toxic genes may be created. Such stable cell lines can then be used to clone such toxic genes (e.g., inducing the expression of the toxic genes under controlled conditions using Tc or analog). General methods for expression cloning of genes, to which the transcriptional inhibitor system of the invention can be applied, are known in the art (see e.g., Edwards, C. P. and Aruffo, A. (1993) *Curr. Opin. Biotech.* 4:558–563) Moreover, the transcriptional inhibitor system can be applied to inhibit basal expression of genes in other cells to create stable cell lines, such as in embryonic stem (ES) cells. Residual expression of certain genes introduced into ES stems may result in an inability to isolate stably transfected clones. Inhibition of transcription of such genes using the transcriptional inhibitor system described herein may be useful in overcoming this problem.

Advantages

The inducible regulatory system of the invention utilizing a transactivator fusion protein addresses and overcomes many of the limitations of other inducible regulatory systems in the art. For example, very high intracellular concentrations of the transcriptional activator fusion protein of the invention are not required for efficient regulation of gene expression. Additionally, since gene expression is induced by adding rather than removing the inducing agent, the induction kinetics in the system of the invention are not limited by the rate of removal of the inducing agent and thus are typically faster. Moreover, the inducing agent is only present when gene transcription is induced, thereby avoiding the need for the continuous presence of an agent to keep gene expression off.

Use of the transcriptional inhibitor fusion proteins of the invention to inhibit transcription in eukaryotic cells also provide advantages over the use of prokaryotic repressors alone (e.g., TetR, lacR) to inhibit transcription in eukaryotic cells. Since the inhibitor fusion proteins of the invention contain a eukaryotic transcriptional silencer domain, these fusion proteins should be more efficient at repressing transcription in eukaryotic cells, and thus may potentially require lower intracellular concentrations for efficient repression with less liklihood of "leakiness". Additionally, by insertion of tetO sequences into the regulatory region of an endogenous gene, the transcriptional inhibitor fusion proteins of the invention can be used to down-regulate constitutive and/or tissue-specific expression of endogenous genes.

Furthermore, in contrast to various versions of the lac system (e.g., Labow et al. (1990) *Mol. Cell. Biol.* 10:3343–3356; Baim et al. (1991) *Proc. Natl. Acad. Sci.*

USA 88:5072–5076), which are limited by the negative properties of the inducing agent (IPTG) and/or by the need to increase the temperature in order to induce gene expression (which may elicit pleiotropic effects), the inducing agent used in the system of the invention (Tc or an analogue thereof) has many advantageous properties: 1) Tc and analogues thereof exhibit high affinity for TetR and low toxicity for eukaryotic cells, and thus can be used for gene induction at concentrations that do not affect cell growth or morphology; 2) Tc analogues which retain TetR binding but which have reduced antibiotic activity exist and can be used as inducing agents, thereby avoiding possible side effects from the antibiotic property of Tc; 3) the pharmacokinetic properties of Tc and Tc analogues enable rapid and efficient cellular uptake and penetration of physiological barriers, such as the placenta or the blood-brain barrier; and 4) Tc analogues with different induction capabilities permit modulation of the level of gene expression.

Thus, the invention provides an inducible regulatory system which allows for rapid activation of gene transcription without cellular toxicity and a range of induction indices. The increase in gene expression upon induction typically is between 1000- and 2000-fold and can be as high as about 20,000-fold. Alternatively, lower levels of gene induction, e.g., 10-fold, can be achieved depending upon which inducing agent is used. This system can be utilized in a wide range of applications. These applications include gene therapy, large-scale production of proteins in cultured cells or in transgenic farm animals, and the study of gene function, for example in relationship to cellular development and differentiation. Moreover, the novel transcription units of the invention allow for coordinate or independent regulation of the expression of multiple genes utilizing the regulatory components of the invention.

This invention is further illustrated by the following examples which should not be construed as limiting. The contents of all references, patents and published patent applications cited throughout this application are hereby incorporated by reference.

EXAMPLE 1

Selection of a Mutated Tet Repressor and Construction of a Tetracycline Inducible Transcriptional Activator A "reverse" Tet repressor, which binds to its target DNA in the presence rather than the absence of tetracycline, was generated by chemical mutagenesis and selection essentially as described in Hecht, B. et al. (1993) *J. Bacteriology* 175:1206–1210. Single-stranded DNA (coding and non-coding strands) encoding the wild-type Tn10-derived Tet repressor was chemically mutagenized with sodium nitrite. Single-stranded DNAs (40 μg in 40 μl in Tris-EDTA buffer) were mixed with 10 μl of 2.5M sodium acetate (pH 4.3) and 50 μl of sodium nitrate ranging between 0.25M and 2M and incubated for 45 to 60 minutes at room temperature. After mutagenesis, the complementary strand was synthesized using reverse transcriptase or by amplification using the polymerase chain reaction with Taq DNA polymerase. Since the mutagenesis procedure yields multiple mutations in the DNA, three fragments of the gene, of about 200 base pairs each, were individually subcloned into a wt Tet repressor gene in a recombinant expression vector to replace the corresponding portion of the wild-type gene. This created a pool of mutated Tet repressor genes wherein each gene had mostly single mutations in the 200 base pair mutagenized fragment of the gene.

The pool of mutated Tet repressors were screened in a genetic assay which positively selects for a functional interaction between a Tet repressor and its cognate operator using *E. coli* strain WH207(λWH25) (the construction of this strain is described in detail in Wissmann, A. et al. (1991) *Genetics* 128:225–232). In this *E. coli* strain, tet operators direct the expression of divergently arranged β-galactoside (lacZ) and Lac repressor (lacI) genes and the lac regulatory region directs the expression of a galactokinase (galK) gene. Binding of Tet repressors to tet operators turns off transcription of the lacI and lacZ genes. The absence of Lac repressor allows for expression of the galK gene, which enables the *E. coli* strain to use galactose as a sole carbon source, which serves as one marker. The lacZ$^-$ phenotype serves as a second marker. Thus, bacteria containing Tet repressors which bind to tet operators have a Gal$^+$, lacZ$^-$ phenotype. Bacteria containing wild-type Tet repressors have a Gal$^+$, lacZ$^-$ phenotype in the absence of tetracycline. A mutated "reverse" Tet repressor (rTetR) was selected based upon a Gal$^+$, lacZ$^-$ phenotype in the presence of tetracycline.

The nucleotide and amino acid sequence of the rTetR mutant are shown in SEQ ID NOs: 1 (nucleotide positions 1–621) and 2 (amino acid positions 1–207), respectively. Sequence analysis of the rTetR mutant showed the following amino acid and nucleotide changes:

| aa (position) | | affected codon | |
| --- | --- | --- | --- |
| wild-type | mutant | wild-type | mutant |
| glu(71) | lys | GAA | AAA |
| asp(95) | asn | GAT | AAT |
| leu(101) | ser | TTA | TCA |
| gly(102) | asp | GGT | GAT |

Two additional mutations did not result in an amino acid exchange:

| aa (position) | | affected codon | |
| --- | --- | --- | --- |
| wild-type | mutant | wild-type | mutant |
| leu(41) | leu | TTG | CTG |
| arg(80) | arg | CGT | CGC |

To convert the rTetR mutant to a transcriptional activator, a 399 base pair XbaI/Eco47III fragment encoding amino acids 3 to 135 of rTetR (i.e., encompassing the mutated region) was exchanged for the corresponding restriction fragment of the expression vector pUHD15-1 to create pUHD17-1. In pUHD15-1, nucleotide sequences encoding wild-type TetR are linked in frame to nucleotide sequences encoding the C-terminal 130 amino acids of herpes simplex virus VP16. These transactivator sequences are flanked upstream by a CMV promoter/enhancer and downstream by an SV40 poly(A) site (the construction of pUHD15-1 is described in more detail in U.S. Ser. No. 08/076,726 and Gossen, M. and Bujard, H. (1992) *Proc. Natl. Acad. Sci. USA* 89:5547–5551). Thus, in pUHD17-1, nucleotide sequences encoding the reverse TetR mutant are linked in frame to VP16 sequences to create a reverse Tc-controlled transactivator (referred to herein as tTA$^R$). The analogous exchange of the mutated region of rTetR for the wild-type region of TetR was performed with plasmid pUHD152-1, which is the same as pUHD15-1 except that it additionally contains nucleotide sequences encoding a nuclear localization signal linked in-frame to the 5' end of the nucleotide sequences encoding the Tet repressor. The amino acid sequence of the nuclear localization signal is MPKRPRP (SEQ ID NO: 5), which is linked to the serine at amino acid position 2 of TetR. The resulting expression vector encoding the reverse Tc-controlled transactivator including a nuclear localization signal (referred to herein as ntTA$^R$) was named pUHD172-1.

EXAMPLE 2

Tetracycline-Induced Stimulation of Transcription by tTA$^R$ Transient Transfection The pUHD17-1 and pUHD172-1 expression vectors were transiently transfected by a standard calcium phosphate method into HeLa cells together with a reporter plasmid, pUHC43-3, in which heptameric tet operators are fused upstream of a minimal hCMV-promoter and a luciferase reporter gene (the reporter plasmid is described in detail in U.S. Ser. No. 08/076,726 and Gossen, M. and Bujard, H. (1992) *Proc. Natl. Acad. Sci. USA* 89:5547–5551). After incubation of the transfected cells at 37° C. for 20 hours in the presence or absence of tetracycline (or an analogue thereof), luciferase activity was assayed as follows: Cells grown to ~80 % confluency in 35 mm dishes in Eagle's minimal essential medium were washed with 2 ml of phosphate-buffered saline before they were lysed in 25 mM Tris phosphate, pH 7.8/2 mM dithiothreitol/2 mM diaminocyclohexanetetraacetic acid/10% glycerol/1% Triton-X-100 for 10 minutes at room temperature. The lysate was scraped off the culture dishes and centrifuged for 10 seconds in an Eppendorf centrifuge. Next, aliquots (10 μl) of the supernatant were mixed with 250 μl of 25 mM glycylglycine/15 mM MgSO4/5 mM ATP and assayed for luciferase activity in a Lumat LB9501 (Berthold, Wildbad, F.R.G.) using the integral mode (10 seconds). D-Luciferin (L6882, Sigma) was used at 0.5 mM. The background signal measured in extracts of HeLa cells that did not contain a luciferase gene was indistinguishable from the instrument background (80–120 relative light units (rlu)/10 sec.). Protein content of the lysate was determined according to Bradford (Bradford, M. M. (1976) *Anal. Biochem.* 72:248–254). Cells transfected with plasmids encoding either tTA$^R$ or ntTA$^R$ showed an increased level of luciferase activity in the presence of tetracyclines. This effect was consistently more pronounced when anhydrotetracycline (ATc) was used instead of tetracycline.

Stable Transfection

After this transient transfection analysis, expression vectors were prepared for stable transfection of cells. A pSV2neo-derived neomycin resistance cassette (described in Southern, P. J. and Berg, P. (1982) *J. Mol. Appl. Genet.* 1:327–341) was integrated into the transactivator expression vectors pUHD17-1 and pUHD172-1, resulting in pUHD17-1 neo and pUHD172-1neo, respectively. pUHD172-1neo, coding for ntTA$^R$, was stably integrated into HeLa cells by standard techniques. Ten G418-resistant cell clones were analyzed for their phenotype by transient supertransfection with pUHC13-3 carrying the luciferase gene under the control of a minimal CMV promoter and tet operators. Three clones, HR4, HR5 and HR10, showed a strong increase of luciferase activity in the presence of ATc. From these clones, HR5 was selected for further experiments.

To create stable transfectants for both ntTA$^R$ and a tet operator-linked luciferase reporter gene, HR5 cells were cotransfected with pUH13-3 and pHMR272, which encodes for hygromycin resistance (see Bernhard, H-U. et al. (1985) *Exp. Cell Res.* 158:237–243), and hygromycin resistant clones were selected. In an analogous experiment, HR5 cells were cotransfected with pUH13-7 and pHMR272. pUH13-7 contains a minimal promoter sequence spanning position +19 to −37 of the HSVtk promoter adjacent to the heptameric tetO sequences, rather than a minimal CMV promoter. From 21 hygromycin resistant clones, 10 showed inducible luciferase activity upon addition of Tc or doxycycline (Dc) to the culture medium. Clones containing the luciferase reporter gene linked to a minimal CMV promoter are referred to as HR5-C, whereas those containing the luciferase reporter gene linked to a minimal tk promoter are referred to HR5-T.

Six of the HR5 clones stably transfected with a ntTA$^R$-dependent reporter unit and previously shown to be responsive to tetracyclines were grown in parallel in the absence or presence of 1 μg/ml doxycycline. About 3×10$^4$ cells were plated in each 35 mm dish (4 dishes for each clone). After growth for 60 hours, cells were harvested and the luciferase activity of the extracts (in relative light units (rlu)/μg extracted protein) was determined. As shown in Table 1, the absolute expression levels of six clones demonstrate that activation of luciferase gene expression over 3 orders of magnitude is achieved in several of the double stable cell lines containing the ntTA$^R$ regulatory system.

It should be noted that even higher induction factors (e.g., as high as a 20,000-fold increase in expression) could be achieved if, instead of simply adding the inducing agent to the culture medium, the cells were washed prior to induction and then replated in fresh culture medium containing the inducing agent.

TABLE 1

Doxycycline-dependent luciferase activity of double stable luc+/HR5 cell clones

| Clone | Luciferase Activity, rlu/μg protein | | |
|---|---|---|---|
| | −Doxycycline | +Doxycycline | Induction Factor |
| HR5-C6 | 65 | 54,911 | 845 |
| | 62 | 69,525 | 1120 |
| HR5-C11 | 100 | 165,671 | 1660 |
| | 142 | 179,651 | 1270 |
| HR5-C14 | 43 | 44,493 | 1030 |
| | 43 | 56,274 | 1310 |
| HR5-T2 | 56 | 16,696 | 298 |
| | 40 | 16,416 | 410 |
| HR5-T15 | 6.8 | 1838 | 270 |
| | 6.5 | 1688 | 260 |
| HR5-T19 | 4.8 | 1135 | 236 |
| | 5.4 | 1285 | 237 |

Induction of luciferase activity by different tetracyclines

The ability of tetracycline and several different tetracycline analogues to induce luciferase expression in HR5-C11 cells was examined. HR5-C11 cells plated at a density of about 3×10$^4$ cells/35 mm dish (~80% confluency). After full attachment of the cells, the following tetracyclines ere added to the cultures at a concentration of 1 μg/ml: tetracycline-HCl (Tc), oxytetracycline-HCl (OTc), chlorotetracycline (CTc), anhydrotetracycline-HCl (ATc) and doxycycline-HCl (Doxy). These compounds are commercially available from Sigma Chemical Co., St. Louis, Mo., and were kept in aqueous solution at a concentration of 1 μg/ml. Cells grown in the absence of antibiotic (−) served as a control. After 3 days, the cells were harvested and the luciferase activity and the protein content of the extracts were determined. The results are shown in the bar graph of FIG. 1. Each bar in the figure (closed and hatched) represents the relative luciferase activity (normalized toward the amount of extracted protein) of a single culture dish. The mean of the luciferase activities obtained from the two plates grown without tetracyclines was defined as 1. Tc, CTc and OTc showed modest stimulation of luciferase activity. By contrast, ATc and Doxy stimulated luciferase activity approximately 1000 and 1500 fold, respectively.

Dose-response of luciferase activity to doxycycline in HR5-C11 cells

Figure 2:
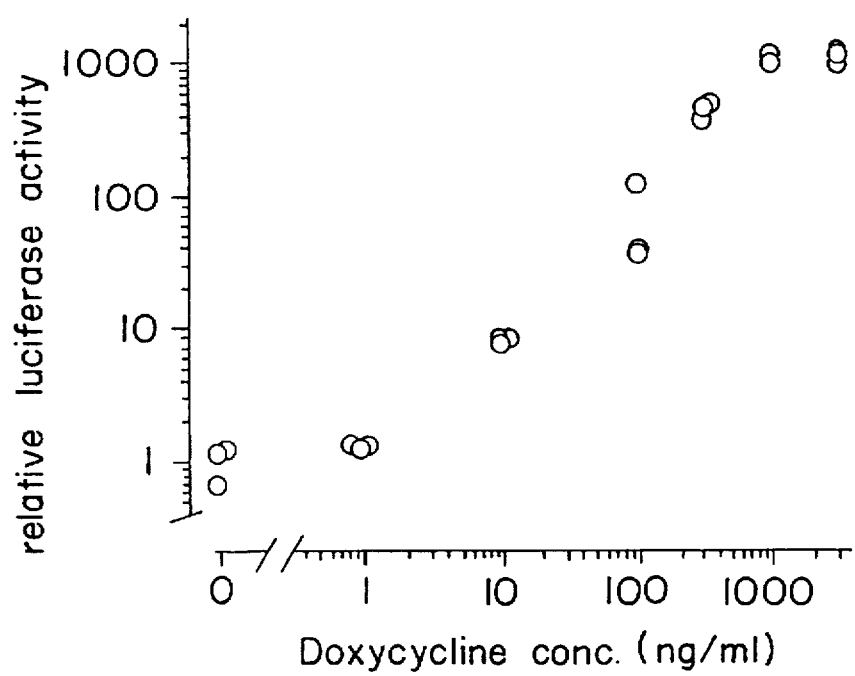
FIG. 2 is a graph depicting the relative luciferase activity in HR5-C11 cells when incubated with different concentrations of doxycycline. The results of three independent experiments are shown.

The above-described experiment examining the induction ability of different tetracyclines revealed that doxycycline was the most potent effector of the tetracyclines examined. Doxycycline was therefore selected to quantitatively analyze its dose-response. HR5-C11 cells were incubated with different concentrations of doxycycline and luciferase activity was measured. The data of three independent experiments are shown in FIG. 2. At less than 10 ng/ml in the culture medium, doxycycline is ineffective at inducing luciferase activity. However, when the concentration was raised above 10 ng/ml, an almost linear increase in expression of luciferase was observed. Maximal activation was achieved at 1 µg/ml. At concentrations above 3 µg/ml, doxycycline showed a slight growth-inhibitory effect on HeLa cells as determined in a MTT-assay.

Kinetics of induction of the ntTA$^R$ system

Figure 3:
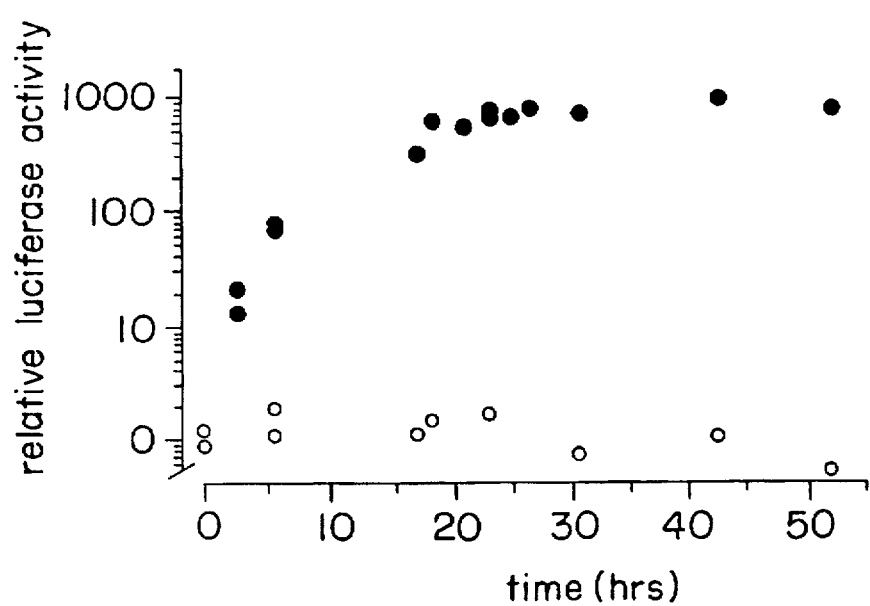
FIG. 3 is a graph depicting the kinetics of induction of luciferase activity in HR5-C11 cells by doxycycline. HR5-C11 cultures were exposed to 1 µg/ml of doxycycline and luciferase activity was measured after different time intervals; (●) cultures containing doxycycline, (o) cultures grown in the absence of antibiotic.

To examine the kinetics of doxycycline-induced ntTA$^R$-mediated induction of gene expression, the time course of induction of luciferase activity in HR5-C11 cells was monitored after addition of doxycycline to the medium (final concentration 1 µg/ml). Cells were cultured in the presence of doxycycline and after various time intervals, the cells were harvested and luciferase activity was determined as described above. As shown in FIG. 3, a 100-fold induction of luciferase activity was observed after 5.5 hours incubation with Doxy. Fully induced levels were achieved in less than 24 hours of incubation with Doxy. Thus, these results indicate that induction of gene expression occurs rapidly following exposure of the cells to the inducing agent.

EXAMPLE 3

Coordinate Regulation of the Expression of Two Nucleotide Sequences by a Tc-Controlled Transcriptional Activator A recombinant expression vector for coordinate, bidirectional transcription of two nucleotide sequences was constructed comprising, in a 5' to 3' direction: a luciferase gene, a first minimal promoter, seven tet operator sequences, a second minimal promoter and a LacZ gene. The construct is illustrated in FIG. 6. In this construct, the luciferase and LacZ genes are oriented such that they are transcribed in opposite orientations relative to the tet operator sequences, i.e., the luciferase gene is transcribed in a 5' to 3' direction from the bottom strand of DNA, whereas the LacZ gene is transcribed in a 5' to 3' direction from the top strand of DNA. The luciferase gene is followed by an SV40 polyadenylation signal, whereas the LacZ gene is followed by a β-globin polyadenylation signal.

Figure 8A:
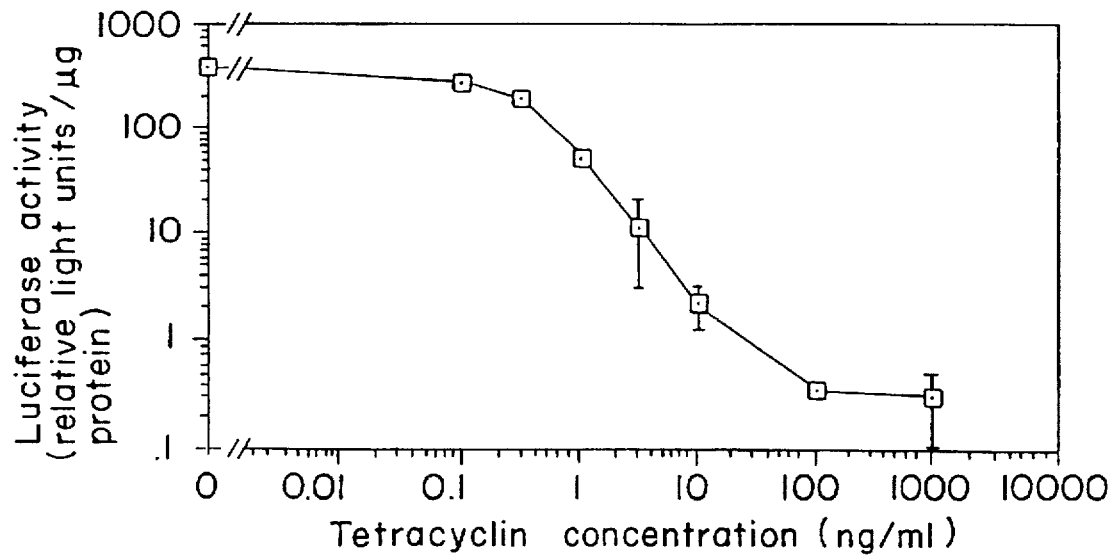
FIG. 8 is two graphs depicting coordinate expression of luciferase and β-galactosidase activity by a tetracycline-regulated transcriptional activator.
Figure 8B:
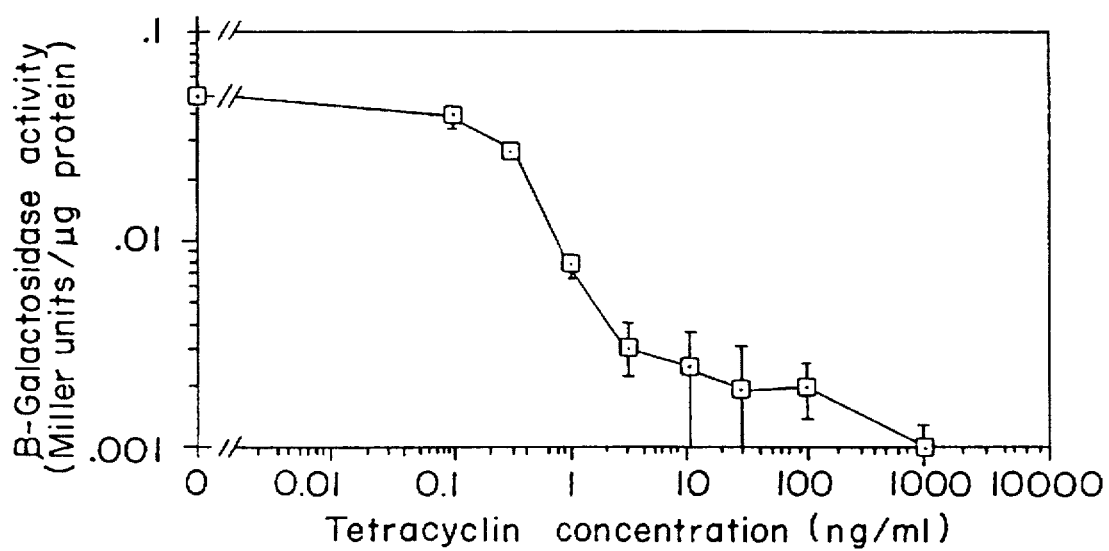

The construct was transfected into the HeLa cell line HtTA-1 cells, which express a wild-type Tet repressor-VP16 fusion protein (referred to as tTA and described in Gossen, M. and Bujard, H. (1992) *Proc. Natl. Acad. Sci. USA* 89:5547–5551). The tTA fusion protein binds to tet operator sequences in the absence of Tc (or analogue) but not in the presence of Tc (or analogue). The construct was cotransfected into HtTA-1 cells with a plasmid which confers hygromycin resistance and stably transfected clones were selected based upon their hygromycin resistant phenotype. Selected hygromycin resistant (Hygr$^r$) clones were examined for luciferase and β-galactosidase activity. Clones positive for all three markers (Hygr$^r$, luc$^+$, β-gal$^+$) were then examined for tetracycline-dependent coregulation of expression of luciferase and β-galactosidase activity by culturing the clones in increasing amounts of tetracycline and measuring luciferase and β-galactosidase activity. The results of such an experiment using clone Ht1316-8/50 are shown in FIG. 8. In the absence of tetracycline (in which case tTA can bind to tet operators and activate gene expression), both luciferase and β-galactosidase activity is detected. In the presence of increasing amounts of tetracycline, luciferase and β-galactosidase activity are coordinately and equivalently downregulated. This data demonstrates that expression of two genes can be coordinately regulated by a tetracycline-controlled transactivator by operatively linking the two genes to the same tet operator sequence(s).

EXAMPLE 4

Figure 11:
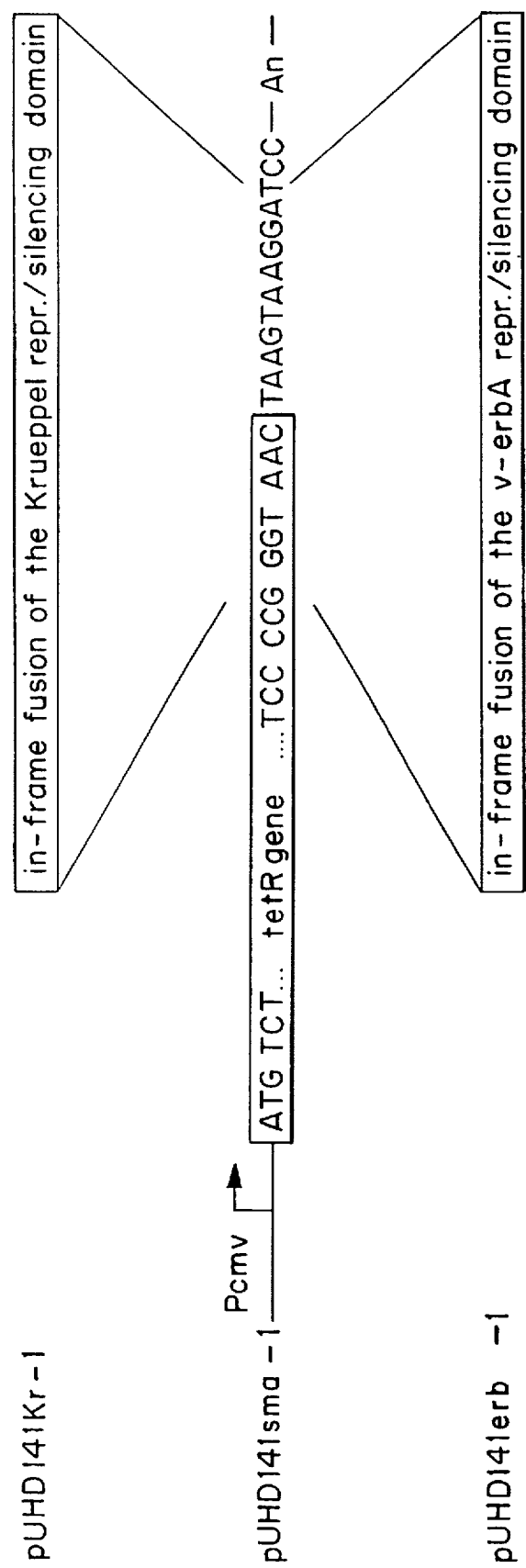
FIG. 11 is a schematic diagram of the construction of TetR-silencer domain fusion contructs by in-frame fusion of nucleic acid encoding either a Krueppel or v-erbA silencer domain to the 3' end of nucleic acid encoding a Tet repressor (tetR gene).

Construction of a Tetracycline-Regulated Transcriptional Inhibitor Fusion Protein Comprising TetR and a Krueppel Silencer Domain To contruct an expression vector encoding a tetracycline-regulated transcriptional inhibitor of the invention (also referred to as a tetacycline controlled silencer domain, or tSD), a nucleic acid fragment encoding a transcriptional silencer domain is ligated into an expression vector containing nucleotide sequences encoding a wild-type or modified (i.e., mutated) TetR such that the silencer domain coding sequences are ligated in-frame with the TetR coding sequences. The plasmid pUHD141sma-1 contains nucleotide sequences encoding a wild-type Tn10-derived Tet repressor (the nucleotide and amino acid sequences of which are shown in SEQ ID NOs: 16 and 17, respectively). In pUHD141sma-1, the TetR coding sequence is linked at its 5' end to a CMV promoter and at its immediate 3' end to a nucleotide sequence that creates a polylinker into which additional nucleic acid fragments can be introduced. The nucleotide sequence across this polylinker region is: TCC CCG GGT AAC TAA GTA AGG ATC C (SEQ ID NO: 24) (wherein TCC CCG GGT ACC encode amino acid residues 205–208 of TetR, namely Ser-Gly-Ser-Asn). This polylinker region includes restriction endonuclease sites for PspAI (CCC GGG) and BamHi (GGA TCC). Downstream of the polylinker region, the plasmid contains an SV40-derived polyadenylation signal. The pUHD141 sma-1 vector is illustrated schematically in FIG. 11.

To construct an expression vector encoding a fusion protein between TetR and a transcriptional silencer domain from the Drosophila Krueppel (Kr) protein, a nucleic acid fragment encoding a silencer domain from Kr is amplified by the polymerase chain reaction (PCR) using Kr cDNA as a template. Oligonucleotide primers are designed which amplify a nucleic acid fragment encoding the C-terminal 64 amino acids of Kr (referred to as C64KR). This region corresponds to amino acid positions 403–466 of the native protein. The nucleotide and amino acid sequences of C64KR are shown in SEQ ID NO: 20 and SEQ ID NO: 21, respectively. PCR primers are designed to include restriction endonuclease sites such that the resultant amplified fragment contains restriction endonuclease sites at its 5' and 3' ends. Restriction endonuclease sites are chosen that are contained within the polylinker of pUHD141sma-1 which allow in-frame, directional ligation of the amplified fragment into the polylinker site. For example, PCR primers are designed which incorporate a PspAI site (CCC GGG) at the 5' end of the fragment encoding C64KR and a BamHI site at the 3' end of the fragment. After a standard PCR reaction, the amplified fragment and pUHD141-sma1 are digested with PspAI and BamHI. The amplified fragment is then ligated directionally into the polylinker site of pUHD141-sma1 using standard ligation conditions to create the expression vector pUHD141kr-1. Standard techniques are used to isolate the desired plasmid and confirm its construction. Construction of pUHD141kr-1 is illustrated schematically in FIG. 11.

The resultant pUHD 14 1kr-1 expression vector contains nucleotide sequences encoding a fusion protein comprising amino acids 1–207 of the wild type TetR linked in-frame to amino acids 403–466 of Kr (C64KR). The nucleotide and amino acid sequences across the junction of the fusion protein are as follows: AGT GGG TCC CCG GGT GAC ATG GAA (SEQ ID NO: 25) and Ser-Gly-Ser-Pro-Gly-Asp-Met-Glu (SEQ ID NO: 26). Ser-Gly-Ser corresponds to amino acids 205–207 of TetR, Pro-Gly are encoded by the polylinker and Asp-Met-Glu correspond to the amino acids 403–405 of C64KR.

Similarly, an expression vector encoding a fusion protein of a mutated TetR (that binds to tetO only in the presence of Tc) and C64KR can be constructed as described above using nucleotide sequences encoding a mutant TetR (the nucleotide and amino acid sequences of which are shown in SEQ ID NOs: 18 and 19, respectively) in place of the wild type TetR sequences in pUHD141 -sma1.

An expression vector encoding a TetR-Kr fusion protein (e.g., pUHD141kr-1) is transiently or stably transfected into host cells as described in Example 2 to express the TetR-Kr fusion protein in the host cell. A reporter gene construct containing one or more tetO sequences, a minimal promoter and a reporter gene, such as luciferase, is also transfected into the cells as described in Example 2. (Reporter gene constructs are described in further detail in U.S. Ser. No. 08/076,726 and Gossen, M. and Bujard, H. (1992) Proc. Natl. Acad. Sci. USA 89:5547–5551). Luciferase activity in the presence and absence of increasing concentrations of Tc or an analogue, e.g., doxycycline, is measured as described in Example 2. For the wild type TetR-Kr fusion protein described above, the transcriptional inhibiting ability of the fusion protein is determined by comparing the amount of luciferase activity in the presence of doxycycline (no repression) to the amount of luciferase activity in the absence of doxycycline (repression). The transcriptional inhibiting activity of the fusion protein can also be tested using reporter gene constructs that exhibit higher basal levels of expression (i.e., higher levels of expression in the presence of doxycycline) by using a reporter gene construct that contains additional positive regulatory elements (e.g., enhancer sequences).

EXAMPLE 5

Construction of a Tetracycline-Regulated Transcriptional Inhibitor Fusion Protein Comprising TetR and a v-erbA Silencer Domain To construct an expression vector encoding a fusion protein between TetR and a transcriptional silencer domain from the v-erbA oncogene product, a nucleic acid fragment encoding a silencer domain from v-erbA is ligated in-frame into pUHD141sma-1 as described in Example 4. A nucleic acid fragment encoding a v-erbA silencer domain suitable for ligation into pUHD141sma-1 is amplified by the polymerase chain reaction (PCR) using a v-erbA cDNA as a template. Oligonucleotide primers are designed which amplify a nucleic acid fragment encoding amino acids 364–635 of the native v-erbA protein. The nucleotide and amino acid sequences of this region of v-erbA are shown in SEQ ID NO: 22 and SEQ ID NO: 23, respectively. As described in Example 4, PCR primers are designed such that the amplified v-erbA fragment contains restriction endonuclease sites at its 5' and 3' ends, such as PspAI at the 5' end and BamHI at the 3' end. After a standard PCR reaction, the amplified fragment and pUHD141-sma1 are digested with PspAI and BamHI. The amplified fragment is then ligated directionally into the polylinker site of pUHD141-sma1 using standard ligation conditions to create the expression vector pUHD141kr-1. Standard techniques can be used to isolate the desired plasmid and confirm its construction. Construction of pUHD141erb-1 is illustrated schematically in FIG. 11.

The resultant pUHD141 erb-1 expression vector contains nucleotide sequences encoding a fusion protein comprising a wild type TetR linked in-frame to amino acids 364–635 of v-erbA. The nucleotide and amino acid sequences across the junction of the fusion protein are as follows: AGT GGG TCC CCG GGT CTG GAC GAC (SEQ ID NO: 27) and Ser-Gly-Ser-Pro-Gly-Leu-Asp-Asp (SEQ ID NO: 28). Ser-Gly-Ser corresponds to amino acids 205–207 of TetR, Pro-Gly are encoded by the polylinker and Leu-Asp-Asp correspond to amino acids 364–366 of the v-erbA silencer domain.

As described in Example 4, an expression vector encoding a fusion protein of a mutated TetR (that binds to tetO only in the presence of Tc) and a v-erbA silencer domain can be constructed as described above using nucleotide sequences encoding a mutant TetR (the nucleotide and amino acid sequences of which are shown in SEQ ID NOs: 18 and 19, respectively) in place of the wild type TetR sequences in pUHD141-sma1.

Expression of the TetR-v-erbA fusion protein in host cells and assaying of the transcriptional inhibiting activity of the fusion protein is as described in Example 4 for the TetR-Kr fusion protein.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An isolated nucleic acid encoding a fusion protein which inhibits transcription in eukaryotic cells, the fusion protein comprising a first polypeptide which binds to tet operator sequences, operatively linked to a heterologous second polypeptide which inhibits transcription in eukaryotic cells.

2. The nucleic acid of claim 1, wherein the first polypeptide binds to tet operator sequences in the absence but not the presence of tetracycline or a tetracycline analogue.

3. The nucleic acid of claim 2, wherein the first polypeptide is a Tet repressor.

4. The nucleic acid of claim 3, wherein the first polypeptide comprises an amino acid sequence shown in SEQ ID NO: 17.

5. The nucleic acid of claim 1, wherein the first polypeptide binds to tet operator sequences in the presence but not the absence of tetracycline or a tetracycline analogue.

6. The nucleic acid of claim 5, wherein the first polypeptide is a mutated Tet repressor.

7. The nucleic acid of claim 6, wherein the mutated Tet repressor has at least one amino acid substitution compared to a wild-type Tet repressor.

8. The nucleic acid of claim 6, wherein the mutated Tet repressor has at least one amino acid addition or deletion compared to a wild-type Tet repressor.

9. The nucleic acid of claim 7, wherein the mutated Tet repressor has an amino acid substitution at at least one amino acid position corresponding to an amino acid position selected from the group consisting of position 71, position 95, position 101 and position 102 of a wild-type Tn10-derived Tet repressor amino acid sequence.

10. The nucleic acid of claim 9, wherein the mutated Tet repressor comprises an amino acid sequence shown in SEQ ID NO: 19.

11. The nucleic acid of claim 1, wherein the second polypeptide comprises a transcription silencer domain of a v-erbA oncogene product.

12. The nucleic acid of claim 11, wherein the second polypeptide comprises an amino acid sequence shown in SEQ ID NO: 23.

13. The nucleic acid of claim 1, wherein the second polypeptide comprises a transcription silencer domain of a Drosophila Krueppel protein.

14. The nucleic acid of claim 13, wherein the second polypeptide comprises an amino acid sequence shown in SEQ ID NO: 21.

15. The nucleic acid of claim 1, wherein the second polypeptide comprises a transcription silencer domain of a protein selected from the group consisting of the retinoic acid receptor alpha, the thyroid hormone receptor alpha, the yeast Ssn6/Tup1 protein complex, the Drosophila protein even-skipped, SIR1, NeP1, the Drosophila dorsal protein, TSF3, SFI, the Drosophila hunchback protein, the Drosophila knirps protein, WT1, Oct-2.1, the Drosophila engrailed protein, E4BP4 and ZF5.

16. The nucleic acid molecule of claim 1, wherein the fusion protein further comprises an operatively linked third polypeptide which promotes transport of the fusion protein to a cell nucleus.

17. A recombinant vector comprising the nucleic acid molecule of claim 2 in a form suitable for expression of the fusion protein in a host cell.

18. A host cell comprising the recombinant vector of claim 17.

19. The host cell of claim 18, further comprising a nucleotide sequence to be transcribed operatively linked to at least one tet operator sequence.

20. The host cell of claim 19, wherein the nucleotide sequence to be transcribed is an exogenous nucleotide sequence introduced into the host cell.

21. The host cell of claim 19, wherein the nucleotide sequence to be transcribed is an endogenous nucleotide sequence to which at least one tet operator sequence has been operatively linked.

22. The host cell of claim 19, further comprising nucleic acid encoding a fusion protein which activates transcription in eukaryotic cells, the fusion protein comprising a first polypeptide which binds to a tet operator sequence either: (i) in the absence but not the presence of tetracycline or a tetracycline analogue or (ii) in the presence but not the absence of tetracycline or a tetracycline analogue, operatively linked to a heterologous second polypeptide which activates transcription in eukaryotic cells.

23. The host cell of claim 19, which is a mammalian cell.

24. The host cell of claim 23, which is a human cell.

25. The host cell of claim 19, which is a yeast, insect or fungal cell.

26. A method for inhibiting transcription of a nucleotide sequence operatively linked to the at least one tet operator sequence in the host cell of claim 19 in vitro, comprising decreasing the concentration of tetracycline or a tetracycline analogue that is in contact with the host cell in vitro.

27. A recombinant vector comprising the nucleic acid molecule of claim 5 in a form suitable for expression of the fusion protein in a host cell.

28. A host cell comprising the recombinant vector of claim 27.

29. The host cell of claim 28, further comprising a nucleotide sequence to be transcribed operatively linked to at least one tet operator sequence.

30. The host cell of clam 29, wherein the nucleotide sequence to be transcribed is an exogenous nucleotide sequence introduced into the host cell.

31. The host cell of claim 29, wherein the nucleotide sequence to be transcribed is an endogenous nucleotide sequence to which at least one tet operator sequence has been operatively linked.

32. The host cell of claim 29, further comprising nucleic acid encoding a fusion protein which activates transcription in eukaryotic cells, the fusion protein comprising a first polypeptide which binds to a tet operator sequence either (i) in the absence but not the presence of tetracycline or a tetracycline analogue or (ii) in the presence but not the absence of tetracycline or a tetracycline analogue, operatively linked to a heterologous second polypeptide which activates transcription in eukaryotic cells.

33. The host cell of claim 29, which is a mammalian cell.

34. The host cell of claim 33, which is a human cell.

35. The host cell of claim 29, which is a yeast, insect or fungal cell.

36. A method for inhibiting transcription of the nucleotide sequence operatively linked to the at least one tet operator sequence in the host cell of claim 29 in vitro, comprising increasing the concentration of tetracycline or a tetracycline analogue that is in contact with the host cell in vitro.

37. A recombinant vector suitable for homologous recombination comprising the nucleic acid of claim 1, wherein the nucleic acid encoding the fusion protein is flanked at its 5' and 3' ends by additional nucleic acid of a eukaryotic gene, the additional nucleic acid being of sufficient length for successful homologous recombination with the eukaryotic gene.

38. The recombinant vector of claim 17, wherein expression of the fusion protein is regulated by at least one tet operator sequence.

39. The recombinant vector of claim 17, wherein expression of the fusion protein is regulated by at least one virally-derived regulatory element.

40. The recombinant vector of claim 17, wherein expression of the fusion protein is regulated by at least one tissue specific regulatory element.

41. The host cell of claim 19, which is a plant.

42. The recombinant vector of claim 27, wherein expression of the fusion protein is regulated by at least one tet operator sequence.

43. The recombinant vector of claim 27, wherein expression of the fusion protein is regulated by at least one virally-derived regulatory element.

44. The recombinant vector of claim 27, wherein expression of the fusion protein is regulated by at least one tissue specific regulatory element.

45. The host cell of claim 29, which is a plant.

46. A kit comprising a carrier means having in close confinement therein at least two container means comprising:

a) a first container means containing a first nucleic acid encoding a fusion protein which inhibits transcription in eukaryotic cells, the fusion protein comprising a first polypeptide which binds to tet operator sequences either (I) in the presence but not the absence of tetracycline or a tetracycline analogue or (ii) in the absence but not the presence of tetracycline or a tetracycline analogue, operatively linked to a heterologous second polypeptide which inhibits transcription in eukaryotic cells, or a eukaryotic cell line into which said first nucleic acid has been stably introduced; and b) a second container means containing a second nucleic acid comprising a cloning site for introduction of a nucleotide sequence to be transcribed operatively linked to at least one tet operator sequence.

47. The kit of claim 46, further comprising:

c) a third container means containing a third nucleic acid encoding a fusion protein which activates transcription in eukaryotic cells, the fusion protein comprising a first polypeptide which binds to tet operator sequences either (i) in the presence but not the absence of tetracycline or a tetracycline analogue or (ii) in the absence but not the presence of tetracycline or a tetracycline analogue, operatively linked to a heterologous second polypeptide which activates transcription in eukaryotic cells.

48. The kit of claim 46, wherein the eukaryotic cell line into which the first nucleic acid has been introduced further contains nucleic acid encoding a fusion protein which activates transcription in eukaryotic cells, the fusion protein comprising a first polypeptide which binds to tet operator sequences either (i) in the presence but not the absence of tetracycline or a tetracycline analogue or (ii) in the absence but not the presence of tetracycline or a tetracycline analogue, operatively linked to a heterologous second polypeptide which activates transcription in eukaryotic cells.

49. The kit of claim 46, further comprising a third container means containing a tetracycline or a tetracycline analogue.

* * * * *

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 1008 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
        ( A ) NAME/KEY: exon
        ( B ) LOCATION: 1..1008

( i x ) FEATURE:
        ( A ) NAME/KEY: mRNA
        ( B ) LOCATION: 1..1008

( i x ) FEATURE:
        ( A ) NAME/KEY: misc. binding
        ( B ) LOCATION: 1..207

( i x ) FEATURE:
        ( A ) NAME/KEY: misc. binding
        ( B ) LOCATION: 208..335

( i x ) FEATURE:
        ( A ) NAME/KEY: CDS
        ( B ) LOCATION: 1..1005

( x i ) SEQUENCE DESCRIPTION: SEQ ID NO:1:

```
ATG TCT AGA TTA GAT AAA AGT AAA GTG ATT AAC AGC GCA TTA GAG CTG      48
Met Ser Arg Leu Asp Lys Ser Lys Val Ile Asn Ser Ala Leu Glu Leu
 1               5                  10                  15

CTT AAT GAG GTC GGA ATC GAA GGT TTA ACA ACC CGT AAA CTC GCC CAG      96
Leu Asn Glu Val Gly Ile Glu Gly Leu Thr Thr Arg Lys Leu Ala Gln
            20                  25                  30

AAG CTA GGT GTA GAG CAG CCT ACA CTG TAT TGG CAT GTA AAA AAT AAG     144
Lys Leu Gly Val Glu Gln Pro Thr Leu Tyr Trp His Val Lys Asn Lys
        35                  40                  45

CGG GCT TTG CTC GAC GCC TTA GCC ATT GAG ATG TTA GAT AGG CAC CAT     192
Arg Ala Leu Leu Asp Ala Leu Ala Ile Glu Met Leu Asp Arg His His
    50                  55                  60

ACT CAC TTT TGC CCT TTA AAA GGG GAA AGC TGG CAA GAT TTT TTA CGC     240
Thr His Phe Cys Pro Leu Lys Gly Glu Ser Trp Gln Asp Phe Leu Arg
65                  70                  75                  80

AAT AAG GCT AAA AGT TTT AGA TGT GCT TTA CTA AGT CAT CGC AAT GGA     288
Asn Lys Ala Lys Ser Phe Arg Cys Ala Leu Leu Ser His Arg Asn Gly
                85                  90                  95

GCA AAA GTA CAT TCA GAT ACA CGG CCT ACA GAA AAA CAG TAT GAA ACT     336
Ala Lys Val His Ser Asp Thr Arg Pro Thr Glu Lys Gln Tyr Glu Thr
            100                 105                 110

CTC GAA AAT CAA TTA GCC TTT TTA TGC CAA CAA GGT TTT TCA CTA GAG     384
Leu Glu Asn Gln Leu Ala Phe Leu Cys Gln Gln Gly Phe Ser Leu Glu
        115                 120                 125

AAT GCA TTA TAT GCA CTC AGC GCT GTG GGG CAT TTT ACT TTA GGT TGC     432
Asn Ala Leu Tyr Ala Leu Ser Ala Val Gly His Phe Thr Leu Gly Cys
    130                 135                 140

GTA TTG GAA GAT CAA GAG CAT CAA GTC GCT AAA GAA GAA AGG GAA ACA     480
Val Leu Glu Asp Gln Glu His Gln Val Ala Lys Glu Glu Arg Glu Thr
145                 150                 155                 160
```

| | | | | | | | | | | | | | | | | |
|---|---|---|---|---|---|---|---|---|---|---|---|---|---|---|---|---|
| CCT | ACT | ACT | GAT | AGT | ATG | CCG | CCA | TTA | TTA | CGA | CAA | GCT | ATC | GAA | TTA | 528 |
| Pro | Thr | Thr | Asp | Ser | Met | Pro | Pro | Leu | Leu | Arg | Gln | Ala | Ile | Glu | Leu | |
| | | | | 165 | | | | | 170 | | | | | 175 | | |
| TTT | GAT | CAC | CAA | GGT | GCA | GAG | CCA | GCC | TTC | TTA | TTC | GGC | CTT | GAA | TTG | 576 |
| Phe | Asp | His | Gln | Gly | Ala | Glu | Pro | Ala | Phe | Leu | Phe | Gly | Leu | Glu | Leu | |
| | | | 180 | | | | | 185 | | | | | 190 | | | |
| ATC | ATA | TGC | GGA | TTA | GAA | AAA | CAA | CTT | AAA | TGT | GAA | AGT | GGG | TCC | GCG | 624 |
| Ile | Ile | Cys | Gly | Leu | Glu | Lys | Gln | Leu | Lys | Cys | Glu | Ser | Gly | Ser | Ala | |
| | | 195 | | | | | 200 | | | | | 205 | | | | |
| TAC | AGC | CGC | GCG | CGT | ACG | AAA | AAC | AAT | TAC | GGG | TCT | ACC | ATC | GAG | GGC | 672 |
| Tyr | Ser | Arg | Ala | Arg | Thr | Lys | Asn | Asn | Tyr | Gly | Ser | Thr | Ile | Glu | Gly | |
| | 210 | | | | | 215 | | | | | 220 | | | | | |
| CTG | CTC | GAT | CTC | CCG | GAC | GAC | GAC | GCC | CCC | GAA | GAG | GCG | GGG | CTG | GCG | 720 |
| Leu | Leu | Asp | Leu | Pro | Asp | Asp | Asp | Ala | Pro | Glu | Glu | Ala | Gly | Leu | Ala | |
| 225 | | | | | 230 | | | | | 235 | | | | | 240 | |
| GCT | CCG | CGC | CTG | TCC | TTT | CTC | CCC | GCG | GGA | CAC | ACG | CGC | AGA | CTG | TCG | 768 |
| Ala | Pro | Arg | Leu | Ser | Phe | Leu | Pro | Ala | Gly | His | Thr | Arg | Arg | Leu | Ser | |
| | | | | 245 | | | | | 250 | | | | | 255 | | |
| ACG | GCC | CCC | CCG | ACC | GAT | GTC | AGC | CTG | GGG | GAC | GAG | CTC | CAC | TTA | GAC | 816 |
| Thr | Ala | Pro | Pro | Thr | Asp | Val | Ser | Leu | Gly | Asp | Glu | Leu | His | Leu | Asp | |
| | | | 260 | | | | | 265 | | | | | 270 | | | |
| GGC | GAG | GAC | GTG | GCG | ATG | GCG | CAT | GCC | GAC | GCG | CTA | GAC | GAT | TTC | GAT | 864 |
| Gly | Glu | Asp | Val | Ala | Met | Ala | His | Ala | Asp | Ala | Leu | Asp | Asp | Phe | Asp | |
| | | 275 | | | | | 280 | | | | | 285 | | | | |
| CTG | GAC | ATG | TTG | GGG | GAC | GGG | GAT | TCC | CCG | GGT | CCG | GGA | TTT | ACC | CCC | 912 |
| Leu | Asp | Met | Leu | Gly | Asp | Gly | Asp | Ser | Pro | Gly | Pro | Gly | Phe | Thr | Pro | |
| | 290 | | | | | 295 | | | | | 300 | | | | | |
| CAC | GAC | TCC | GCC | CCC | TAC | GGC | GCT | CTG | GAT | ATG | GCC | GAC | TTC | GAG | TTT | 960 |
| His | Asp | Ser | Ala | Pro | Tyr | Gly | Ala | Leu | Asp | Met | Ala | Asp | Phe | Glu | Phe | |
| 305 | | | | | 310 | | | | | 315 | | | | | 320 | |
| GAG | CAG | ATG | TTT | ACC | GAT | CCC | CTT | GGA | ATT | GAC | GAG | TAC | GGT | GGG | TAG | 1008 |
| Glu | Gln | Met | Phe | Thr | Asp | Pro | Leu | Gly | Ile | Asp | Glu | Tyr | Gly | Gly | | |
| | | | | 325 | | | | | 330 | | | | | 335 | | |

( 2 ) INFORMATION FOR SEQ ID NO:2:

( i ) SEQUENCE CHARACTERISTICS:
        ( A ) LENGTH: 335 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ser | Arg | Leu | Asp | Lys | Ser | Lys | Val | Ile | Asn | Ser | Ala | Leu | Glu | Leu |
| 1 | | | | 5 | | | | | 10 | | | | | 15 | |
| Leu | Asn | Glu | Val | Gly | Ile | Glu | Gly | Leu | Thr | Thr | Arg | Lys | Leu | Ala | Gln |
| | | | | 20 | | | | | 25 | | | | | 30 | |
| Lys | Leu | Gly | Val | Glu | Gln | Pro | Thr | Leu | Tyr | Trp | His | Val | Lys | Asn | Lys |
| | | | 35 | | | | | 40 | | | | | 45 | | |
| Arg | Ala | Leu | Leu | Asp | Ala | Leu | Ala | Ile | Glu | Met | Leu | Asp | Arg | His | His |
| | | 50 | | | | | 55 | | | | | 60 | | | |
| Thr | His | Phe | Cys | Pro | Leu | Lys | Gly | Glu | Ser | Trp | Gln | Asp | Phe | Leu | Arg |
| 65 | | | | | 70 | | | | | 75 | | | | | 80 |
| Asn | Lys | Ala | Lys | Ser | Phe | Arg | Cys | Ala | Leu | Leu | Ser | His | Arg | Asn | Gly |
| | | | | 85 | | | | | 90 | | | | | 95 | |
| Ala | Lys | Val | His | Ser | Asp | Thr | Arg | Pro | Thr | Glu | Lys | Gln | Tyr | Glu | Thr |
| | | | 100 | | | | | 105 | | | | | 110 | | |
| Leu | Glu | Asn | Gln | Leu | Ala | Phe | Leu | Cys | Gln | Gln | Gly | Phe | Ser | Leu | Glu |
| | | | 115 | | | | | 120 | | | | | 125 | | |

```
Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
        260                 265                 270

Gly Glu Asp Val Ala Met Ala His Ala Asp Ala Leu Asp Asp Phe Asp
        275                 280                 285

Leu Asp Met Leu Gly Asp Gly Asp Ser Pro Gly Pro Gly Phe Thr Pro
    290                 295                 300

His Asp Ser Ala Pro Tyr Gly Ala Leu Asp Met Ala Asp Phe Glu Phe
305                 310                 315                 320

Glu Gln Met Phe Thr Asp Pro Leu Gly Ile Asp Glu Tyr Gly Gly
                325                 330                 335
```

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:3:

```
GAC GCG CTA GAC GAT TTC GAT CTG GAC ATG TTG                    33
Asp Ala Leu Asp Asp Phe Asp Leu Asp Met Leu
 1           5                   10
```

(2) INFORMATION FOR SEQ ID NO:4:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:4:

```
Asp Ala Leu Asp Asp Phe Asp Leu Asp Met Leu
 1           5                   10
```

(2) INFORMATION FOR SEQ ID NO:5:

(i) SEQUENCE CHARACTERISTICS:
        (A) LENGTH: 7 amino acids
        (B) TYPE: amino acid
        (D) TOPOLOGY: linear ( i i ) MOLECULE TYPE: peptide ( v ) FRAGMENT TYPE: internal ( x i ) SEQUENCE DESCRIPTION: SEQ ID NO:5:

```
Met Pro Lys Arg Pro Arg Pro
 1               5
```

( 2 ) INFORMATION FOR SEQ ID NO:6:

( i ) SEQUENCE CHARACTERISTICS:
        ( A ) LENGTH: 569 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:6:

```
GAATTCGGGG CCGCGGAGGC TGGATCGGTC CCGGTGTCTT CTATGGAGGT CAAAACAGCG      60
TGGATGGCGT CTCCAGGCGA TCTGACGGTT CACTAAACGA GCTCTGCTTA TATAGGTCGA     120
GTTACCACT  CCCTATCAGT GATAGAGAAA AGTGAAAGTC GAGTTTACCA CTCCCTATCA     180
GTGATAGAGA AAAGTGAAAG TCGAGTTTAC CACTCCCTAT CAGTGATAGA GAAAAGTGAA     240
AGTCGAGTTT ACCACTCCCT ACCAGTGATA GAGAAAAGTG AAAGTCGAGT TTACCACTCC     300
CTATCAGTGA TAGAGAAAAG TGAAAGTCGA GTTACCACT  CCCTATCAGT GATAGAGAAA     360
AGTGAAAGTC GAGTTTACCA CTCCCTATCA GTGATAGAGA AAAGTGAAAG TCGAGCTCGG     420
TACCCGGGTC GAGTAGGCGT GTACGGTGGG AGGCCTATAT AAGCAGAGCT CGTTTAGTGA     480
ACCGTCAGAT CGCCTGGAGA CGCCATCCAC GCTGTTTTGA CCTCCATAGA AGACACCGGG     540
ACCGATCCAG CCTCCGCGGC CCCGAATTC                                      569
```

( 2 ) INFORMATION FOR SEQ ID NO:7:

( i ) SEQUENCE CHARACTERISTICS:
        ( A ) LENGTH: 520 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:7:

```
AGATCTGCAG GGTCGCTCGG TGTTCGAGGC CACACGCGTC ACCTTAATAT GCGAAGTGGA      60
CCGGATCTCG AGTTTACCAC TCCCTATCAG TGATAGAGAA AAGTGAAAGT CGAGTTTACC     120
ACTCCCTATC AGTGATAGAG AAAAGTGAAA GTCGAGTTTA CCACTCCCTA TCAGTGATAG     180
AGAAAAGTGA AAGTCGAGTT TACCACTCCC TATCAGTGAT AGAGAAAAGT GAAAGTCGAG     240
TTTACCACTC CCTATCAGTG ATAGAGAAAA GTGAAAGTCG AGTTACCAC  TCCCTATCAG     300
TGATAGAGAA AAGTGAAAGT CGAGTTTACC ACTCCCTATC AGTGATAGAG AAAAGTGAAA     360
GTCGAGCTCG GTACCCGGGT CGAGTAGGCG TGTACGGTGG GAGGCCTATA TAAGCAGAGC     420
TCGTTTAGTG AACCGTCAGA TCGCCTGGAG ACGCCATCCA CGCTGTTTTG ACCTCCATAG     480
AAGACACCGG GACCGATCCA GCCTCCGCGG CCCCGAATTC                           520
```

( 2 ) INFORMATION FOR SEQ ID NO:8:

( i ) SEQUENCE CHARACTERISTICS:
        ( A ) LENGTH: 450 base pairs
        ( B ) TYPE: nucleic acid ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Human cytomegalovirus
        ( B ) STRAIN: K12, Towne ( i x ) FEATURE:
        ( A ) NAME/KEY: mRNA
        ( B ) LOCATION: 382..450

( x i ) SEQUENCE DESCRIPTION: SEQ ID NO:8:

| | | | | | | |
|---|---|---|---|---|---|---|
| GAATTCCTCG | AGTTTACCAC | TCCCTATCAG | TGATAGAGAA | AAGTGAAAGT | CGAGTTTACC | 60 |
| ACTCCCTATC | AGTGATAGAG | AAAAGTGAAA | GTCGAGTTTA | CCACTCCCTA | TCAGTGATAG | 120 |
| AGAAAAGTGA | AAGTCGAGTT | TACCACTCCC | TATCAGTGAT | AGAGAAAAGT | GAAAGTCGAG | 180 |
| TTTACCACTC | CCTATCAGTG | ATAGAGAAAA | GTGAAAGTCG | AGTTACCAC | TCCCTATCAG | 240 |
| TGATAGAGAA | AAGTGAAAGT | CGAGTTTACC | ACTCCCTATC | AGTGATAGAG | AAAAGTGAAA | 300 |
| GTCGAGCTCG | GTACCCGGGT | CGAGTAGGCG | TGTACGGTGG | GAGGCCTATA | TAAGCAGAGC | 360 |
| TCGTTTAGTG | AACCGTCAGA | TCGCCTGGAG | ACGCCATCCA | CGCTGTTTTG | ACCTCCATAG | 420 |
| AAGACACCGG | GACCGATCCA | GCCTCCGCGG | | | | 450 |

( 2 ) INFORMATION FOR SEQ ID NO:9:

( i ) SEQUENCE CHARACTERISTICS:
        ( A ) LENGTH: 450 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Human cytomegalovirus
        ( B ) STRAIN: Towne ( i x ) FEATURE:
        ( A ) NAME/KEY: mRNA
        ( B ) LOCATION: 382..450

( x i ) SEQUENCE DESCRIPTION: SEQ ID NO:9:

| | | | | | | |
|---|---|---|---|---|---|---|
| GAATTCCTCG | ACCCGGGTAC | CGAGCTCGAC | TTTCACTTTT | CTCTATCACT | GATAGGGAGT | 60 |
| GGTAAACTCG | ACTTTCACTT | TTCTCTATCA | CTGATAGGGA | GTGGTAAACT | CGACTTTCAC | 120 |
| TTTTCTCTAT | CACTGATAGG | GAGTGGTAAA | CTCGACTTTC | ACTTTTCTCT | ATCACTGATA | 180 |
| GGGAGTGGTA | AACTCGACTT | TCACTTTTCT | CTATCACTGA | TAGGGAGTGG | TAAACTCGAC | 240 |
| TTTCACTTTT | CTCTATCACT | GATAGGGAGT | GGTAAACTCG | ACTTTCACTT | TTCTCTATCA | 300 |
| CTGATAGGGA | GTGGTAAACT | CGAGTAGGCG | TGTACGGTGG | GAGGCCTATA | TAAGCAGAGC | 360 |
| TCGTTTAGTG | AACCGTCAGA | TCGCCTGGAG | ACGCCATCCA | CGCTGTTTTG | ACCTCCATAG | 420 |
| AAGACACCGG | GACCGATCCA | GCCTCCGCGG | | | | 450 |

( 2 ) INFORMATION FOR SEQ ID NO:10:

( i ) SEQUENCE CHARACTERISTICS:
        ( A ) LENGTH: 398 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:

(A) ORGANISM: Herpes Simplex Virus
(B) STRAIN: KOS (xi) SEQUENCE DESCRIPTION: SEQ ID NO:10:

| | | | | | | |
|---|---|---|---|---|---|---|
| GAGCTCGACT | TTCACTTTTC | TCTATCACTG | ATAGGGAGTG | GTAAACTCGA | CTTTCACTTT | 60 |
| TCTCTATCAC | TGATAGGGAG | TGGTAAACTC | GACTTTCACT | TTTCTATC | ACTGATAGGG | 120 |
| AGTGGTAAAC | TCGACTTTCA | CTTTTCTCTA | TCACTGATAG | GGAGTGGTAA | ACTCGACTTT | 180 |
| CACTTTTCTC | TATCACTGAT | AGGGAGTGGT | AAACTCGACT | TTCACTTTTC | TCTATCACTG | 240 |
| ATAGGGAGTG | GTAAACTCGA | CTTTCACTTT | TCTCTATCAC | TGATAGGGAG | TGGTAAACTC | 300 |
| GAGATCCGGC | GAATTCGAAC | ACGCAGATGC | AGTCGGGGCG | GCGCGGTCCG | AGGTCCACTT | 360 |
| CGCATATTAA | GGTGACGCGT | GTGGCCTCGA | ACACCGAG | | | 398 |

(2) INFORMATION FOR SEQ ID NO:11:

(i) SEQUENCE CHARACTERISTICS:
(A) LENGTH: 38 base pairs
(B) TYPE: nucleic acid
(C) STRANDEDNESS: double
(D) TOPOLOGY: linear (ii) MOLECULE TYPE: DNA (xi) SEQUENCE DESCRIPTION: SEQ ID NO:11:

ACTTTATCAC TGATAAACAA ACTTATCAGT GATAAAGA                38

(2) INFORMATION FOR SEQ ID NO:12:

(i) SEQUENCE CHARACTERISTICS:
(A) LENGTH: 38 base pairs
(B) TYPE: nucleic acid
(C) STRANDEDNESS: double
(D) TOPOLOGY: linear (ii) MOLECULE TYPE: DNA (xi) SEQUENCE DESCRIPTION: SEQ ID NO:12:

ACTCTATCAT TGATAGAGTT CCCTATCAGT GATAGAGA                38

(2) INFORMATION FOR SEQ ID NO:13:

(i) SEQUENCE CHARACTERISTICS:
(A) LENGTH: 38 base pairs
(B) TYPE: nucleic acid
(C) STRANDEDNESS: double
(D) TOPOLOGY: linear (ii) MOLECULE TYPE: DNA (xi) SEQUENCE DESCRIPTION: SEQ ID NO:13:

AGCTTATCAT CGATAAGCTA GTTTATCACA GTTAAATT                38

(2) INFORMATION FOR SEQ ID NO:14:

(i) SEQUENCE CHARACTERISTICS:
(A) LENGTH: 38 base pairs
(B) TYPE: nucleic acid
(C) STRANDEDNESS: double
(D) TOPOLOGY: linear (ii) MOLECULE TYPE: DNA (xi) SEQUENCE DESCRIPTION: SEQ ID NO:14:

ACTCTATCAT TGATAGGGAA CTCTATCAAT GATAGGGA                38

( 2 ) INFORMATION FOR SEQ ID NO:15:

( i ) SEQUENCE CHARACTERISTICS:
        ( A ) LENGTH: 38 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:15:

AATCTATCAC TGATAGAGTA CCCTATCATC GATAGAGA     38

( 2 ) INFORMATION FOR SEQ ID NO:16:

( i ) SEQUENCE CHARACTERISTICS:
        ( A ) LENGTH: 621 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:16:

```
ATG TCT AGA TTA GAT AAA AGT AAA GTG ATT AAC AGC GCA TTA GAG CTG      48
Met Ser Arg Leu Asp Lys Ser Lys Val Ile Asn Ser Ala Leu Glu Leu
 1               5                  10                  15

CTT AAT GAG GTC GGA ATC GAA GGT TTA ACA ACC CGT AAA CTC GCC CAG      96
Leu Asn Glu Val Gly Ile Glu Gly Leu Thr Thr Arg Lys Leu Ala Gln
             20                  25                  30

AAG CTA GGT GTA GAG CAG CCT ACA TTG TAT TGG CAT GTA AAA AAT AAG     144
Lys Leu Gly Val Glu Gln Pro Thr Leu Tyr Trp His Val Lys Asn Lys
         35                  40                  45

CGG GCT TTG CTC GAC GCC TTA GCC ATT GAG ATG TTA GAT AGG CAC CAT     192
Arg Ala Leu Leu Asp Ala Leu Ala Ile Glu Met Leu Asp Arg His His
     50                  55                  60

ACT CAC TTT TGC CCT TTA GAA GGG GAA AGC TGG CAA GAT TTT TTA CGT     240
Thr His Phe Cys Pro Leu Glu Gly Glu Ser Trp Gln Asp Phe Leu Arg
 65                  70                  75                  80

AAT AAG GCT AAA AGT TTT AGA TGT GCT TTA CTA AGT CAT CGC GAT GGA     288
Asn Lys Ala Lys Ser Phe Arg Cys Ala Leu Leu Ser His Arg Asp Gly
                 85                  90                  95

GCA AAA GTA CAT TTA GGT ACA CGG CCT ACA GAA AAA CAG TAT GAA ACT     336
Ala Lys Val His Leu Gly Thr Arg Pro Thr Glu Lys Gln Tyr Glu Thr
            100                 105                 110

CTC GAA AAT CAA TTA GCC TTT TTA TGC CAA CAA GGT TTT TCA CTA GAG     384
Leu Glu Asn Gln Leu Ala Phe Leu Cys Gln Gln Gly Phe Ser Leu Glu
        115                 120                 125

AAT GCA TTA TAT GCA CTC AGC GCT GTG GGG CAT TTT ACT TTA GGT TGC     432
Asn Ala Leu Tyr Ala Leu Ser Ala Val Gly His Phe Thr Leu Gly Cys
    130                 135                 140

GTA TTG GAA GAT CAA GAG CAT CAA GTC GCT AAA GAA GAA AGG GAA ACA     480
Val Leu Glu Asp Gln Glu His Gln Val Ala Lys Glu Glu Arg Glu Thr
145                 150                 155                 160

CCT ACT ACT GAT AGT ATG CCG CCA TTA TTA CGA CAA GCT ATC GAA TTA     528
Pro Thr Thr Asp Ser Met Pro Pro Leu Leu Arg Gln Ala Ile Glu Leu
                165                 170                 175

TTT GAT CAC CAA GGT GCA GAG CCA GCC TTC TTA TTC GGC CTT GAA TTG     576
Phe Asp His Gln Gly Ala Glu Pro Ala Phe Leu Phe Gly Leu Glu Leu
            180                 185                 190

ATC ATA TGC GGA TTA GAA AAA CAA CTT AAA TGT GAA AGT GGG TCC         621
Ile Ile Cys Gly Leu Glu Lys Gln Leu Lys Cys Glu Ser Gly Ser
        195                 200                 205
```

( 2 ) INFORMATION FOR SEQ ID NO:17:

(i) SEQUENCE CHARACTERISTICS:
 (A) LENGTH: 207 amino acids
 (B) TYPE: amino acid
 (D) TOPOLOGY: linear (ii) MOLECULE TYPE: protein (xi) SEQUENCE DESCRIPTION: SEQ ID NO:17:

```
Met Ser Arg Leu Asp Lys Ser Lys Val Ile Asn Ser Ala Leu Glu Leu
  1               5                  10                  15
Leu Asn Glu Val Gly Ile Glu Gly Leu Thr Thr Arg Lys Leu Ala Gln
                 20                  25                  30
Lys Leu Gly Val Glu Gln Pro Thr Leu Tyr Trp His Val Lys Asn Lys
             35                  40                  45
Arg Ala Leu Leu Asp Ala Leu Ala Ile Glu Met Leu Asp Arg His His
         50                  55                  60
Thr His Phe Cys Pro Leu Glu Gly Glu Ser Trp Gln Asp Phe Leu Arg
 65                  70                  75                  80
Asn Lys Ala Lys Ser Phe Arg Cys Ala Leu Leu Ser His Arg Asp Gly
                 85                  90                  95
Ala Lys Val His Leu Gly Thr Arg Pro Thr Glu Lys Gln Tyr Glu Thr
             100                 105                 110
Leu Glu Asn Gln Leu Ala Phe Leu Cys Gln Gln Gly Phe Ser Leu Glu
         115                 120                 125
Asn Ala Leu Tyr Ala Leu Ser Ala Val Gly His Phe Thr Leu Gly Cys
     130                 135                 140
Val Leu Glu Asp Gln Glu His Gln Val Ala Lys Glu Glu Arg Glu Thr
145                 150                 155                 160
Pro Thr Thr Asp Ser Met Pro Pro Leu Leu Arg Gln Ala Ile Glu Leu
                165                 170                 175
Phe Asp His Gln Gly Ala Glu Pro Ala Phe Leu Phe Gly Leu Glu Leu
            180                 185                 190
Ile Ile Cys Gly Leu Glu Lys Gln Leu Lys Cys Glu Ser Gly Ser
        195                 200                 205
```

( 2 ) INFORMATION FOR SEQ ID NO:18:

(i) SEQUENCE CHARACTERISTICS:
 (A) LENGTH: 621 base pairs
 (B) TYPE: nucleic acid
 (C) STRANDEDNESS: double
 (D) TOPOLOGY: linear (ii) MOLECULE TYPE: cDNA (xi) SEQUENCE DESCRIPTION: SEQ ID NO:18:

```
ATG TCT AGA TTA GAT AAA AGT AAA GTG ATT AAC AGC GCA TTA GAG CTG    48
Met Ser Arg Leu Asp Lys Ser Lys Val Ile Asn Ser Ala Leu Glu Leu
  1               5                  10                  15

CTT AAT GAG GTC GGA ATC GAA GGT TTA ACA ACC CGT AAA CTC GCC CAG    96
Leu Asn Glu Val Gly Ile Glu Gly Leu Thr Thr Arg Lys Leu Ala Gln
                 20                  25                  30

AAG CTA GGT GTA GAG CAG CCT ACA CTG TAT TGG CAT GTA AAA AAT AAG   144
Lys Leu Gly Val Glu Gln Pro Thr Leu Tyr Trp His Val Lys Asn Lys
             35                  40                  45

CGG GCT TTG CTC GAC GCC TTA GCC ATT GAG ATG TTA GAT AGG CAC CAT   192
Arg Ala Leu Leu Asp Ala Leu Ala Ile Glu Met Leu Asp Arg His His
         50                  55                  60

ACT CAC TTT TGC CCT TTA AAA GGG GAA AGC TGG CAA GAT TTT TTA CGC   240
```

| | | | | | | | | | | | | | | | | |
|---|---|---|---|---|---|---|---|---|---|---|---|---|---|---|---|---|
| Thr | His | Phe | Cys | Pro | Leu | Lys | Gly | Glu | Ser | Trp | Gln | Asp | Phe | Leu | Arg | |
| 65 | | | | 70 | | | | | 75 | | | | | | 80 | |

| | | | | | | | | | | | | | | | | |
|---|---|---|---|---|---|---|---|---|---|---|---|---|---|---|---|---|
| AAT | AAG | GCT | AAA | AGT | TTT | AGA | TGT | GCT | TTA | CTA | AGT | CAT | CGC | AAT | GGA | 288 |
| Asn | Lys | Ala | Lys | Ser | Phe | Arg | Cys | Ala | Leu | Leu | Ser | His | Arg | Asn | Gly | |
| | | | | 85 | | | | | 90 | | | | | 95 | | |
| GCA | AAA | GTA | CAT | TCA | GAT | ACA | CGG | CCT | ACA | GAA | AAA | CAG | TAT | GAA | ACT | 336 |
| Ala | Lys | Val | His | Ser | Asp | Thr | Arg | Pro | Thr | Glu | Lys | Gln | Tyr | Glu | Thr | |
| | | | 100 | | | | | 105 | | | | | 110 | | | |
| CTC | GAA | AAT | CAA | TTA | GCC | TTT | TTA | TGC | CAA | CAA | GGT | TTT | TCA | CTA | GAG | 384 |
| Leu | Glu | Asn | Gln | Leu | Ala | Phe | Leu | Cys | Gln | Gln | Gly | Phe | Ser | Leu | Glu | |
| | | 115 | | | | | 120 | | | | | 125 | | | | |
| AAT | GCA | TTA | TAT | GCA | CTC | AGC | GCT | GTG | GGG | CAT | TTT | ACT | TTA | GGT | TGC | 432 |
| Asn | Ala | Leu | Tyr | Ala | Leu | Ser | Ala | Val | Gly | His | Phe | Thr | Leu | Gly | Cys | |
| 130 | | | | | 135 | | | | | 140 | | | | | | |
| GTA | TTG | GAA | GAT | CAA | GAG | CAT | CAA | GTC | GCT | AAA | GAA | GAA | AGG | GAA | ACA | 480 |
| Val | Leu | Glu | Asp | Gln | Glu | His | Gln | Val | Ala | Lys | Glu | Glu | Arg | Glu | Thr | |
| 145 | | | | | 150 | | | | | 155 | | | | | 160 | |
| CCT | ACT | ACT | GAT | AGT | ATG | CCG | CCA | TTA | TTA | CGA | CAA | GCT | ATC | GAA | TTA | 528 |
| Pro | Thr | Thr | Asp | Ser | Met | Pro | Pro | Leu | Leu | Arg | Gln | Ala | Ile | Glu | Leu | |
| | | | | 165 | | | | | 170 | | | | | 175 | | |
| TTT | GAT | CAC | CAA | GGT | GCA | GAG | CCA | GCC | TTC | TTA | TTC | GGC | CTT | GAA | TTG | 576 |
| Phe | Asp | His | Gln | Gly | Ala | Glu | Pro | Ala | Phe | Leu | Phe | Gly | Leu | Glu | Leu | |
| | | | 180 | | | | | 185 | | | | | 190 | | | |
| ATC | ATA | TGC | GGA | TTA | GAA | AAA | CAA | CTT | AAA | TGT | GAA | AGT | GGG | TCC | | 621 |
| Ile | Ile | Cys | Gly | Leu | Glu | Lys | Gln | Leu | Lys | Cys | Glu | Ser | Gly | Ser | | |
| | | 195 | | | | | 200 | | | | | 205 | | | | |

( 2 ) INFORMATION FOR SEQ ID NO:19:

( i ) SEQUENCE CHARACTERISTICS:
        ( A ) LENGTH: 207 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

| | | | | | | | | | | | | | | | |
|---|---|---|---|---|---|---|---|---|---|---|---|---|---|---|---|
| Met | Ser | Arg | Leu | Asp | Lys | Ser | Lys | Val | Ile | Asn | Ser | Ala | Leu | Glu | Leu |
| 1 | | | | 5 | | | | | 10 | | | | | 15 | |
| Leu | Asn | Glu | Val | Gly | Ile | Glu | Gly | Leu | Thr | Thr | Arg | Lys | Leu | Ala | Gln |
| | | | 20 | | | | | 25 | | | | | 30 | | |
| Lys | Leu | Gly | Val | Glu | Gln | Pro | Thr | Leu | Tyr | Trp | His | Val | Lys | Asn | Lys |
| | | 35 | | | | | 40 | | | | | 45 | | | |
| Arg | Ala | Leu | Leu | Asp | Ala | Leu | Ala | Ile | Glu | Met | Leu | Asp | Arg | His | His |
| | 50 | | | | | 55 | | | | | 60 | | | | |
| Thr | His | Phe | Cys | Pro | Leu | Lys | Gly | Glu | Ser | Trp | Gln | Asp | Phe | Leu | Arg |
| 65 | | | | 70 | | | | | 75 | | | | | | 80 |
| Asn | Lys | Ala | Lys | Ser | Phe | Arg | Cys | Ala | Leu | Leu | Ser | His | Arg | Asn | Gly |
| | | | | 85 | | | | | 90 | | | | | 95 | |
| Ala | Lys | Val | His | Ser | Asp | Thr | Arg | Pro | Thr | Glu | Lys | Gln | Tyr | Glu | Thr |
| | | | 100 | | | | | 105 | | | | | 110 | | |
| Leu | Glu | Asn | Gln | Leu | Ala | Phe | Leu | Cys | Gln | Gln | Gly | Phe | Ser | Leu | Glu |
| | | 115 | | | | | 120 | | | | | 125 | | | |
| Asn | Ala | Leu | Tyr | Ala | Leu | Ser | Ala | Val | Gly | His | Phe | Thr | Leu | Gly | Cys |
| 130 | | | | | 135 | | | | | 140 | | | | | |
| Val | Leu | Glu | Asp | Gln | Glu | His | Gln | Val | Ala | Lys | Glu | Glu | Arg | Glu | Thr |
| 145 | | | | | 150 | | | | | 155 | | | | | 160 |
| Pro | Thr | Thr | Asp | Ser | Met | Pro | Pro | Leu | Leu | Arg | Gln | Ala | Ile | Glu | Leu |
| | | | | 165 | | | | | 170 | | | | | 175 | |

```
Phe  Asp  His  Gln  Gly  Ala  Glu  Pro  Ala  Phe  Leu  Phe  Gly  Leu  Glu  Leu
          180                     185                         190

Ile  Ile  Cys  Gly  Leu  Glu  Lys  Gln  Leu  Lys  Cys  Glu  Ser  Gly  Ser
          195                     200                         205
```

( 2 ) INFORMATION FOR SEQ ID NO:20:

( i ) SEQUENCE CHARACTERISTICS:
    ( A ) LENGTH: 192 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:20:

```
GAC  ATG  GAA  AAA  GCG  ACA  CCG  GAG  ACG  ATG  GTC  CAT  TGG  ATT  TGT  CTG     48
Asp  Met  Glu  Lys  Ala  Thr  Pro  Glu  Thr  Met  Val  His  Trp  Ile  Cys  Leu
1                    5                     10                      15

AAG  ATG  GAG  CCA  GCT  CTG  TGG  ATG  GCC  ATT  ACA  GCA  ACA  TCG  CAC  GGC     96
Lys  Met  Glu  Pro  Ala  Leu  Trp  Met  Ala  Ile  Thr  Ala  Thr  Ser  His  Gly
                20                     25                      30

GCA  AGG  CAC  AGG  ACA  TTC  GTC  GGG  TTT  TCC  GGC  TGC  CTC  CAC  CGC  AAA    144
Ala  Arg  His  Arg  Thr  Phe  Val  Gly  Phe  Ser  Gly  Cys  Leu  His  Arg  Lys
          35                     40                          45

TCC  CTC  ACG  TAC  CCA  GTG  ATA  TGC  CTG  AGC  AAA  CCG  AGC  CAG  AGG  ATT    192
Ser  Leu  Thr  Tyr  Pro  Val  Ile  Cys  Leu  Ser  Lys  Pro  Ser  Gln  Arg  Ile
     50                     55                     60
```

( 2 ) INFORMATION FOR SEQ ID NO:21:

( i ) SEQUENCE CHARACTERISTICS:
    ( A ) LENGTH: 64 amino acids
    ( B ) TYPE: amino acid
    ( D ) TOPOLOGY: linear ( i i ) MOLECULE TYPE: protein ( x i ) SEQUENCE DESCRIPTION: SEQ ID NO:21:

```
Asp  Met  Glu  Lys  Ala  Thr  Pro  Glu  Thr  Met  Val  His  Trp  Ile  Cys  Leu
1                    5                     10                      15

Lys  Met  Glu  Pro  Ala  Leu  Trp  Met  Ala  Ile  Thr  Ala  Thr  Ser  His  Gly
                20                     25                      30

Ala  Arg  His  Arg  Thr  Phe  Val  Gly  Phe  Ser  Gly  Cys  Leu  His  Arg  Lys
          35                     40                          45

Ser  Leu  Thr  Tyr  Pro  Val  Ile  Cys  Leu  Ser  Lys  Pro  Ser  Gln  Arg  Ile
     50                     55                     60
```

( 2 ) INFORMATION FOR SEQ ID NO:22:

( i ) SEQUENCE CHARACTERISTICS:
    ( A ) LENGTH: 816 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:22:

```
CTG  GAC  GAC  TCG  AAG  CGC  GTA  GCC  AAG  CGG  AAG  CTG  ATC  GAG  GAG  AAC     48
Leu  Asp  Asp  Ser  Lys  Arg  Val  Ala  Lys  Arg  Lys  Leu  Ile  Glu  Glu  Asn
1                    5                     10                      15

CGG  GAG  CGG  CGA  CGC  AAG  GAG  GAG  ATG  ATC  AAA  TCC  CTG  CAG  CAC  CGG     96
Arg  Glu  Arg  Arg  Arg  Lys  Glu  Glu  Met  Ile  Lys  Ser  Leu  Gln  His  Arg
                20                     25                      30
```

| | | | | | | | | | | | | | | | | |
|---|---|---|---|---|---|---|---|---|---|---|---|---|---|---|---|---|
| CCC | AGC | CCC | AGC | GCA | GAG | GAG | TGG | GAG | CTG | ATC | CAC | GTG | GTG | ACC | GAG | 144 |
| Pro | Ser | Pro 35 | Ser | Ala | Glu | Glu | Trp 40 | Glu | Leu | Ile | His | Val 45 | Val | Thr | Glu | |
| GCG | CAC | CGC | AGC | ACC | AAC | GCG | CAG | GGC | AGC | CAC | TGG | AAG | CAG | AGG | AGG | 192 |
| Ala | His 50 | Arg | Ser | Thr | Asn | Ala 55 | Gln | Gly | Ser | His | Trp 60 | Lys | Gln | Arg | Arg | |
| AAA | TTC | CTG | CTC | GAA | GAT | ATC | GGT | CAG | TCG | CCC | ATG | GCC | TCC | ATG | CTT | 240 |
| Lys 65 | Phe | Leu | Leu | Glu | Asp 70 | Ile | Gly | Gln | Ser | Pro 75 | Met | Ala | Ser | Met | Leu 80 | |
| GAC | GGG | GAC | AAA | GTG | GAC | CTG | GAG | GCG | TTC | AGC | GAG | TTT | ACA | AAA | ATC | 288 |
| Asp | Gly | Asp | Lys | Val 85 | Asp | Leu | Glu | Ala | Phe 90 | Ser | Glu | Phe | Thr | Lys 95 | Ile | |
| ATC | ACG | CCG | GCC | ATC | ACC | CGC | GTG | GTC | GAC | TTT | GCC | AAA | AAC | CTG | CCC | 336 |
| Ile | Thr | Pro | Ala 100 | Ile | Thr | Arg | Val | Val 105 | Asp | Phe | Ala | Lys | Asn 110 | Leu | Pro | |
| ATG | TTC | TCG | GAG | CTG | CCG | TGC | GAG | GAT | CAG | ATC | ATC | CTG | CTG | AAG | GGC | 384 |
| Met | Phe | Ser 115 | Glu | Leu | Pro | Cys | Glu 120 | Asp | Gln | Ile | Ile | Leu 125 | Leu | Lys | Gly | |
| TGC | TGC | ATG | GAG | ATC | ATG | TCG | CTG | CGC | GCC | GCC | GTG | CGC | TAC | GAC | CCC | 432 |
| Cys | Cys 130 | Met | Glu | Ile | Met | Ser 135 | Leu | Arg | Ala | Ala | Val 140 | Arg | Tyr | Asp | Pro | |
| GAG | AGC | GAA | ACG | CTG | ACG | CTG | AGC | GGG | GAA | ATG | GCC | GTC | AAA | CGC | GAG | 480 |
| Glu 145 | Ser | Glu | Thr | Leu | Thr 150 | Leu | Ser | Gly | Glu | Met 155 | Ala | Val | Lys | Arg | Glu 160 | |
| CAG | TTG | AAG | AAC | GGA | GGG | CTG | GGG | GTC | GTG | TCT | GAT | GCC | ATC | TTC | GAC | 528 |
| Gln | Leu | Lys | Asn | Gly 165 | Gly | Leu | Gly | Val | Val 170 | Ser | Asp | Ala | Ile | Phe 175 | Asp | |
| CTC | GGC | AAG | TCG | CTG | TCT | GCC | TTC | AAC | CTG | GAC | GAC | ACC | GAG | GTG | GCC | 576 |
| Leu | Gly | Lys | Ser 180 | Leu | Ser | Ala | Phe | Asn 185 | Leu | Asp | Asp | Thr | Glu 190 | Val | Ala | |
| CTG | CTG | CAG | GCC | GTG | CTG | CTC | ATG | TCC | TCA | GAC | CGG | ACG | GGG | CTG | ATC | 624 |
| Leu | Leu | Gln 195 | Ala | Val | Leu | Leu | Met 200 | Ser | Ser | Asp | Arg | Thr 205 | Gly | Leu | Ile | |
| TGC | GTG | GAT | AAG | ATA | GAG | AAG | TGC | CAG | GAG | TCG | TAC | CTG | CTG | GCG | TTC | 672 |
| Cys | Val | Asp 210 | Lys | Ile | Glu | Lys 215 | Cys | Gln | Glu | Ser | Tyr 220 | Leu | Leu | Ala | Phe | |
| GAG | CAC | TAC | ATC | AAC | TAC | CGC | AAA | CAC | AAC | ATT | CCC | CAC | TTC | TGG | TCC | 720 |
| Glu 225 | His | Tyr | Ile | Asn | Tyr 230 | Arg | Lys | His | Asn | Ile 235 | Pro | His | Phe | Trp | Ser 240 | |
| AAG | CTG | CTG | ATG | AAG | GTG | GCG | GAC | CTG | CGC | ATG | ATC | GGC | GCC | TAC | CAC | 768 |
| Lys | Leu | Leu | Met | Lys 245 | Val | Ala | Asp | Leu | Arg 250 | Met | Ile | Gly | Ala | Tyr 255 | His | |
| GCC | AGC | CGC | TTC | CTG | CAC | ATG | AAG | GTG | GAG | TGC | CCC | ACC | GAG | CTC | TCC | 816 |
| Ala | Ser | Arg | Phe 260 | Leu | His | Met | Lys | Val 265 | Glu | Cys | Pro | Thr | Glu 270 | Leu | Ser | |

( 2 ) INFORMATION FOR SEQ ID NO:23:

( i ) SEQUENCE CHARACTERISTICS:
        ( A ) LENGTH: 272 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

| | | | | | | | | | | | | | | |
|---|---|---|---|---|---|---|---|---|---|---|---|---|---|---|
| Leu 1 | Asp | Asp | Ser | Lys 5 | Arg | Val | Ala | Lys | Arg 10 | Lys | Leu | Ile | Glu | Glu Asn 15 |
| Arg | Glu | Arg | Arg 20 | Arg | Lys | Glu | Glu | Met 25 | Ile | Lys | Ser | Leu | Gln 30 | His Arg |
| Pro | Ser | Pro 35 | Ser | Ala | Glu | Glu | Trp 40 | Glu | Leu | Ile | His | Val 45 | Val | Thr Glu |

| | | | | | | | | | | | | | | |
|---|---|---|---|---|---|---|---|---|---|---|---|---|---|---|
| Ala | His | Arg | Ser | Thr | Asn | Ala | Gln | Gly | Ser | His | Trp | Lys | Gln | Arg | Arg |
| | 50 | | | | | 55 | | | | | 60 | | | | |
| Lys | Phe | Leu | Leu | Glu | Asp | Ile | Gly | Gln | Ser | Pro | Met | Ala | Ser | Met | Leu |
| 65 | | | | | 70 | | | | | 75 | | | | | 80 |
| Asp | Gly | Asp | Lys | Val | Asp | Leu | Glu | Ala | Phe | Ser | Glu | Phe | Thr | Lys | Ile |
| | | | | 85 | | | | | 90 | | | | | 95 | |
| Ile | Thr | Pro | Ala | Ile | Thr | Arg | Val | Val | Asp | Phe | Ala | Lys | Asn | Leu | Pro |
| | | | 100 | | | | | 105 | | | | | 110 | | |
| Met | Phe | Ser | Glu | Leu | Pro | Cys | Glu | Asp | Gln | Ile | Ile | Leu | Leu | Lys | Gly |
| | | 115 | | | | | 120 | | | | | 125 | | | |
| Cys | Cys | Met | Glu | Ile | Met | Ser | Leu | Arg | Ala | Ala | Val | Arg | Tyr | Asp | Pro |
| | 130 | | | | | 135 | | | | | 140 | | | | |
| Glu | Ser | Glu | Thr | Leu | Thr | Leu | Ser | Gly | Glu | Met | Ala | Val | Lys | Arg | Glu |
| 145 | | | | | 150 | | | | | 155 | | | | | 160 |
| Gln | Leu | Lys | Asn | Gly | Gly | Leu | Gly | Val | Val | Ser | Asp | Ala | Ile | Phe | Asp |
| | | | | 165 | | | | | 170 | | | | | 175 | |
| Leu | Gly | Lys | Ser | Leu | Ser | Ala | Phe | Asn | Leu | Asp | Asp | Thr | Glu | Val | Ala |
| | | | 180 | | | | | 185 | | | | | 190 | | |
| Leu | Leu | Gln | Ala | Val | Leu | Leu | Met | Ser | Ser | Asp | Arg | Thr | Gly | Leu | Ile |
| | | 195 | | | | | 200 | | | | | 205 | | | |
| Cys | Val | Asp | Lys | Ile | Glu | Lys | Cys | Gln | Glu | Ser | Tyr | Leu | Leu | Ala | Phe |
| | 210 | | | | | 215 | | | | | 220 | | | | |
| Glu | His | Tyr | Ile | Asn | Tyr | Arg | Lys | His | Asn | Ile | Pro | His | Phe | Trp | Ser |
| 225 | | | | | 230 | | | | | 235 | | | | | 240 |
| Lys | Leu | Leu | Met | Lys | Val | Ala | Asp | Leu | Arg | Met | Ile | Gly | Ala | Tyr | His |
| | | | | 245 | | | | | 250 | | | | | 255 | |
| Ala | Ser | Arg | Phe | Leu | His | Met | Lys | Val | Glu | Cys | Pro | Thr | Glu | Leu | Ser |
| | | | 260 | | | | | 265 | | | | | 270 | | |

( 2 ) INFORMATION FOR SEQ ID NO:24:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:24:

TCCCCGGGTA ACTAAGTAAG GATCC        25

( 2 ) INFORMATION FOR SEQ ID NO:25:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:25:

AGTGGGTCCC CGGGTGACAT GGAA        24

( 2 ) INFORMATION FOR SEQ ID NO:26:

( i ) SEQUENCE CHARACTERISTICS:
        ( A ) LENGTH: 8 amino acids
        ( B ) TYPE: amino acid
        ( D ) TOPOLOGY: linear

```
( i i ) MOLECULE TYPE: polypeptide ( v ) FRAGMENT TYPE: internal ( x i ) SEQUENCE DESCRIPTION: SEQ ID NO:26:

Ser Gly Ser Pro Gly Asp Met Glu
 1               5

( 2 ) INFORMATION FOR SEQ ID NO:27:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:27:

AGTGGGTCCC CGGGTCTGGA CGAC                                              2 4

( 2 ) INFORMATION FOR SEQ ID NO:28:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: polypeptide ( v ) FRAGMENT TYPE: internal ( x i ) SEQUENCE DESCRIPTION: SEQ ID NO:28:

Ser Gly Ser Pro Gly Leu Asp Asp
 1               5
```